(12) United States Patent
Kriesel et al.

(10) Patent No.: US 7,470,253 B2
(45) Date of Patent: Dec. 30, 2008

(54) FLUID DELIVERY APPARATUS WITH ADJUSTABLE FLOW RATE CONTROL

(75) Inventors: Marshall S. Kriesel, St. Paul, MN (US); Joshua W. Kriesel, San Francisco, CA (US)

(73) Assignee: BioQuiddity, Inc., San Francisco, CA (US)

( * ) Notice: Subject to any disclaimer, the term of this patent is extended or adjusted under 35 U.S.C. 154(b) by 743 days.

(21) Appl. No.: 10/854,830

(22) Filed: May 26, 2004

(65) Prior Publication Data

US 2005/0263615 A1    Dec. 1, 2005

(51) Int. Cl.
*A61M 5/20*   (2006.01)
*A61M 5/00*   (2006.01)
*A61K 9/22*   (2006.01)

(52) U.S. Cl. ............ 604/134; 604/890.1; 604/891.1; 604/131; 604/133; 604/135; 604/151; 604/153; 604/246; 604/247; 604/248; 604/207; 604/211; 604/216; 604/236

(58) Field of Classification Search ......... 604/134–136, 604/151, 153, 246–248, 256, 260, 207, 211, 604/216, 236, 131, 890.1, 891.1
See application file for complete search history.

(56) References Cited

U.S. PATENT DOCUMENTS

| | | | |
|---|---|---|---|
| 3,731,681 A | 5/1973 | Blackshear et al. |
| 4,381,006 A | 4/1983 | Genese |
| 4,557,728 A | 12/1985 | Sealfon et al. |
| 4,608,042 A | 8/1986 | Vanderveen et al. |
| 4,681,566 A | 7/1987 | Fenton, Jr. et al. |
| 4,755,172 A | 7/1988 | Baldwin |
| 4,772,263 A | 9/1988 | Dorman et al. |
| 4,850,807 A | 7/1989 | Frantz |
| 4,863,429 A | 9/1989 | Baldwin |
| 5,014,750 A | 5/1991 | Winchell et al. |
| 5,098,377 A | 3/1992 | Borsanyi et al. |
| 5,100,389 A | 3/1992 | Vaillancourt |
| 5,176,641 A | 1/1993 | Idriss |
| 5,205,820 A | 4/1993 | Kriesel |
| 5,236,418 A | 8/1993 | Kriesel |
| 5,290,259 A | 3/1994 | Fischer |
| 5,306,257 A | 4/1994 | Zdeb |
| 5,314,405 A | 5/1994 | Kriesel et al. |
| 5,336,188 A | 8/1994 | Kriesel |
| 5,346,476 A | 9/1994 | Elson |
| 5,380,287 A | 1/1995 | Kikuchi et al. |
| 5,411,480 A | 5/1995 | Kriesel |
| 5,419,771 A | 5/1995 | Kriesel |
| 5,484,410 A | 1/1996 | Kriesel et al. |
| 5,499,968 A | 3/1996 | Milijasevic et al. |
| 5,514,090 A | 5/1996 | Kriesel et al. |
| 5,545,139 A | 8/1996 | Kriesel |
| 5,620,420 A | 4/1997 | Kriesel |
| 5,693,018 A | 12/1997 | Kriesel et al. |

(Continued)

*Primary Examiner*—Nicholas D Lucchesi
*Assistant Examiner*—Quynh-Nhu H Vu

(57) ABSTRACT

A compact fluid dispenser for use in controllably dispensing fluid medicaments, such as, antibiotics, analgesics, and like medicinal agents from the device reservoir. The fluid dispenser includes a unique stored energy mechanism which takes the form of a constant force spring member of novel design that provides the force necessary to continuously and substantially uniformly expel fluid from the device reservoir. The device also includes novel adjustable flow rate control assembly that is disposed intermediate the fluid reservoir outlet and the outlet port of the device for precisely controlling the rate of fluid flow from the outlet port toward the patient.

30 Claims, 68 Drawing Sheets

U.S. PATENT DOCUMENTS

| | | | | |
|---|---|---|---|---|
| 5,720,729 | A | 2/1998 | Kriesel | |
| 5,721,382 | A | 2/1998 | Kriesel et al. | |
| 5,735,818 | A | 4/1998 | Kriesel et al. | |
| 5,741,242 | A | 4/1998 | Kriesel | |
| 5,743,879 | A | 4/1998 | Kriesel | |
| 5,766,149 | A | 6/1998 | Kriesel et al. | |
| 5,779,676 | A | 7/1998 | Kriesel et al. | |
| 5,807,323 | A | 9/1998 | Kriesel et al. | |
| 5,836,484 | A | 11/1998 | Gerber | |
| 5,843,036 | A * | 12/1998 | Olive et al. | 604/136 |
| 5,858,005 | A | 1/1999 | Kriesel | |
| 5,885,250 | A | 3/1999 | Kriesel et al. | |
| 5,897,530 | A | 4/1999 | Jackson | |
| 5,921,962 | A | 7/1999 | Kriesel et al. | |
| 5,925,017 | A | 7/1999 | Kriesel et al. | |
| 5,957,891 | A | 9/1999 | Kriesel et al. | |
| 5,993,425 | A | 11/1999 | Kriesel | |
| 6,010,482 | A | 1/2000 | Kriesel et al. | |
| 6,027,472 | A | 2/2000 | Kriesel et al. | |
| 6,030,363 | A | 2/2000 | Kriesel | |
| 6,045,533 | A | 4/2000 | Kriesel et al. | |
| 6,056,728 | A * | 5/2000 | von Schuckmann | 604/207 |
| 6,063,059 | A | 5/2000 | Kriesel | |
| 6,068,613 | A | 5/2000 | Kriesel et al. | |
| 6,068,614 | A | 5/2000 | Kimber et al. | |
| 6,086,561 | A | 7/2000 | Kriesel et al. | |
| 6,090,071 | A | 7/2000 | Kriesel | |
| 6,095,491 | A | 8/2000 | Kriesel | |
| 6,126,637 | A | 10/2000 | Kriesel et al. | |
| 6,126,642 | A | 10/2000 | Kriesel et al. | |
| 6,152,898 | A | 11/2000 | Olsen | |
| 6,159,180 | A | 12/2000 | Kriesel et al. | |
| 6,176,845 | B1 | 1/2001 | Kriesel et al. | |
| 6,183,441 | B1 | 2/2001 | Kriesel et al. | |
| 6,190,359 | B1 | 2/2001 | Heruth | |
| 6,210,368 | B1 | 4/2001 | Rogers | |
| 6,236,624 | B1 | 5/2001 | Kriesel et al. | |
| 6,245,041 | B1 | 6/2001 | Kriesel | |
| 6,258,062 | B1 | 7/2001 | Thielen et al. | |
| 6,270,481 | B1 | 8/2001 | Mason et al. | |
| 6,273,133 | B1 | 8/2001 | Williamson et al. | |
| 6,277,095 | B1 | 8/2001 | Kriesel et al. | |
| 6,293,159 | B1 | 9/2001 | Kriesel et al. | |
| 6,319,235 | B1 | 11/2001 | Yoshino | |
| 6,355,019 | B1 | 3/2002 | Kriesel et al. | |
| 6,391,006 | B1 | 5/2002 | Kriesel et al. | |
| 6,394,980 | B2 | 5/2002 | Kriesel et al. | |
| 6,398,760 | B1 | 6/2002 | Danby | |
| 6,416,495 | B1 * | 7/2002 | Kriesel et al. | 604/132 |
| 6,485,461 | B1 | 11/2002 | Mason et al. | |
| 6,537,249 | B2 | 3/2003 | Kriesel et al. | |
| 6,542,350 | B1 | 4/2003 | Rogers | |
| 6,569,125 | B2 | 5/2003 | Jepson et al. | |
| 6,645,175 | B2 | 11/2003 | Kriesel et al. | |
| 6,669,668 | B1 | 12/2003 | Kleeman et al. | |
| 7,220,244 | B2 * | 5/2007 | Kriesel | 604/134 |
| 7,220,245 | B2 * | 5/2007 | Kriesel | 604/134 |
| 2002/0177809 | A1 * | 11/2002 | Kriesel et al. | 604/132 |

* cited by examiner

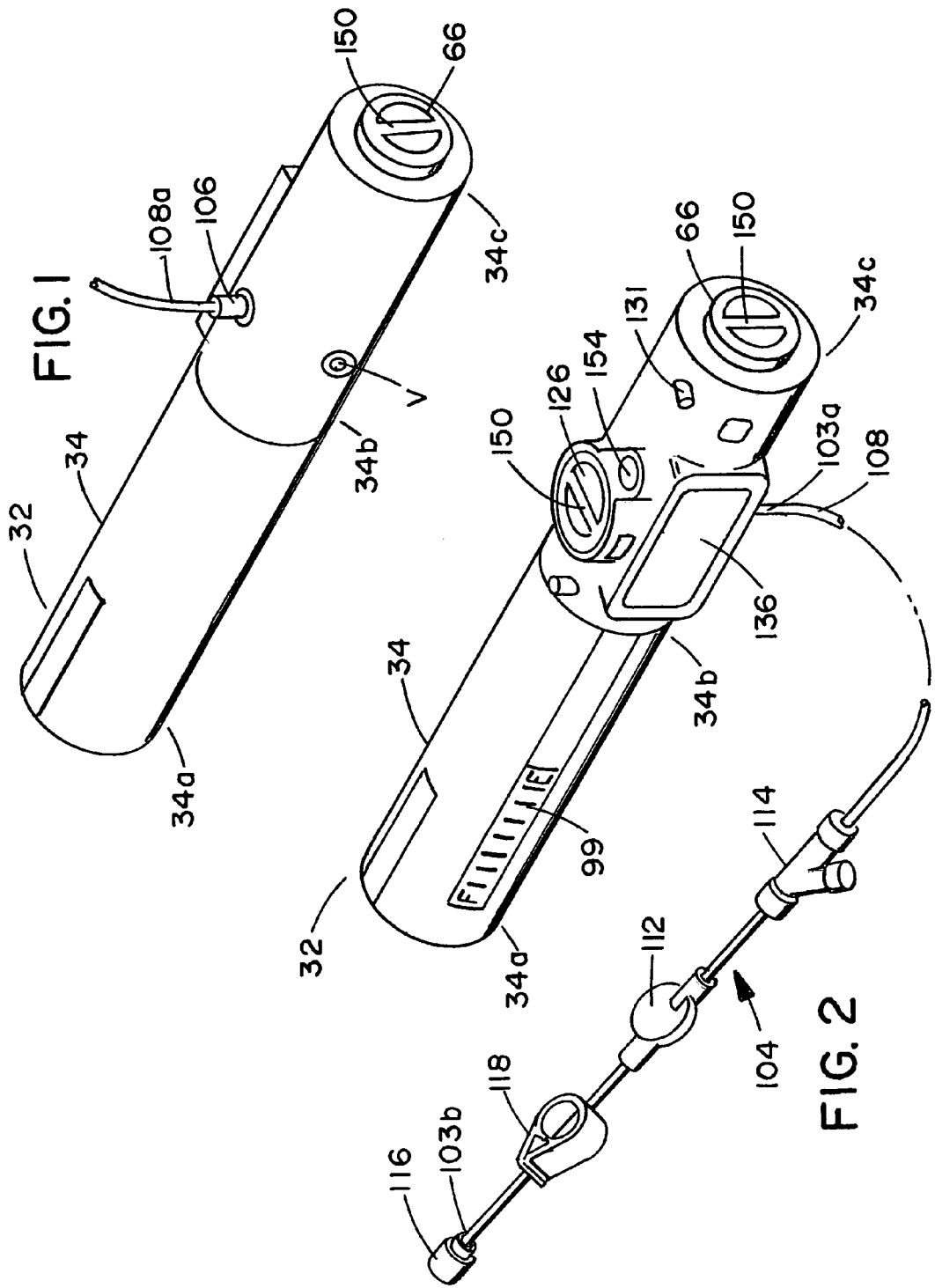

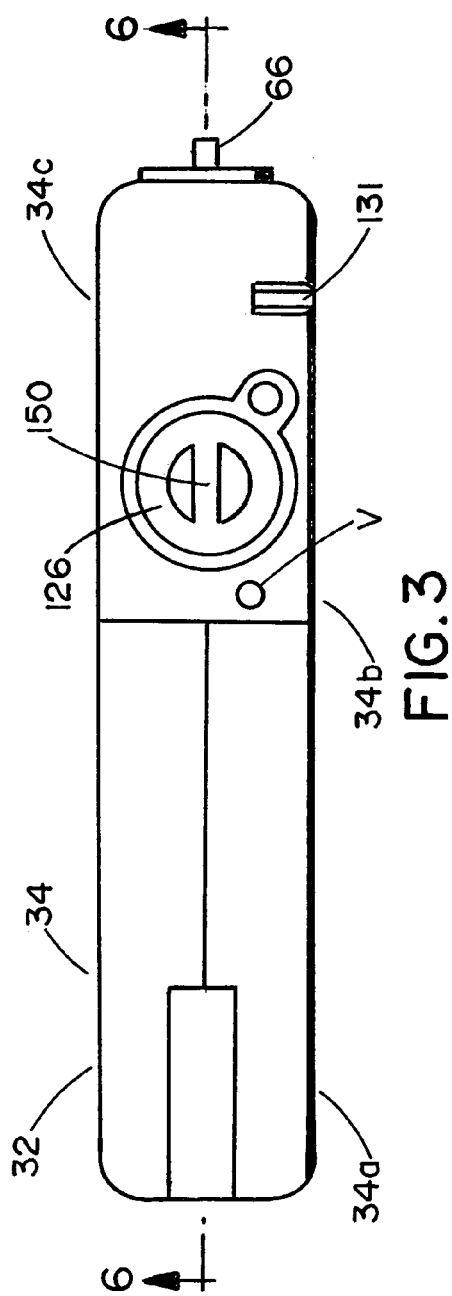
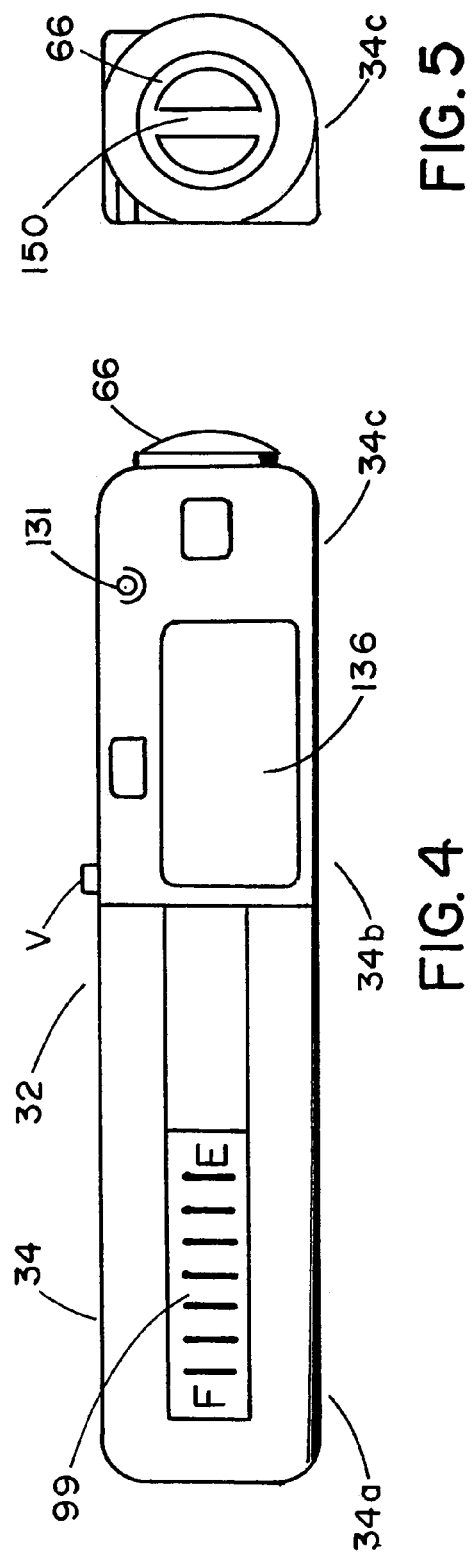

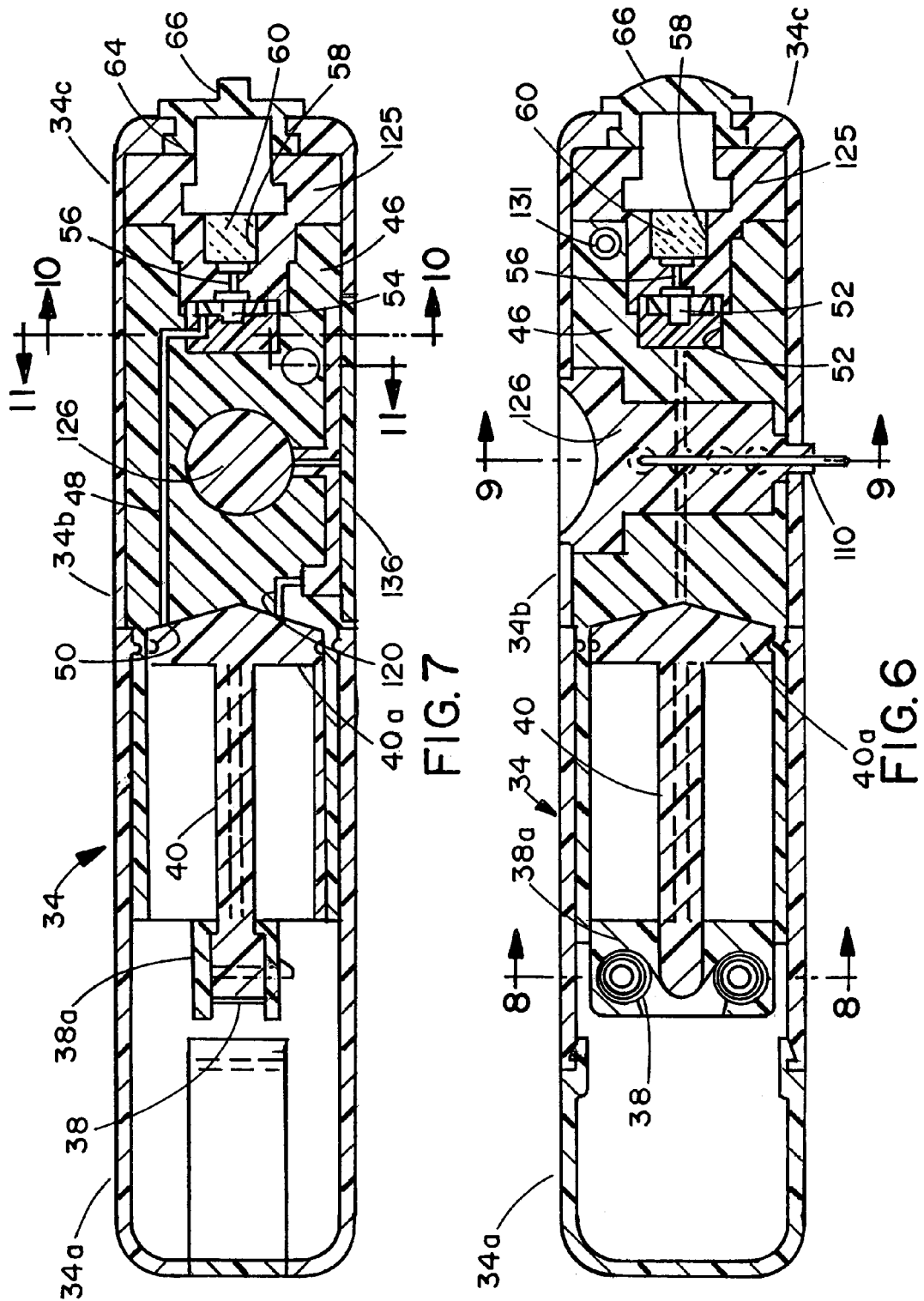

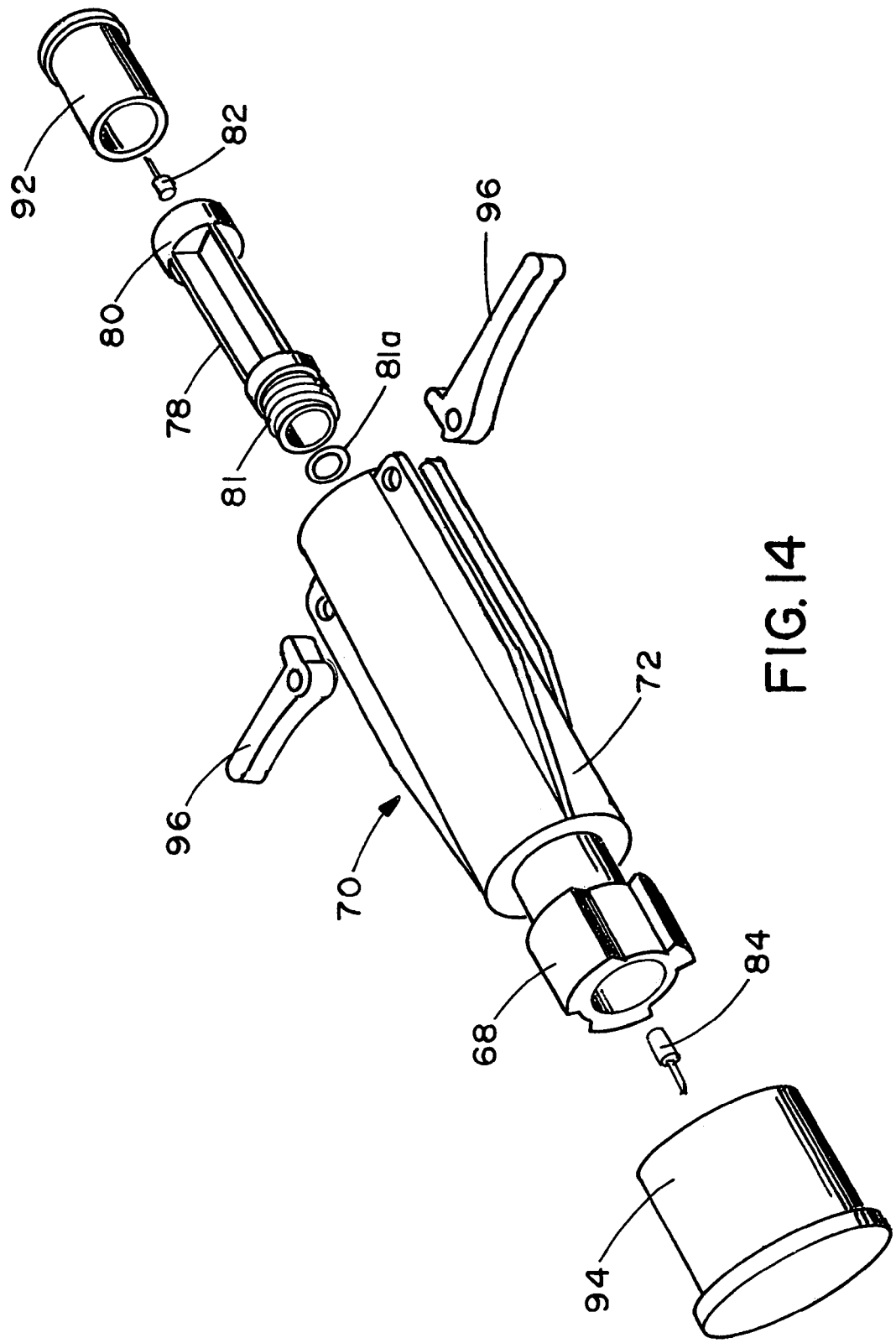

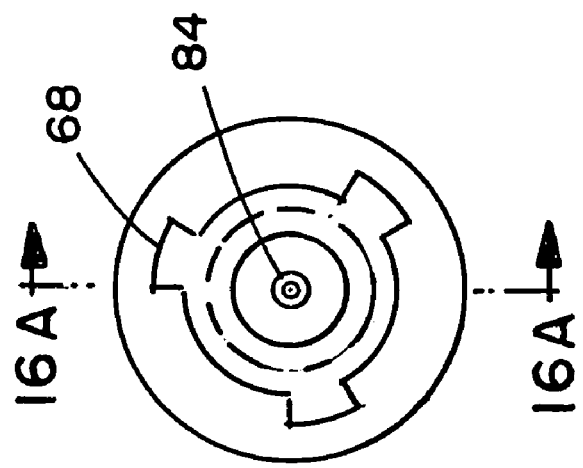
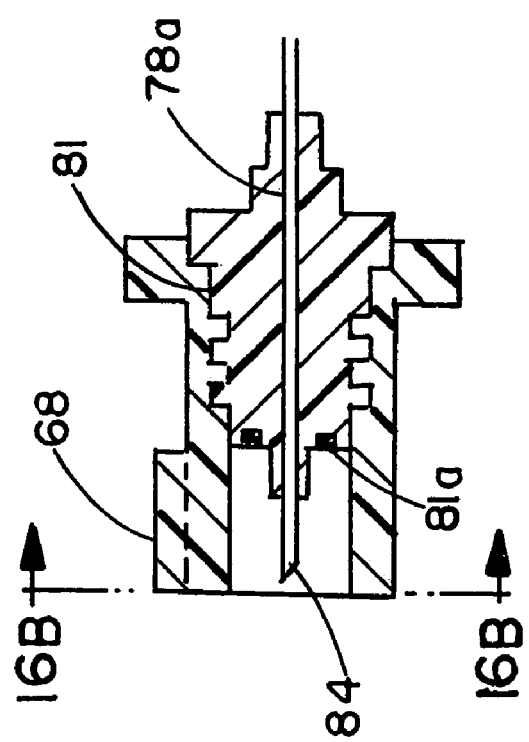
FIG.16B
FIG.16A

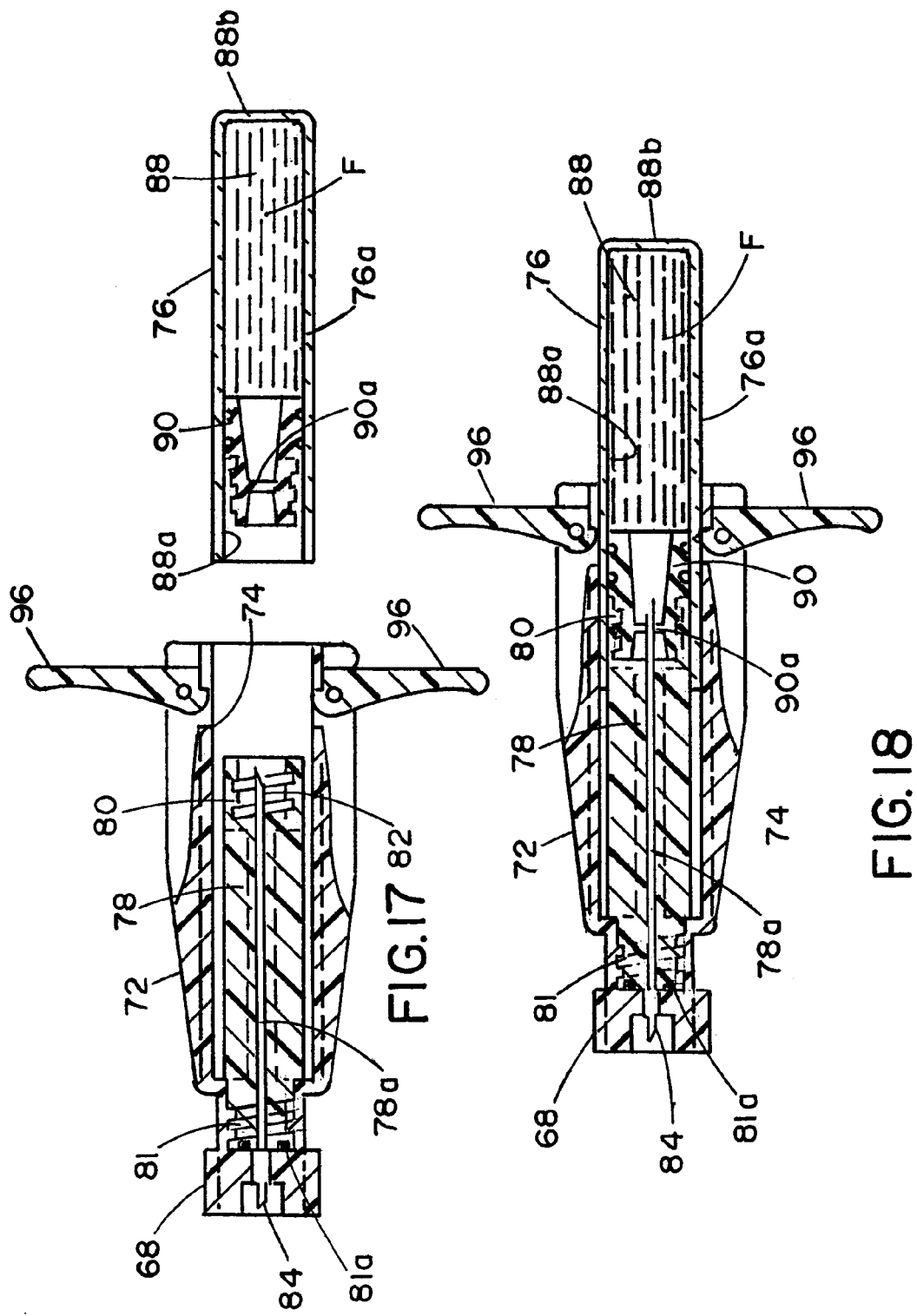

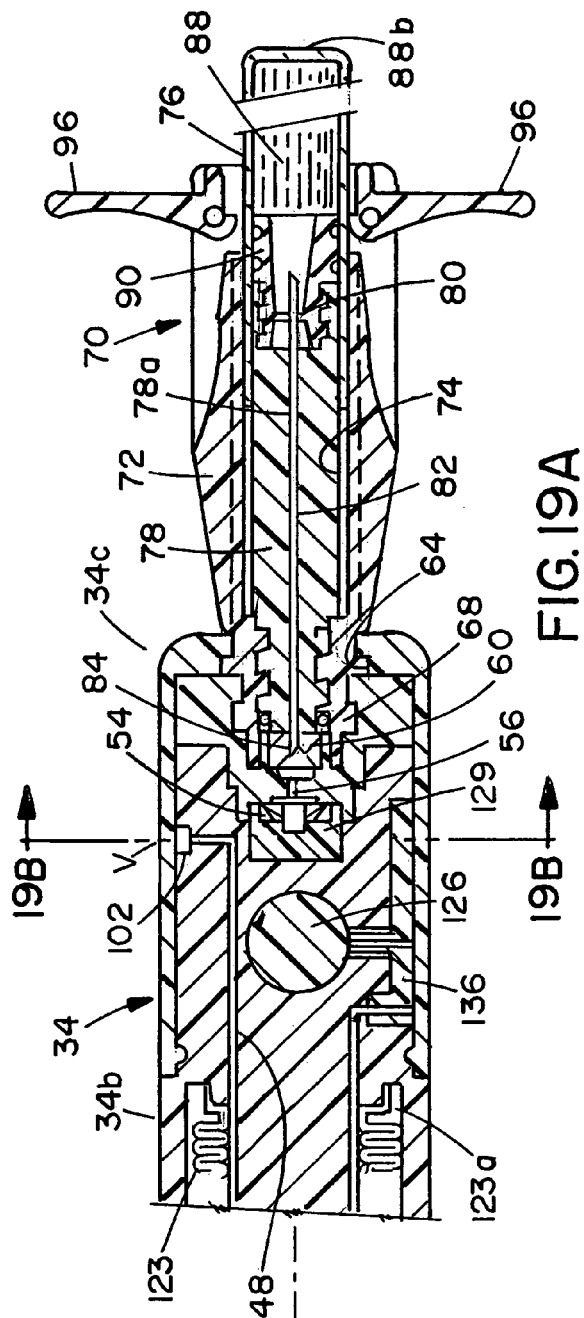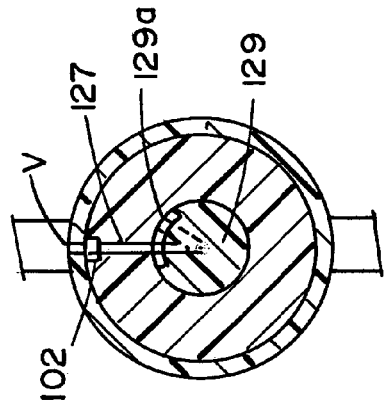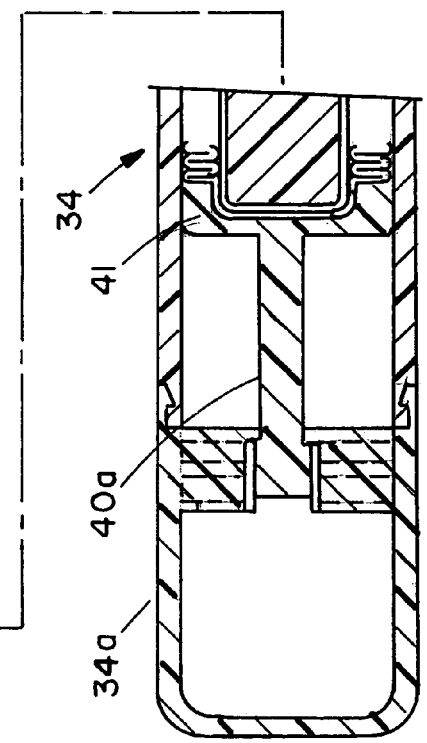

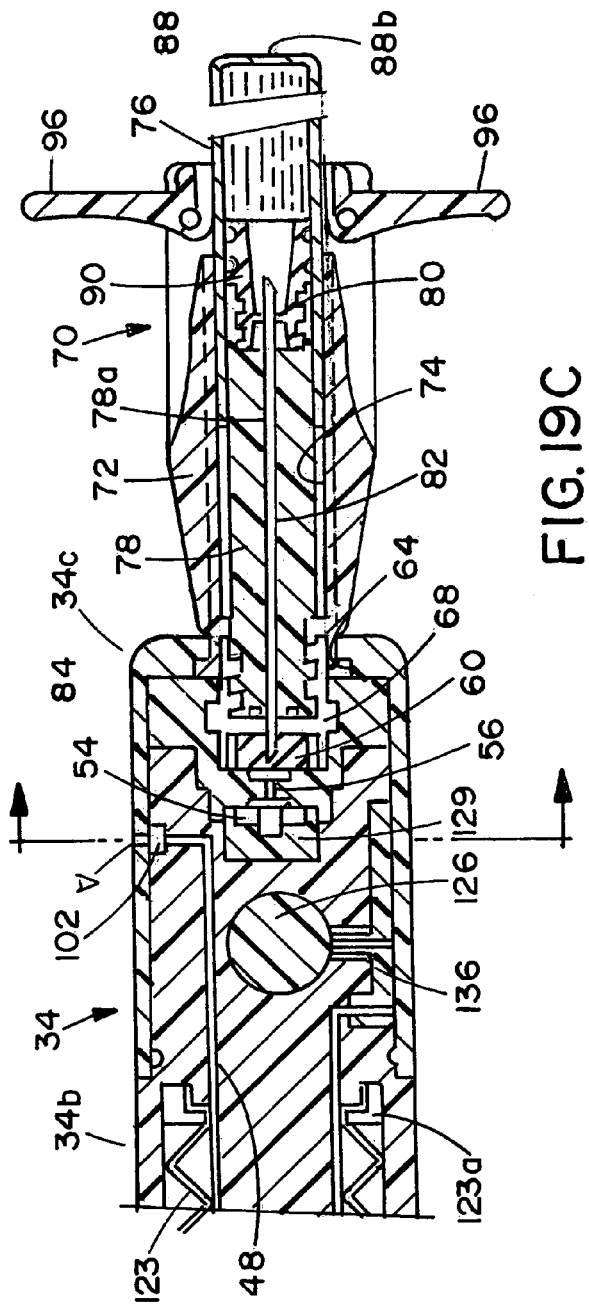
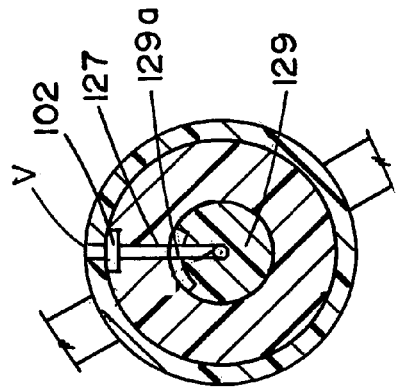
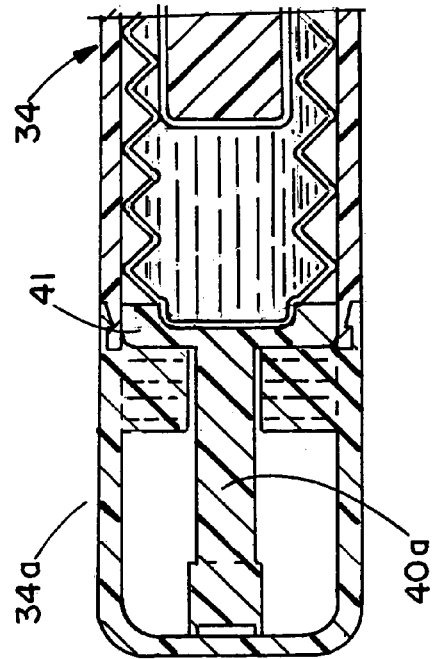
FIG. 19C
FIG. 19D

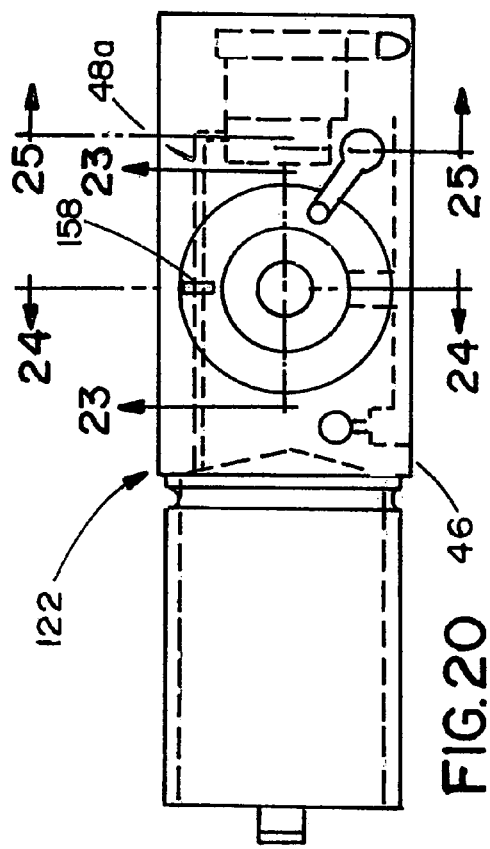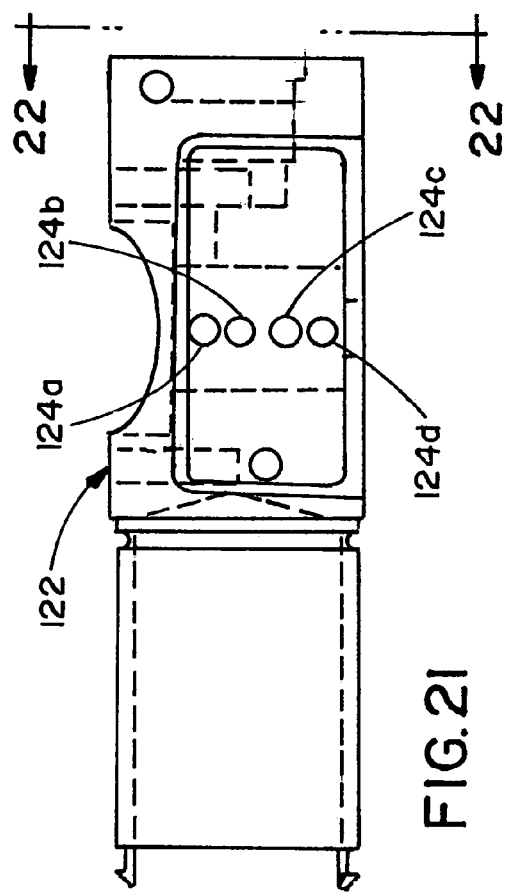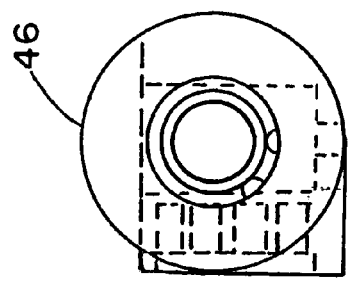

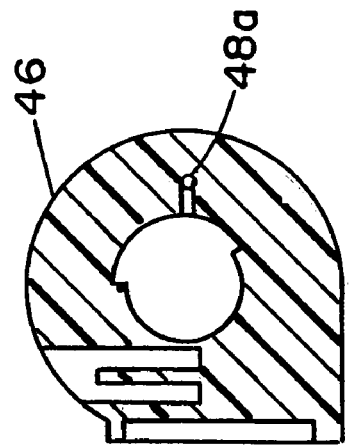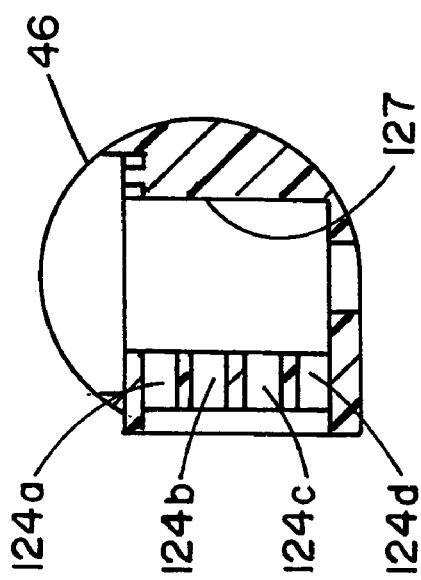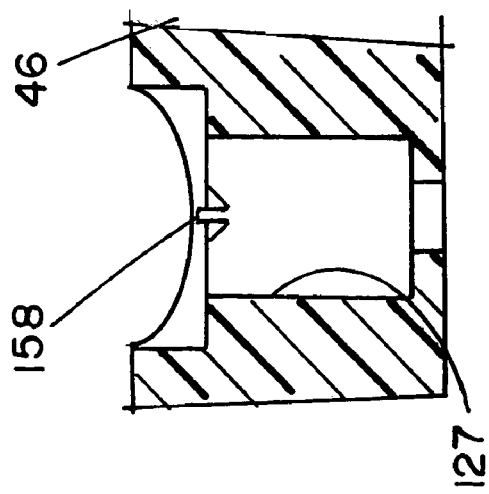

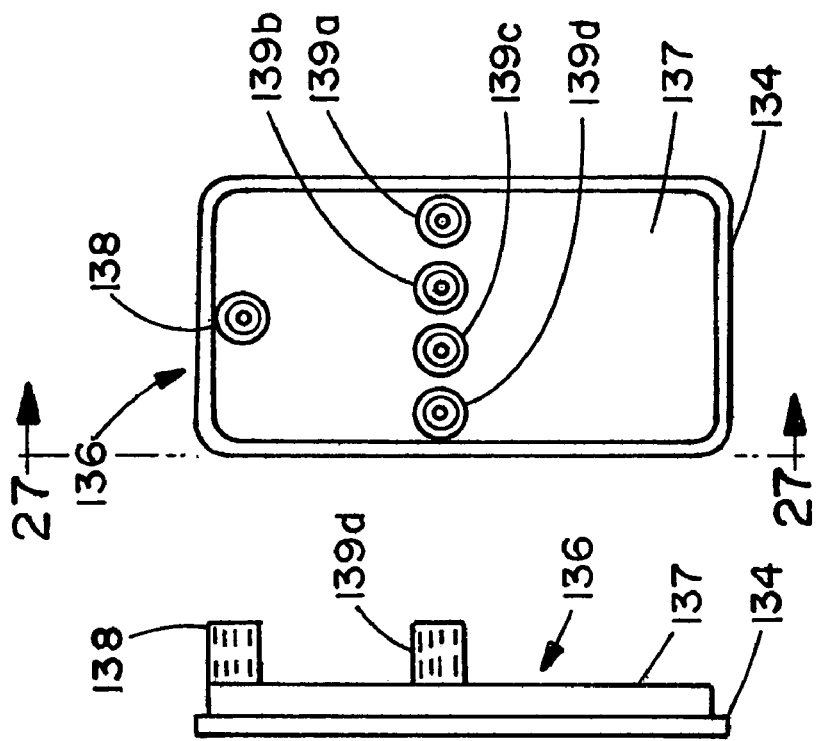
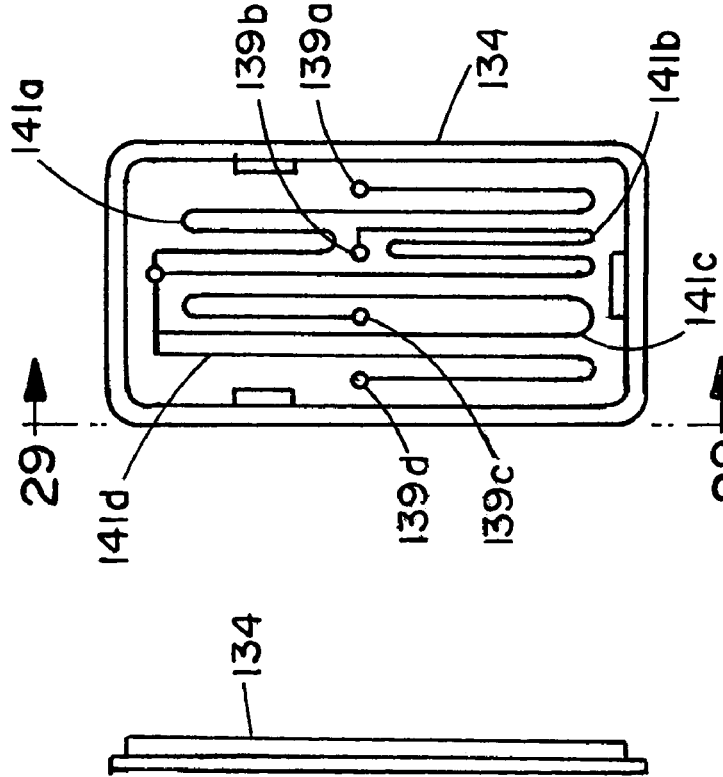
FIG. 26
FIG. 27
FIG. 28
FIG. 29

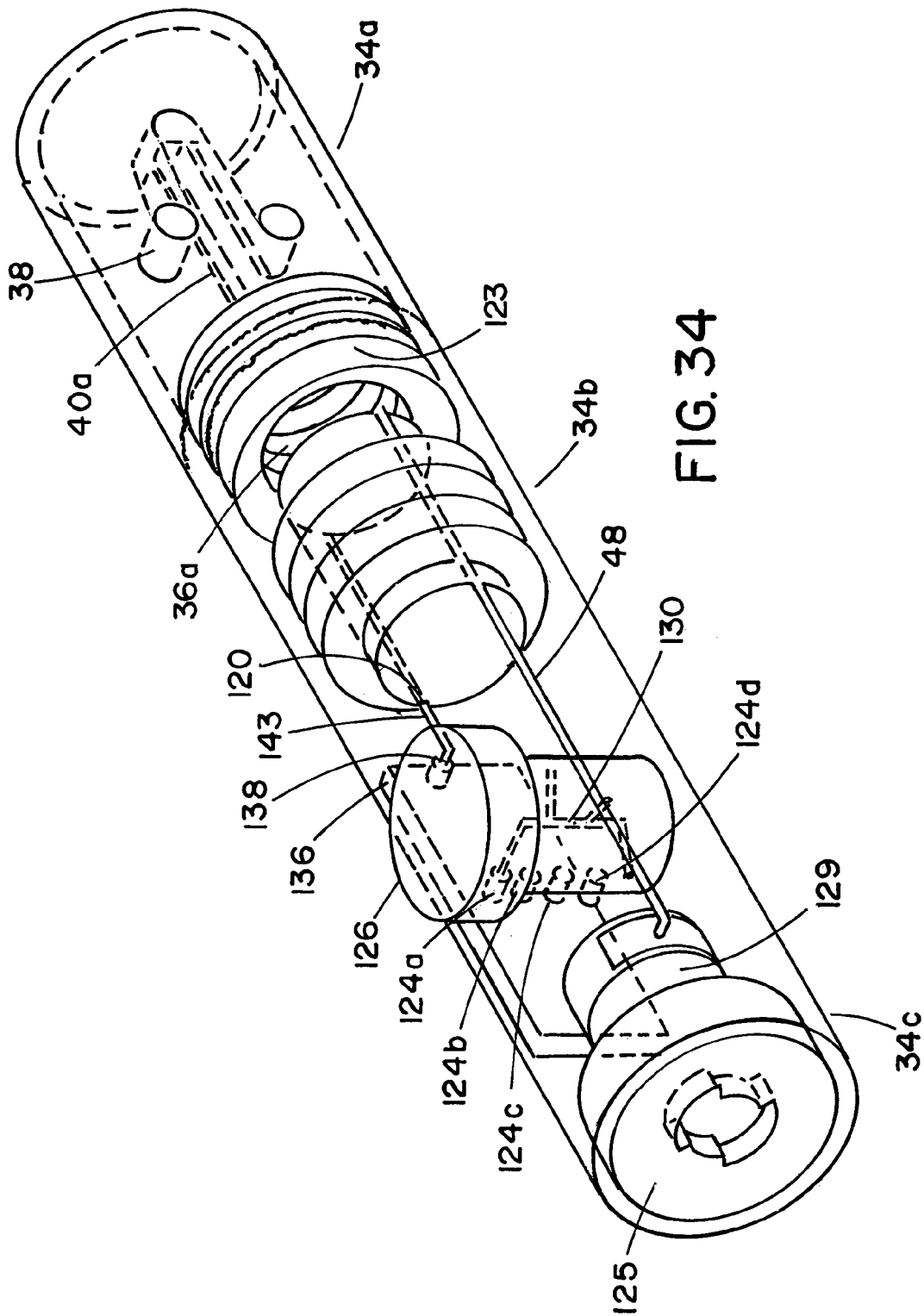

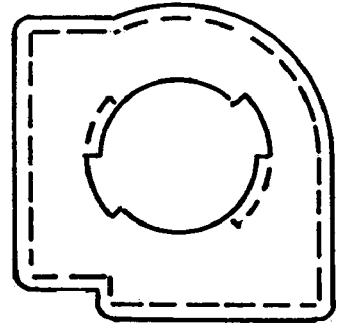
FIG. 37
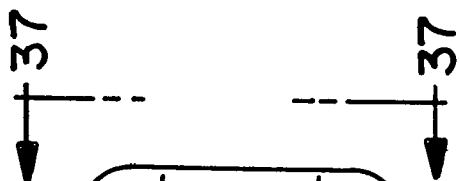
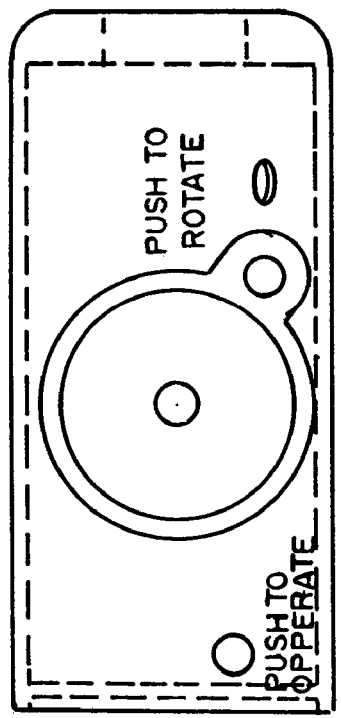
FIG. 35
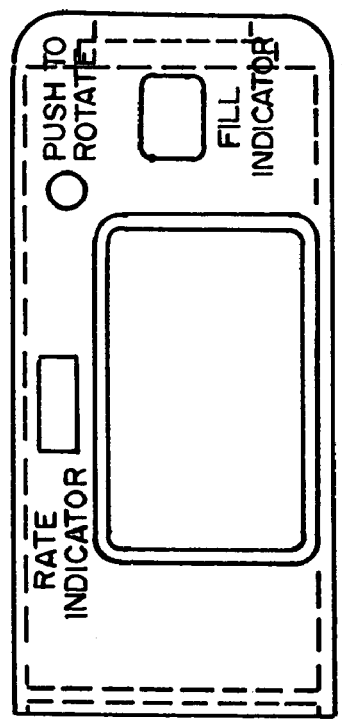
FIG. 36

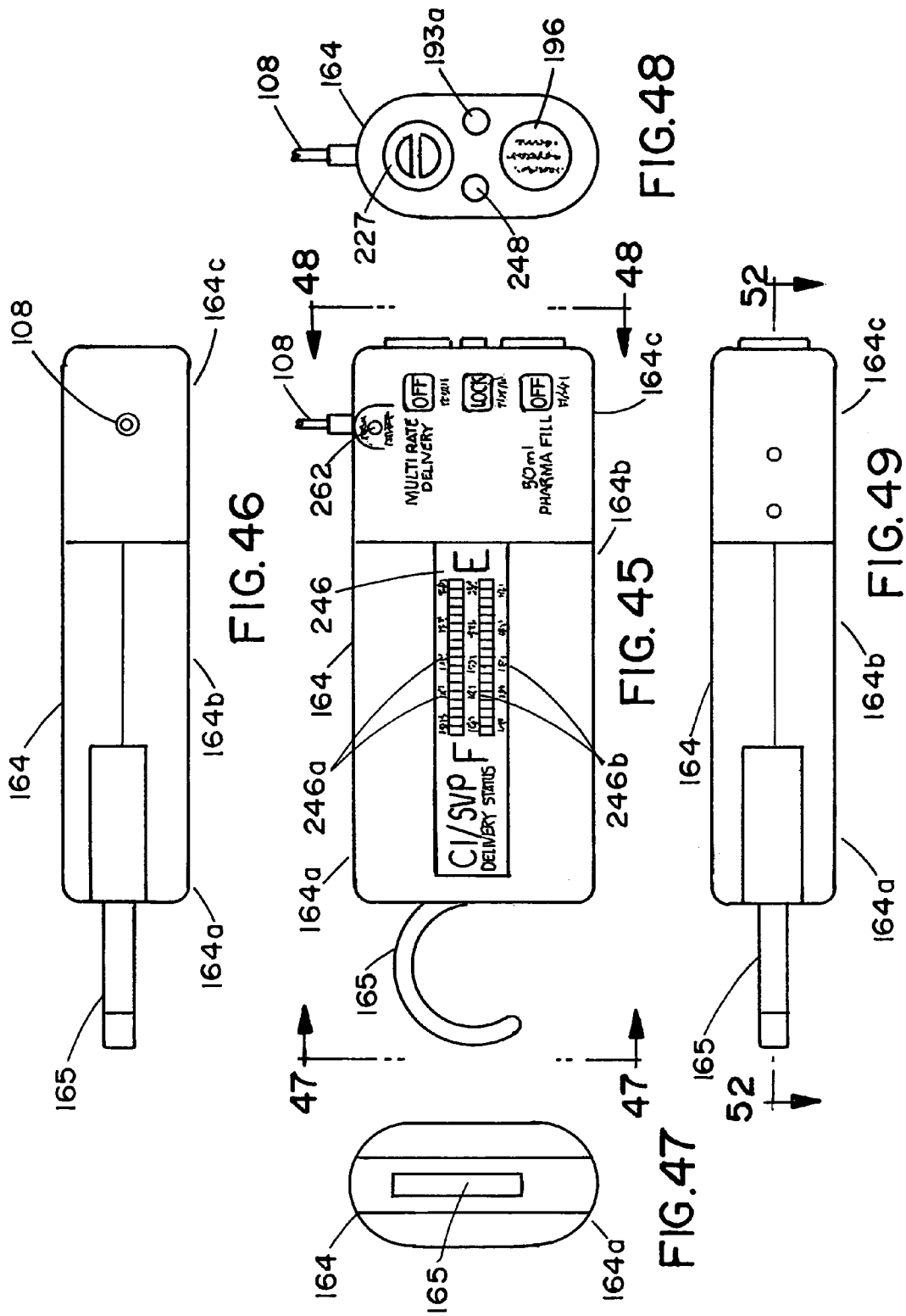

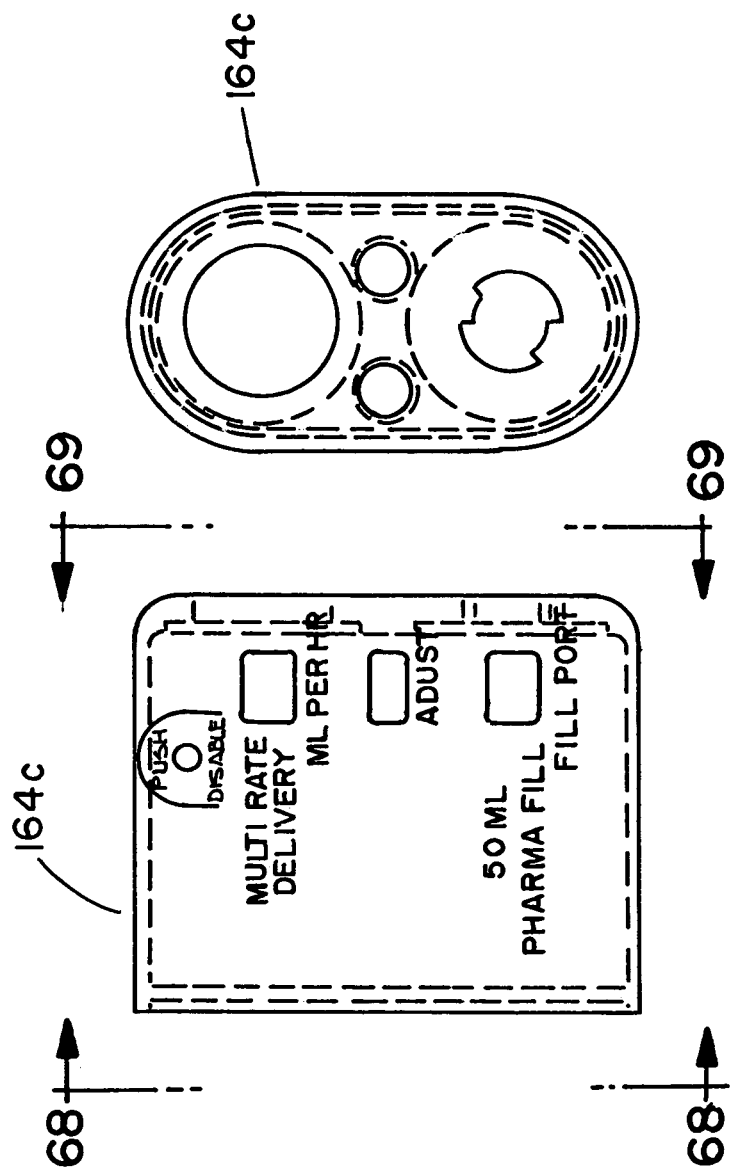
FIG. 69
FIG. 67
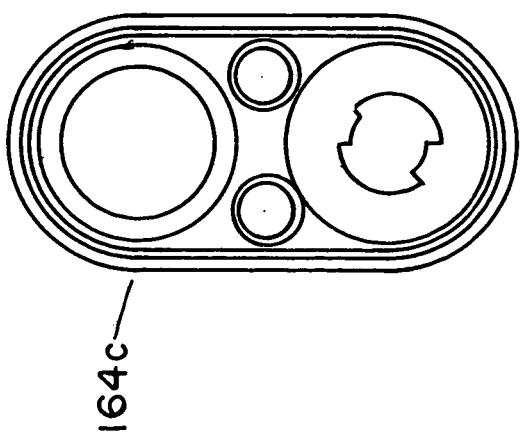
FIG. 68

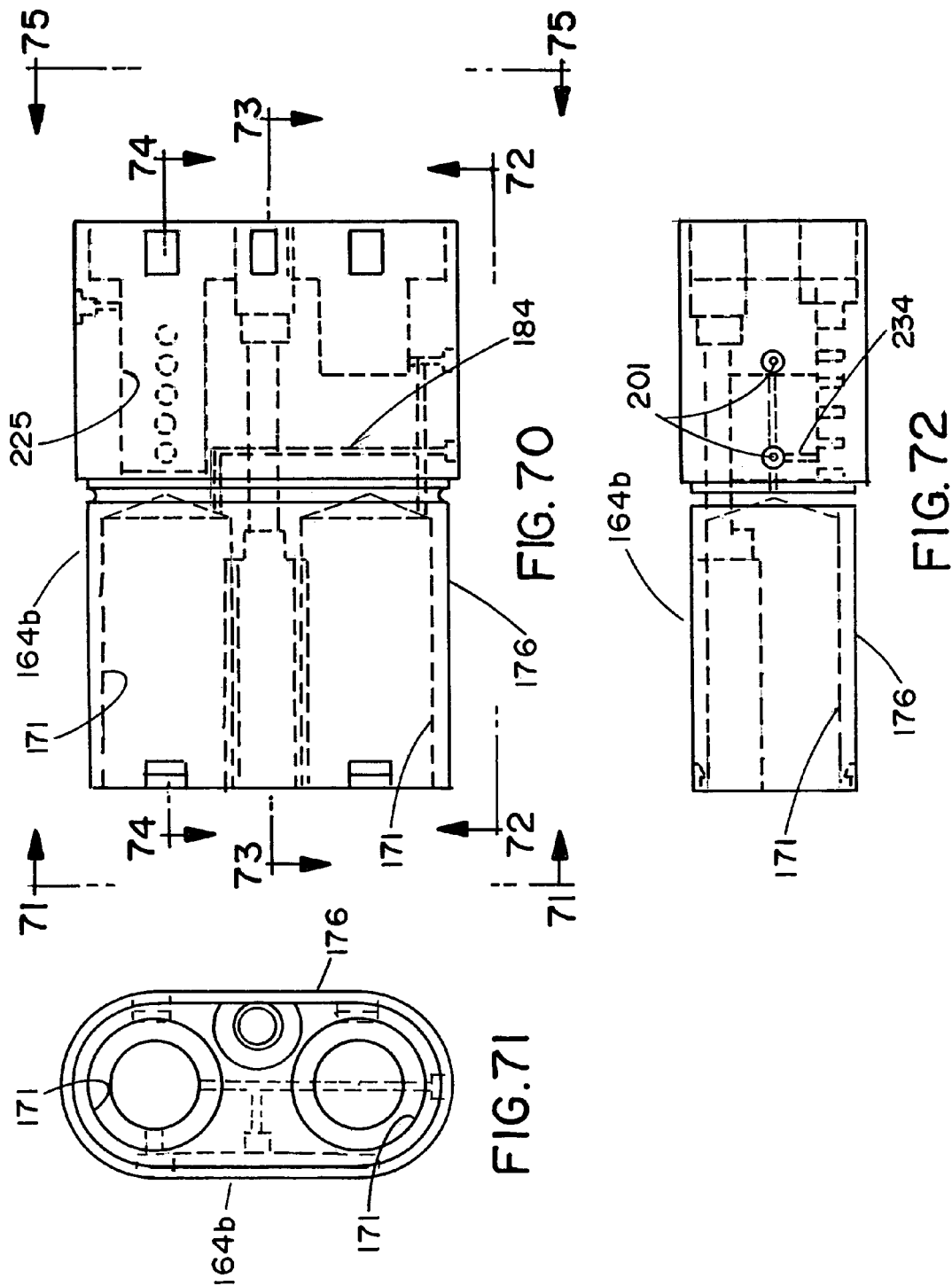

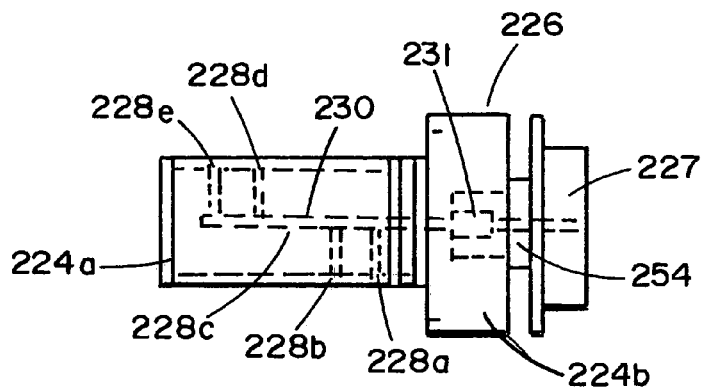
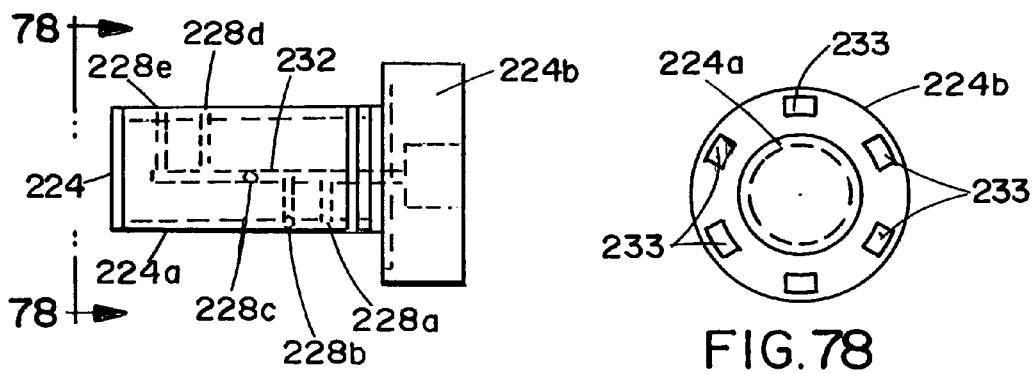
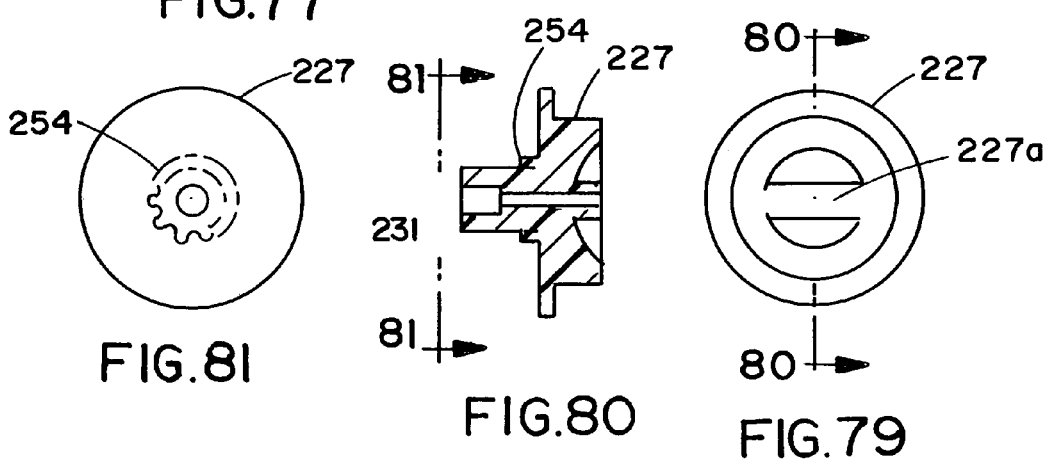

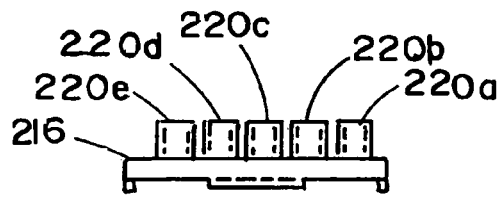
FIG. 82　　　　　FIG. 86
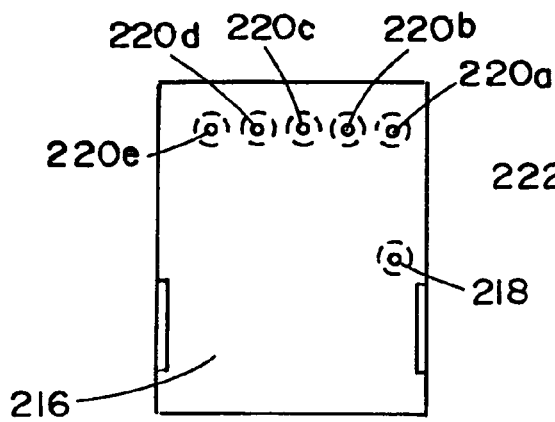
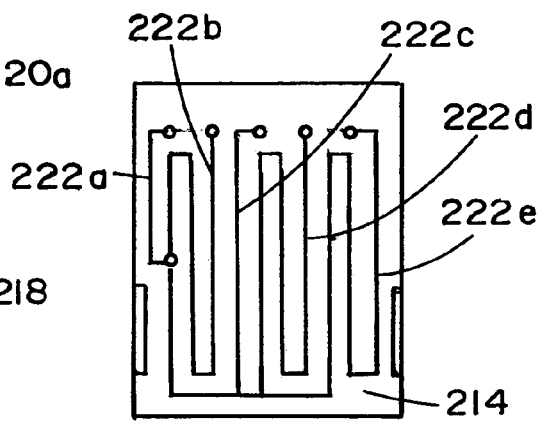
FIG. 83　　　　　FIG. 87
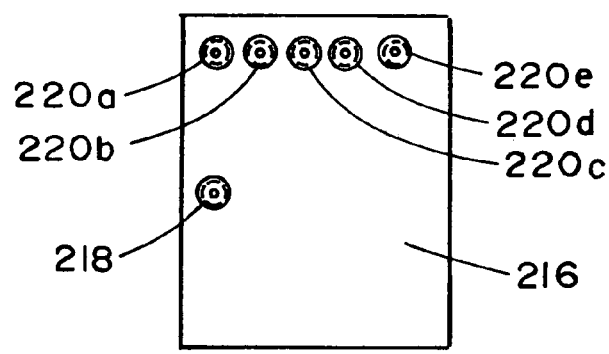
FIG. 84
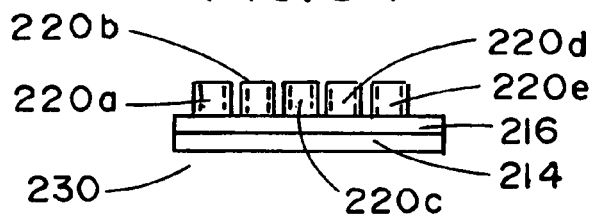
FIG. 85

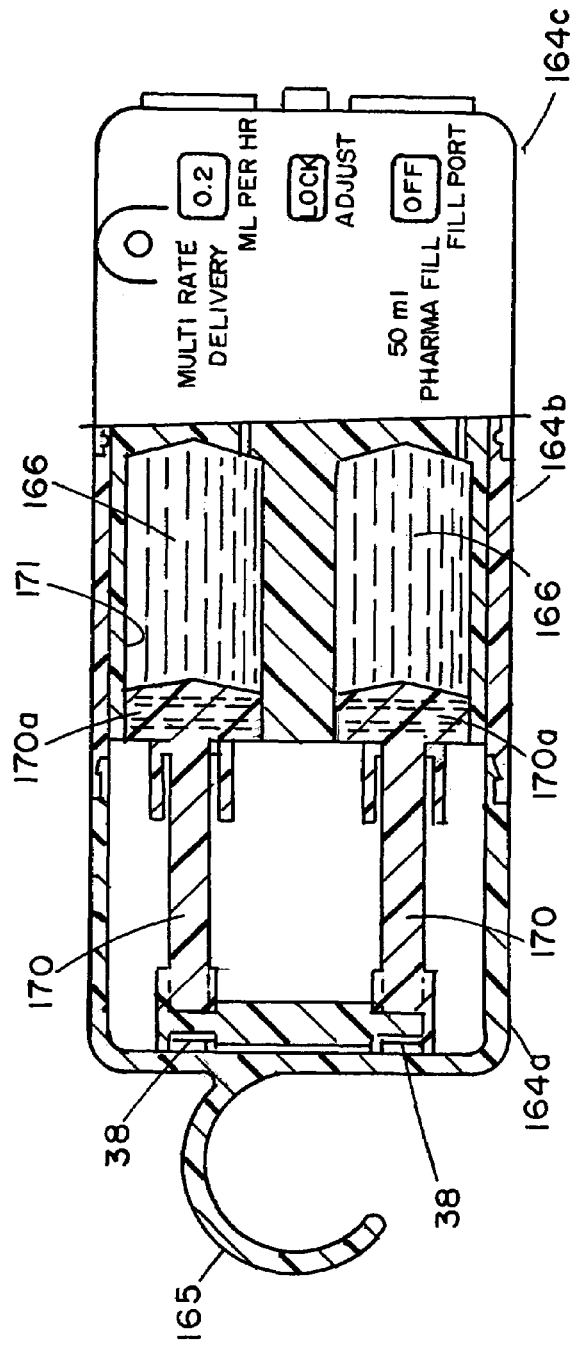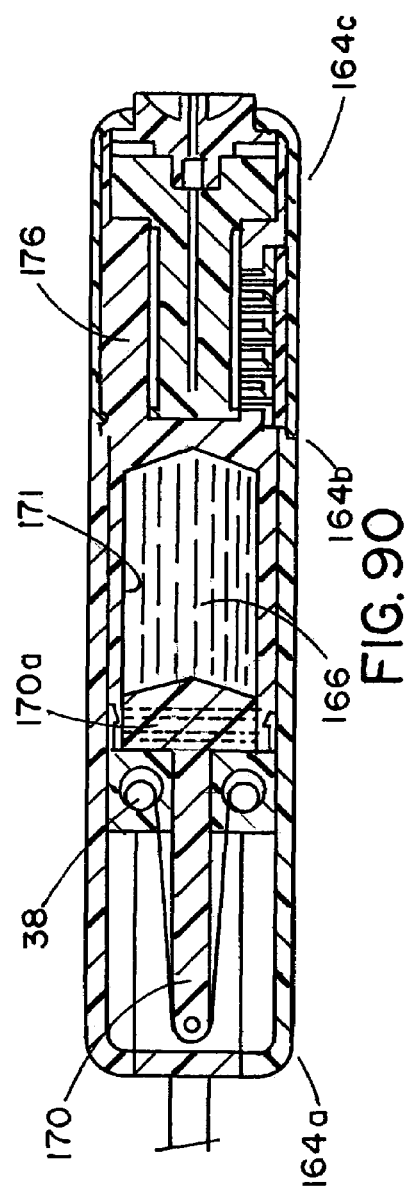

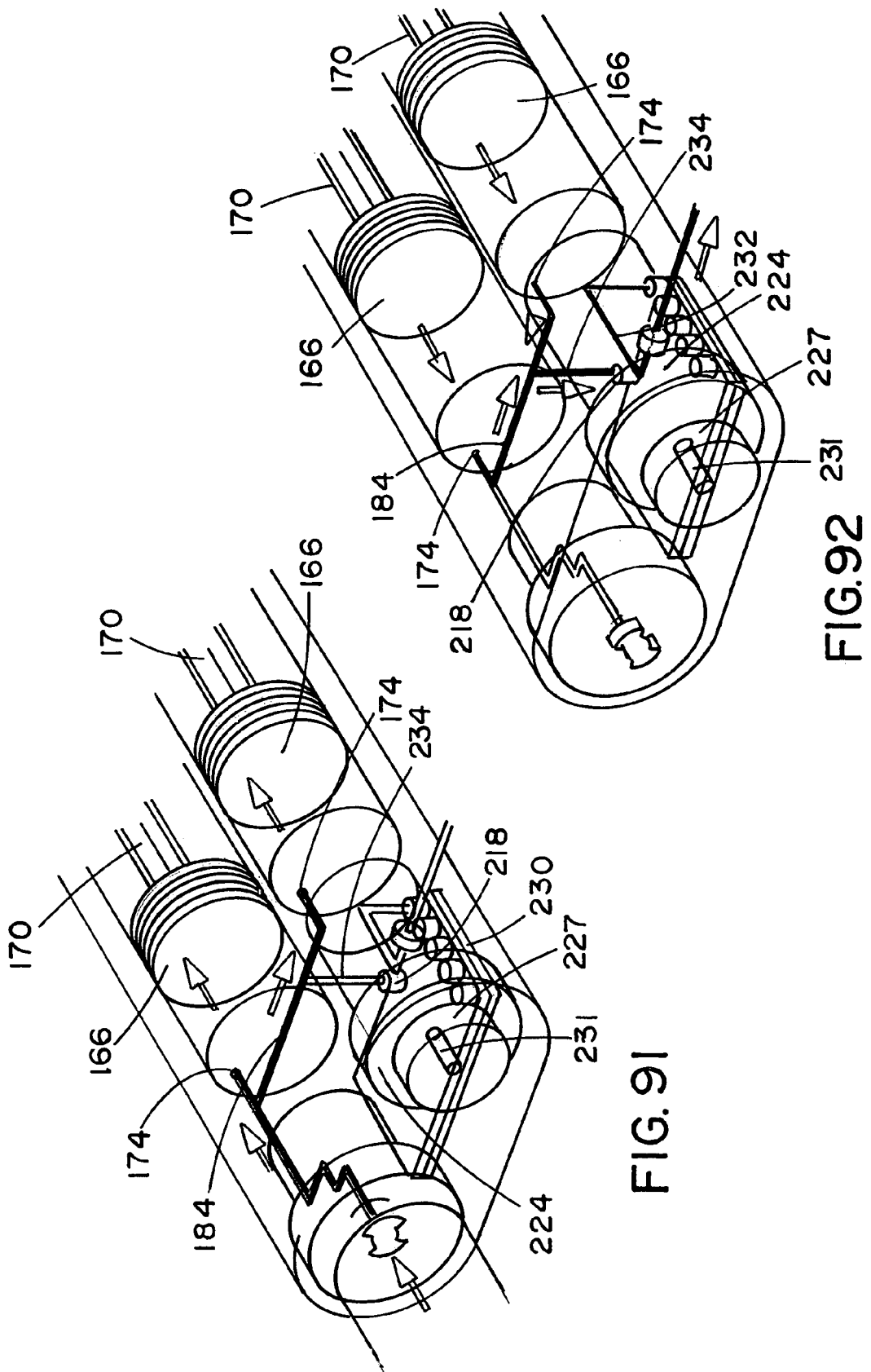

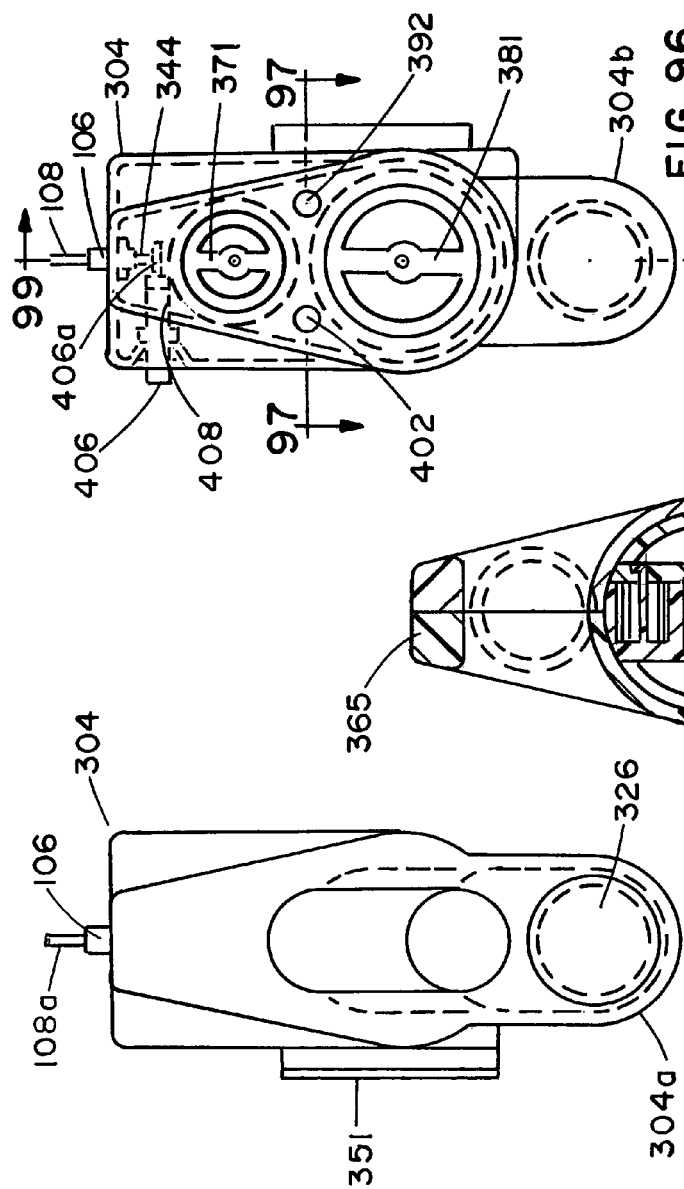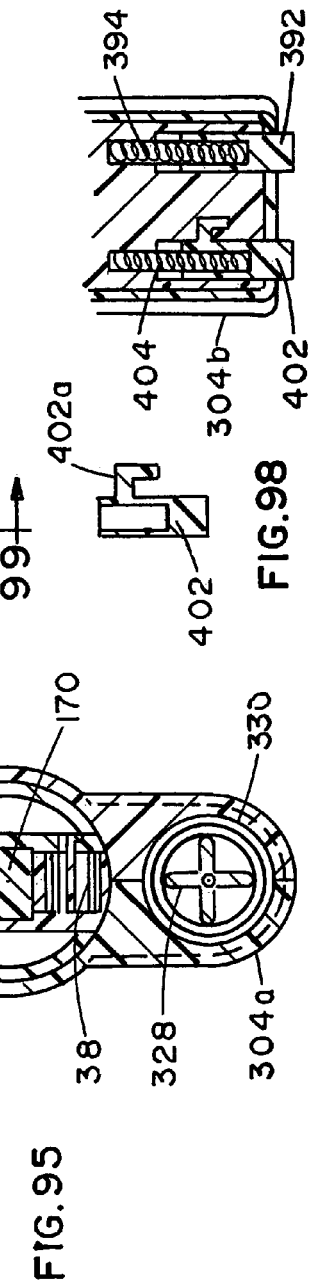

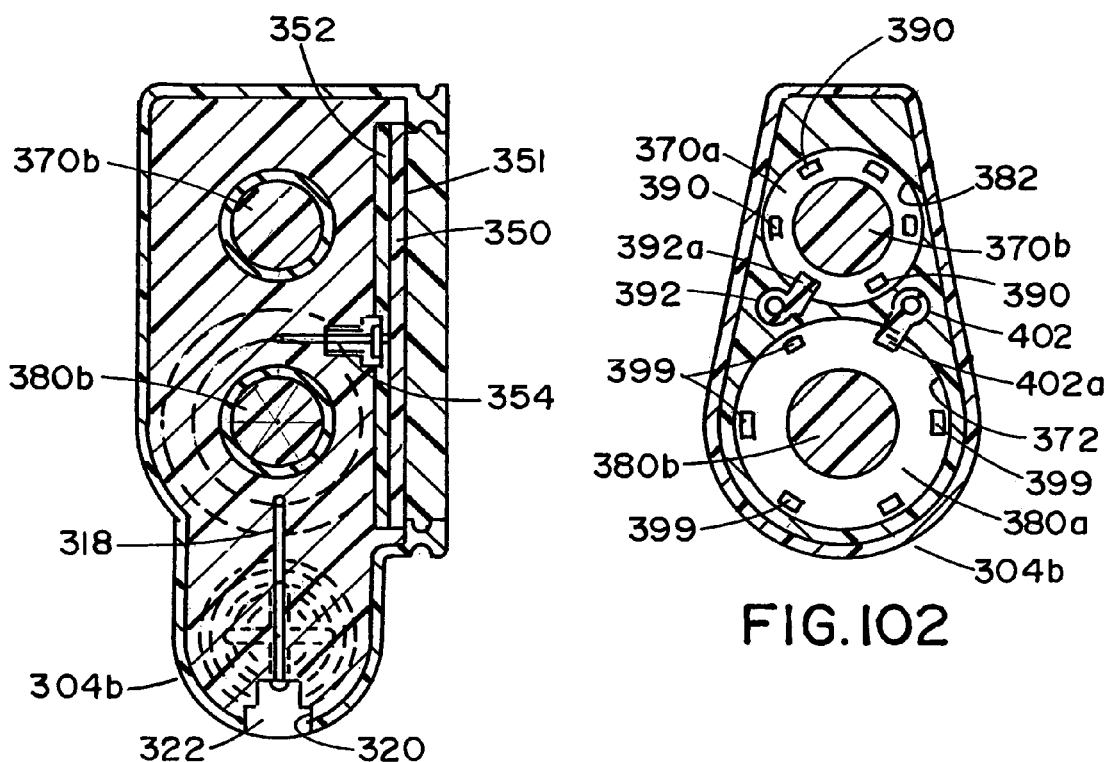
FIG.101
FIG.102
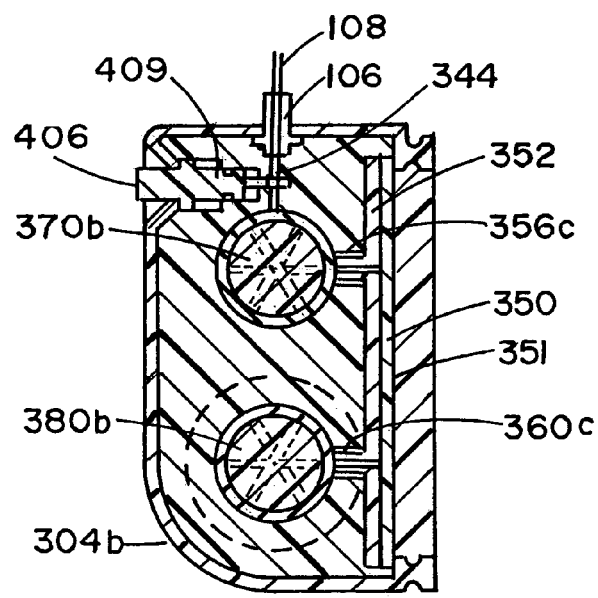
FIG.103

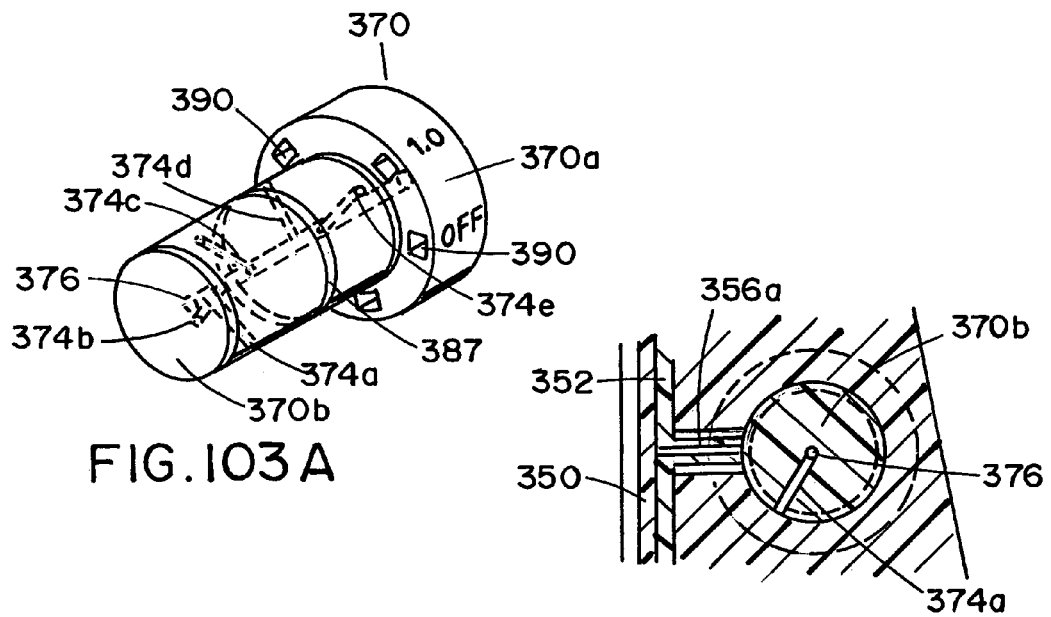
FIG. 103A
FIG. 103B
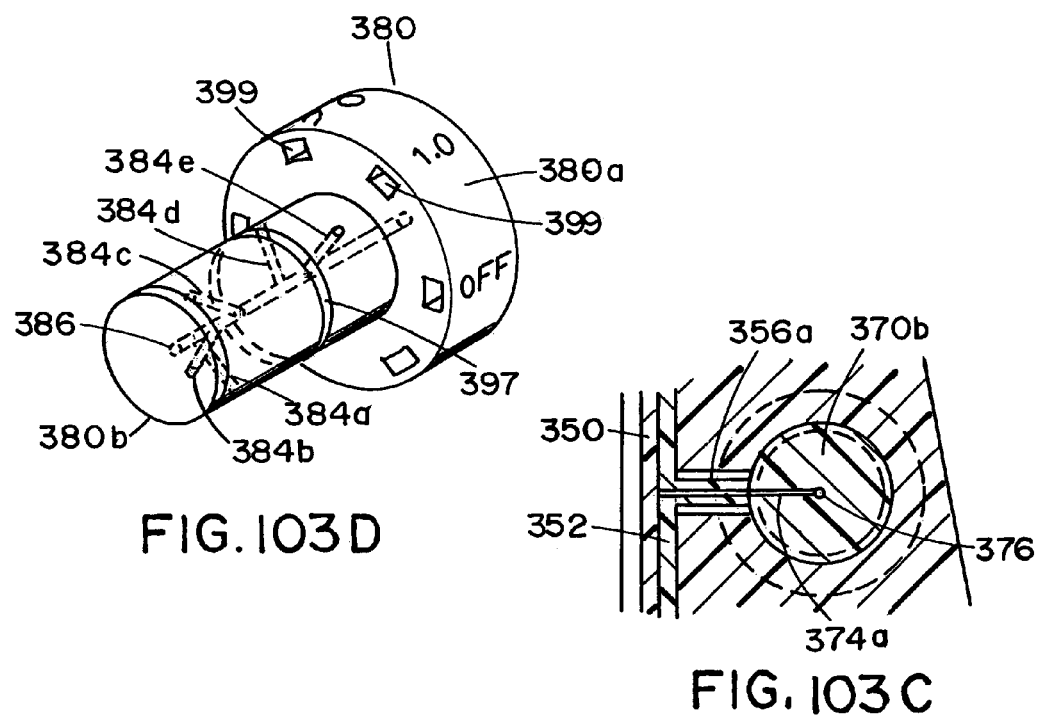
FIG. 103D
FIG. 103C

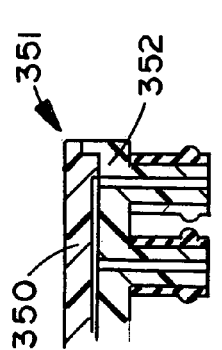
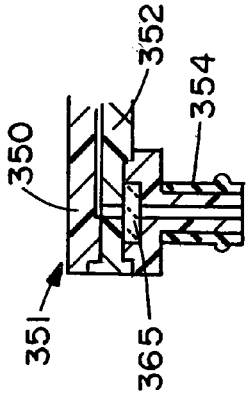
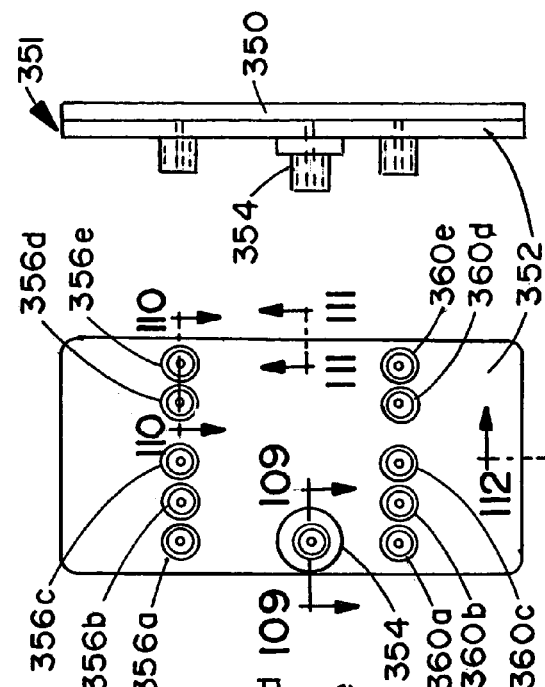
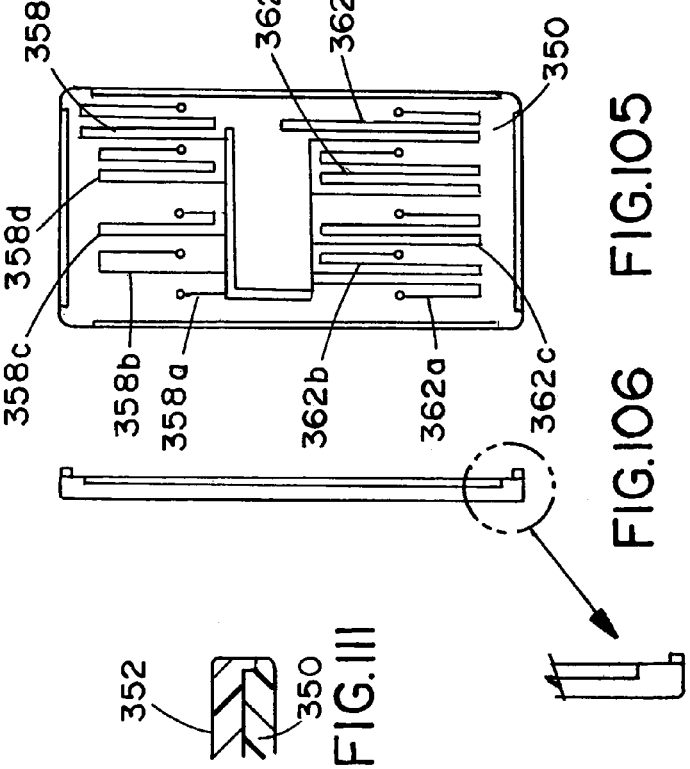

FLUID DELIVERY APPARATUS WITH ADJUSTABLE FLOW RATE CONTROL

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time, which includes a novel adjustable flow rate control means for precisely adjustably controlling the rate of fluid flow from the reservoir of the device toward the patient.

2. Discussion of the Prior Art

Many medicinal agents require an intravenous route for administration of the medicament. The delivery device for delivering the medicament, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus. Devices from which liquid is expelled from a relatively thick-walled bladder by internal stresses within the distended bladder are well known in the prior art. Such bladder, or "balloon" type, devices are described in U.S. Pat. No. 3,469,578, issued to Bierman and in U.S. Pat. No. 4,318,400, issued to Perry.

One of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs biopharmaceuticals, and the like from a prefilled container at a uniform rate. The dispenser, which is quite dissimilar in construction and operation from that of the present invention, includes a stored energy source in the form of a compressively deformable, polymeric elastomeric member that provides the force necessary to controllably discharge the medicament from a prefilled container, which is housed within the body of the device. After having been deformed, the polymeric, elastomeric member will return to its starting configuration in a highly predictable manner.

Another important prior art fluid delivery device is described in the U.S. Pat. No. 6,063,059 also issued to one of the present inventors. This device, while being of a completely different construction embodies a compressible-expandable stored energy source somewhat similar to that used in the apparatus of the present invention.

As will be appreciated from the discussion, which follows, the apparatus of the present invention is uniquely suited to provide precise, continuous fluid delivery management at a low cost in those cases where a variety of precise dosage schemes are of utmost importance. An important aspect of the apparatus of the present invention is the provision a novel, rotatable fluid flow rate control means that includes uniquely formed micro capillary, multichannel flow rate control channels which enable precise control of the rate of fluid flow of the medicament to the patient. More particularly, the apparatus of the present invention includes a novel, adjustable fluid flow rate mechanism which enables the fluid contained within the reservoir of the device to be precisely dispensed at various selected rates.

The apparatus of the present invention can be used with minimal professional assistance in an alternate health care environment, such as the home. By way of example, devices of the invention can be comfortably and conveniently removably affixed to the patient's body or clothing and can be used for the continuous infusion of antibiotics, such as, for example, an antibiotic sold by Abbott Laboratories under the name and style ANCIF and by Rosche under the name and style ROCEPHIN, analgesics, such as morphine and like medicinal agents.

By way of summary, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a compressible-expandable spring member that provides the force necessary to substantially, uniformly dispense various solutions from the device reservoir. Because of the simplicity of construction of the apparatus of the invention, and the straightforward nature of the energy source, the apparatus can be manufactured at low cost without in any way sacrificing accuracy and reliability.

SUMMARY OF THE INVENTION

It is an object of the present invention to provide a compact fluid dispenser for use in controllably dispensing fluid medicaments, such as, antibiotics, analgesics, and like medicinal agents from the device reservoir.

It is another object of the invention to provide a fluid dispenser of the aforementioned character which is highly reliable and is easy-to-use by laypersons in a non-hospital environment.

Another object of the invention is to provide a small, compact fluid dispenser that includes novel fill means for filling the dispenser reservoir with the medicament to be dispensed.

Another object of the invention is to provide an apparatus which can be factory prefilled with a wide variety of medicinal fluids or one which can readily be filled in the field shortly prior to use.

Another object of the invention is to provide a dispenser of in which a stored energy source is provided in the form of a constant force spring member of novel design that provides the force necessary to continuously and substantially uniformly expel fluid from the device reservoir.

Another object of the invention is to provide a device of the aforementioned character which includes novel adjustable flow rate control means disposed intermediate the fluid reservoir outlet and the outlet port of the device for precisely controlling the rate of fluid flow from the outlet port toward the patient.

Another object of the invention is to provide a dispenser that includes precise variable flow rate selection.

Another object of the invention is to provide a fluid dispenser of the class described which is compact, lightweight, is easy for ambulatory patients to use, is fully disposable, and is extremely accurate so as to enable the infusion of precise doses of medicament over prescribed periods of time.

Another object of the invention is to provide a device of the character described which embodies a novel fluid volume indicator that provides a readily discernible visual indication of the volume of fluid remaining in the device reservoir.

Another object of the invention is to provide a self-contained medicament dispenser which is of very simple construction and yet extremely reliable in use.

Another object of the invention is to provide a fluid dispenser as described in the preceding paragraphs which is easy and inexpensive to manufacture in large quantities.

BRIEF DESCRIPTION OF THE DRAWINGS

FIG. 1 is a generally perspective, bottom view of one form of the fluid dispensing device of the present invention.

FIG. 2 is a generally perspective, top view of the fluid-dispensing device shown in FIG. 1.

FIG. 3 is a side elevational view of the fluid dispensing device shown in FIG. 2.

FIG. 4 is a top plan view of the fluid dispensing device shown in FIG. 2.

FIG. 5 is an end view of the fluid dispensing device shown in FIG. 2.

FIG. 6 is an enlarged, cross-sectional view taken along lines 6-6 of FIG. 3.

FIG. 7 is a cross-sectional view taken along lines 7-7 of FIG. 6.

FIG. 14 is a generally perspective exploded view of one form of the reservoir fill means, or filling syringe assembly of the invention.

FIG. 16A is a fragmentary cross-sectional view of the bayonet like connector portion of the syringe assembly shall in threadably interconnected with the pusher member portion of the syringe assembly.

FIG. 16B is a view taken along lines 16B-16B of FIG. 16A.

FIG. 17 is an exploded, cross-sectional view of the fill syringe assembly in an operating configuration and the medicament containing vial assembly of one form of the invention that is to be mated with the syringe assembly.

FIG. 18 is a cross-sectional view, similar to FIG. 17, but showing the vial assembly mated with the syringe assembly.

FIG. 19A is a longitudinal cross-sectional view illustrating the fill syringe assembly shown in FIG. 18 mated with an alternate form of the fluid delivery device of the invention.

FIG. 19B is a view taken along lines 19B-19B of FIG. 19A.

FIG. 19C is a longitudinal cross-sectional view similar to FIG. 19A, but showing the reservoir of the alternate form of the fluid delivery device filled by the fill syringe assembly.

FIG. 19D is a view taken along lines 19D-19D of FIG. 19C.

FIG. 20 is a top view of one form of the flow control subassembly of the device of the invention.

FIG. 21 is a side elevational view of the flow control subassembly shown in FIG. 20.

FIG. 22 is a view taken along lines 22-22 of FIG. 21.

FIG. 23 is a cross-sectional view taken along lines 23-23 of FIG. 20.

FIG. 24 is a cross-sectional view taken along lines 24-24 of FIG. 20.

FIG. 25 is a cross-sectional view taken along lines 25-25 of FIG. 20.

FIG. 26 is a side elevational view of one form of the rate control assembly of the present invention.

FIG. 27 is a view taken along lines 27-27 of FIG. 26.

FIG. 28 is a side elevational view of one form of the multiple micro channel rate control plate of the rate control assembly of the invention.

FIG. 29 is a view taken along lines 29-29 of FIG. 28.

FIG. 34 is a generally perspective illustrative view of a portion of the fluid delivery device of the invention showing the fluid flow path during the fluid delivery step.

FIG. 35 is a fragmentary, top plan view of the front housing portion of the fluid delivery device of the invention better showing the fluid rate control subassembly.

FIG. 36 is a fragmentary, side elevational view of the front housing portion of the fluid delivery device of the invention better showing the fluid rate control subassembly.

FIG. 37 is a view taken along lines 37-37 of FIG. 36.

FIG. 45 is a top plan view of the fluid-dispensing device shown in FIG. 44.

FIG. 46 is a side elevational view of the fluid dispensing device shown in FIG. 44.

FIG. 47 is a view taken along lines 47-47 of FIG. 46.

FIG. 48 is a view taken along lines 48-48 of FIG. 46.

FIG. 49 is a side elevation view of the fluid dispensing device shown in FIG. 46.

FIG. 67 is a side elevational view of the flow control housing of this latest form of the fluid delivery device of the invention.

FIG. 68 is a view taken along lines 68-68 of FIG. 67.

FIG. 69 is a view taken along lines 69-69 of FIG. 67.

FIG. 70 is a side elevational view of the main housing and the flow control housing of this latest form of the fluid delivery device of the invention.

FIG. 71 is a view taken along lines 71-71 of FIG. 70.

FIG. 72 is a view taken along lines 72-72 of FIG. 70.

FIG. 76 is a side elevational, cross-sectional view of the selector knob assembly of the flow control assembly of this latest form of the invention.

FIG. 77 is a side elevational, cross-sectional view of the selector knob of the flow control assembly of this latest form of the invention.

FIG. 78 is a view taken along lines 78-78 of FIG. 77.

FIG. 79 is an end view of the control knob of the flow control assembly of this latest form of the invention.

FIG. 80 is a cross-sectional view taken along lines 80-80 of FIG. 79.

FIG. 81 is a view taken along lines 81-81 of FIG. 80.

FIG. 82 is an end view of the cover component of the rate control assembly of this latest form of the invention.

FIG. 83 is a side elevational view of the inner face of the cover member of the rate control assembly of the invention.

FIG. 84 is a side elevational view of the outer face of the cover member of the rate control assembly of the invention.

FIG. 85 is a view taken along lines 85-85 of FIG. 84.

FIG. 86 is an end view of base plate, or rate control member of the rate control assembly of the invention.

FIG. 87 is a side elevational view of the base plate, or rate control member of the rate control assembly of the invention.

FIG. 89 is a cross-sectional view, similar to FIG. 52, but showing the reservoir of the device in a filled condition.

FIG. 90 is a cross-sectional view taken along lines 90-90 of FIG. 89.

FIG. 91 is a generally perspective illustrative view of a portion of the fluid delivery device of this latest form of the invention showing the fluid flow path during the reservoir fill step.

FIG. 92 is a generally perspective illustrative view of a portion of the fluid delivery device of this latest form of the invention showing the fluid flow path during the fluid delivery step.

FIG. 95 is a rear view of the fluid-dispensing device shown in FIGS. 93 and 94.

FIG. 96 is a front view of the fluid-dispensing device shown in FIGS. 93 and 94.

FIG. 97 is a view taken along lines 97- 97 of FIG. 96.

FIG. 98 is a side view of one of the locking arms of the device.

FIG. 99A is a generally perspective, exploded view of the rear portion of the fluid dispensing device shown in FIG. 93.

FIG. 101 is a cross-sectional view taken along lines 101-101 of FIG. 99.

FIG. 102 is a cross-sectional view taken along lines 102-102 of FIG. 99.

FIG. 103 is a cross-sectional view taken along lines 103-103 of FIG. 99.

FIG. 103A is a generally perspective view of the micro rate selector knob assembly.

FIG. 103B is a fragmentary cross-sectional view of a portion of the flow rate control means of the invention showing the micro rate selector knob assembly in an off condition.

FIG. 103C is a fragmentary cross-sectional view of a portion of the flow rate control means of the invention showing the micro rate selector knob assembly in a delivery condition.

FIG. 103D is an end view of the macro rate selector knob assembly of the fluid dispensing device.

FIG. 105 is a side elevational view of the inner face of the cover member of the rate control assembly of this latest form of the invention.

FIG. 106 is an end view of the cover member shown in FIG. 105.

FIG. 106A is an enlarged, fragmentary view of the portion identified in FIG. 106 as "106A".

FIG. 107 is a side elevational view of the outer face of the cover member of the rate control assembly of the invention.

FIG. 108 is an end view of the flow rate control assembly of this latest form of the fluid delivery device of the invention.

FIG. 109 is a view taken along lines 109-109 of FIG. 107.

FIG. 110 is a view taken along lines 110-110 of FIG. 107.

FIG. 111 is a view taken along lines 111-111 of FIG. 107.

FIG. 112 is a view taken along lines 112-112 of FIG. 107.

FIG. 113 is a generally perspective illustrative view of a portion of the fluid delivery device of the invention showing the fluid flow path during the fill step.

FIG. 114 is a generally perspective illustrative view of a portion of the fluid delivery device of the invention showing the fluid flow path during the fluid delivery step.

FIG. 115 is a longitudinal cross-sectional view of still another form of the apparatus of the invention.

Figure 115:
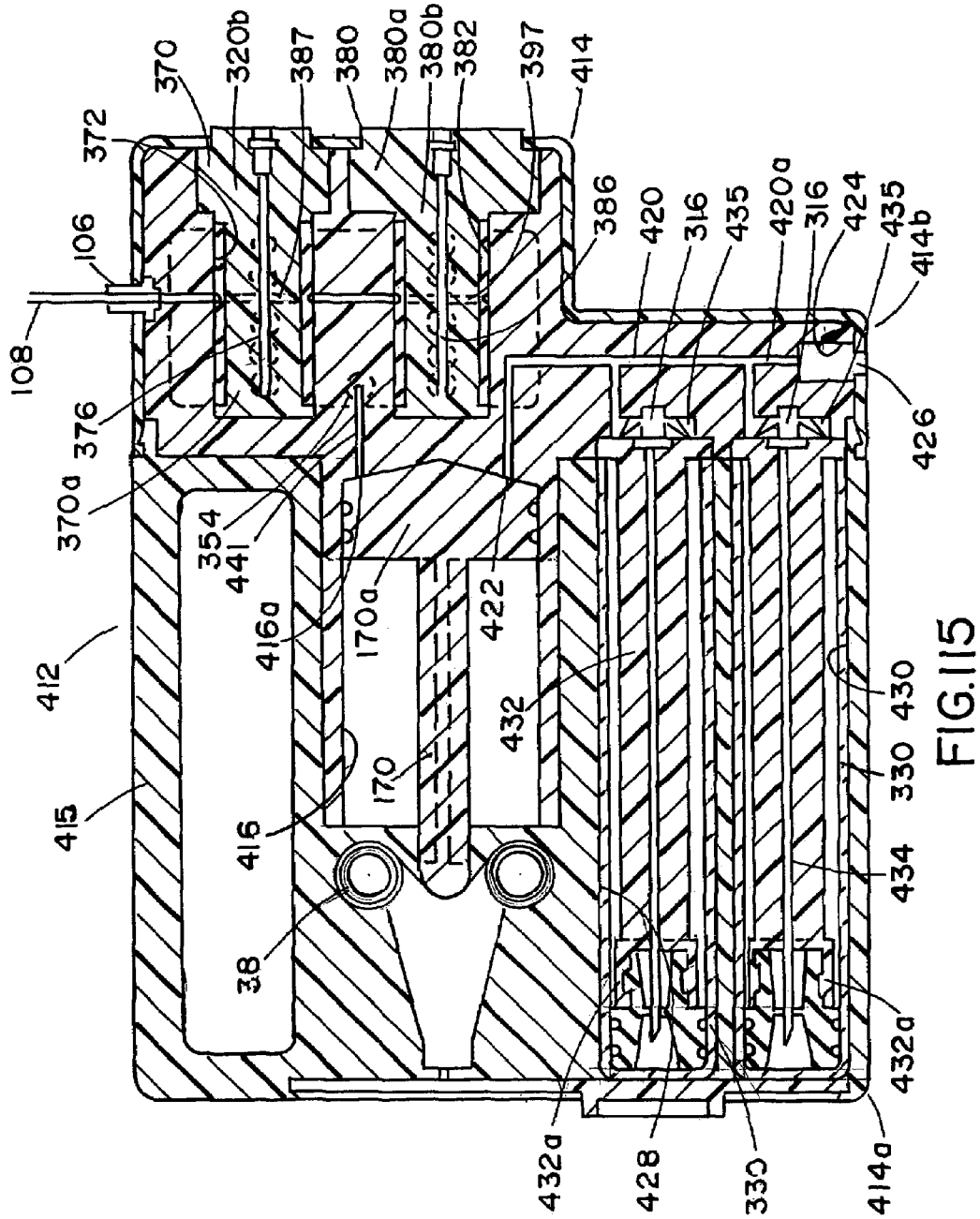
Figure 116:
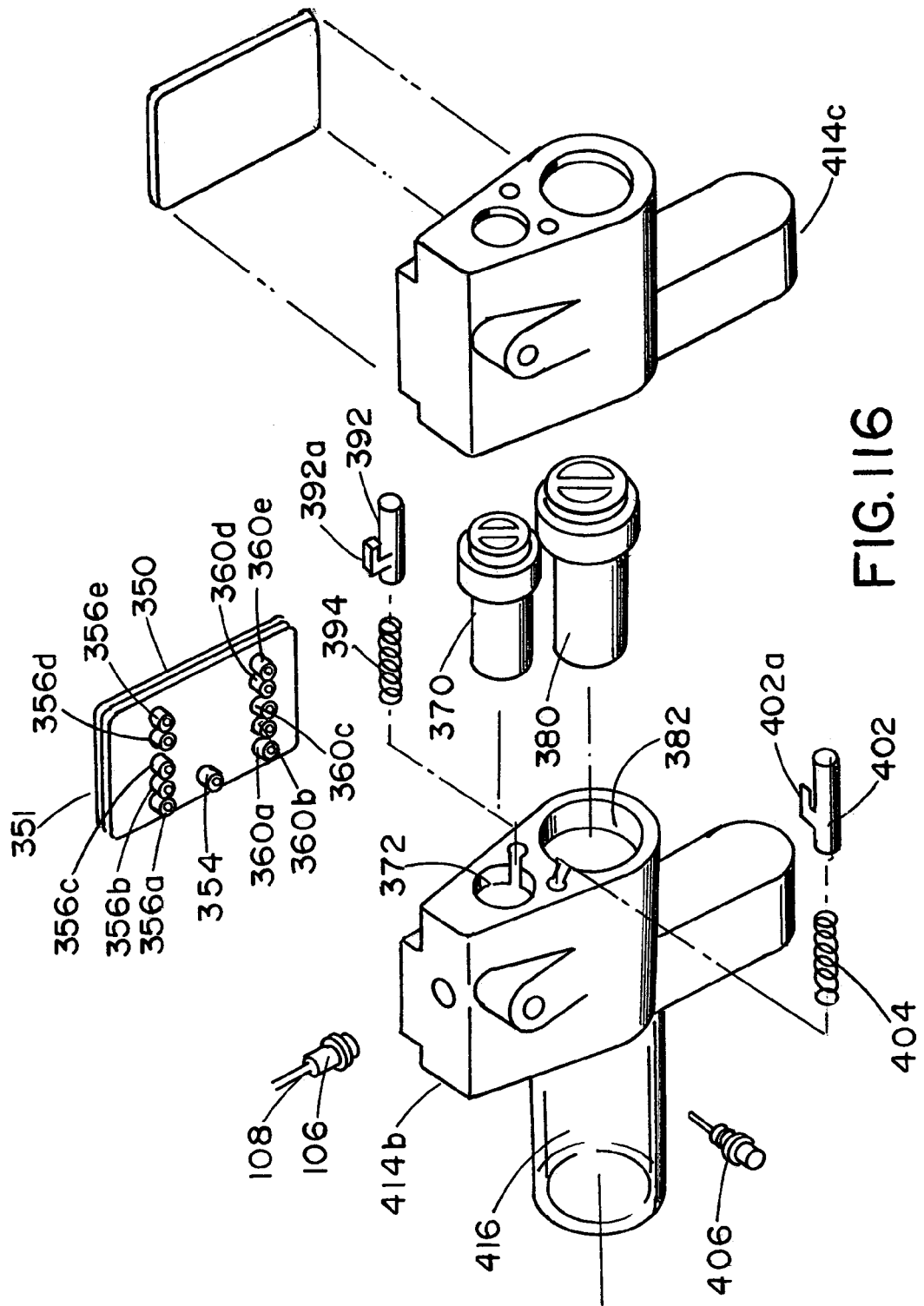
Figure 116A:
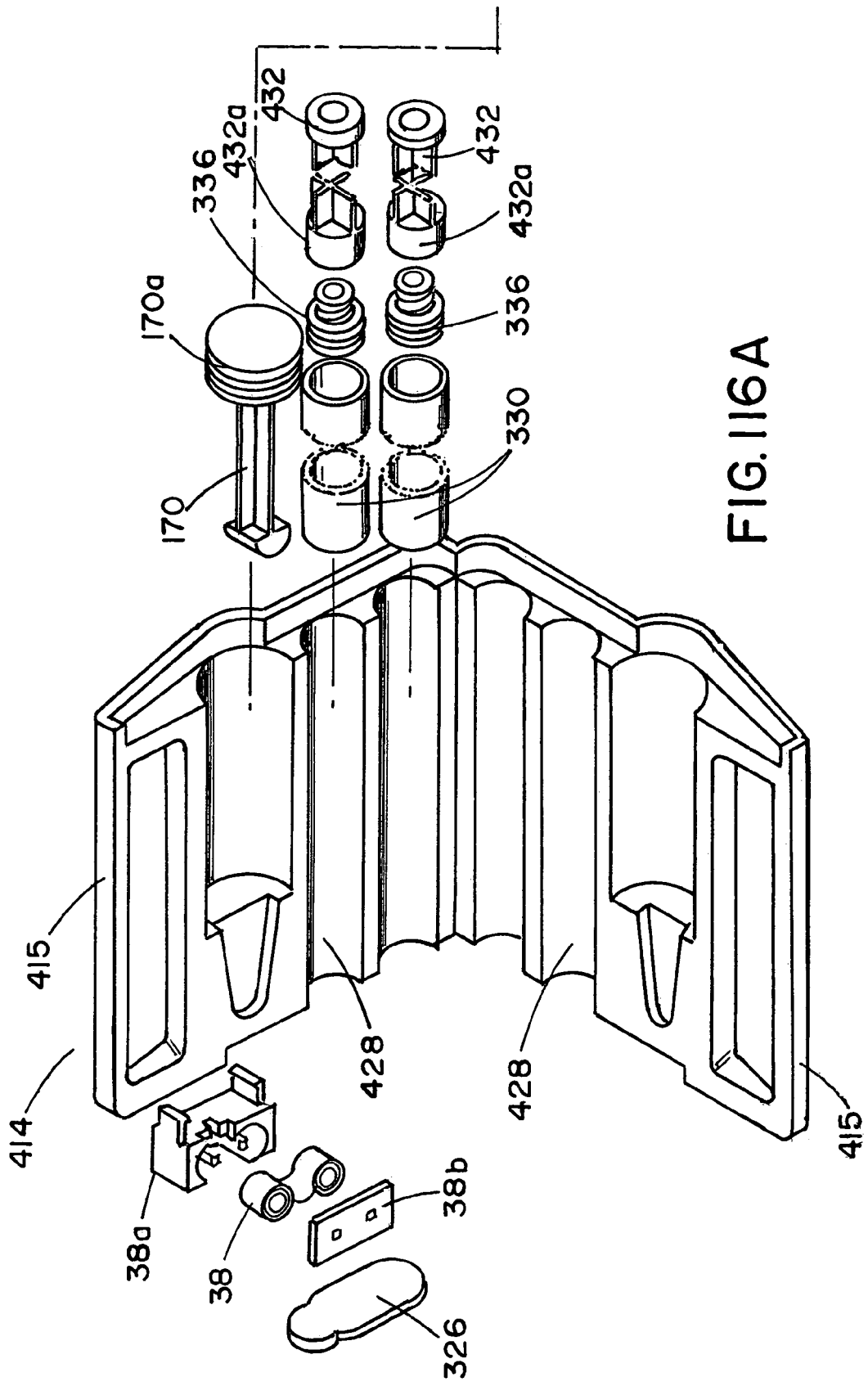

FIGS. 116 and 116A when considered together comprise a generally perspective, exploded view of the form of the delivery device of the invention illustrated in FIG. 115 (hereinafter referred to as "FIG. 116").

Figure 117:
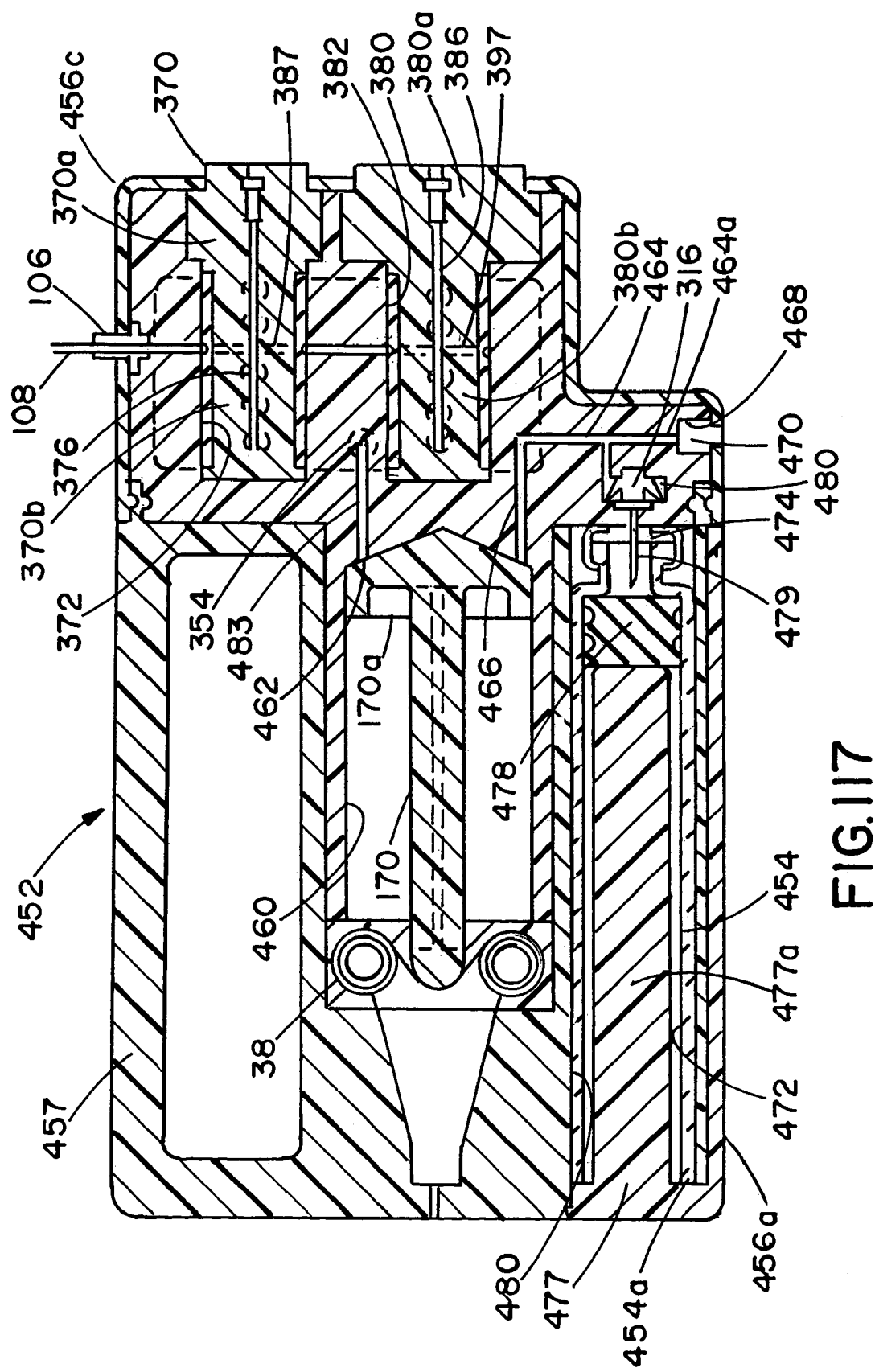

FIG. 117 is a longitudinal cross-sectional view of yet another form of the apparatus of the invention.

Figure 118:
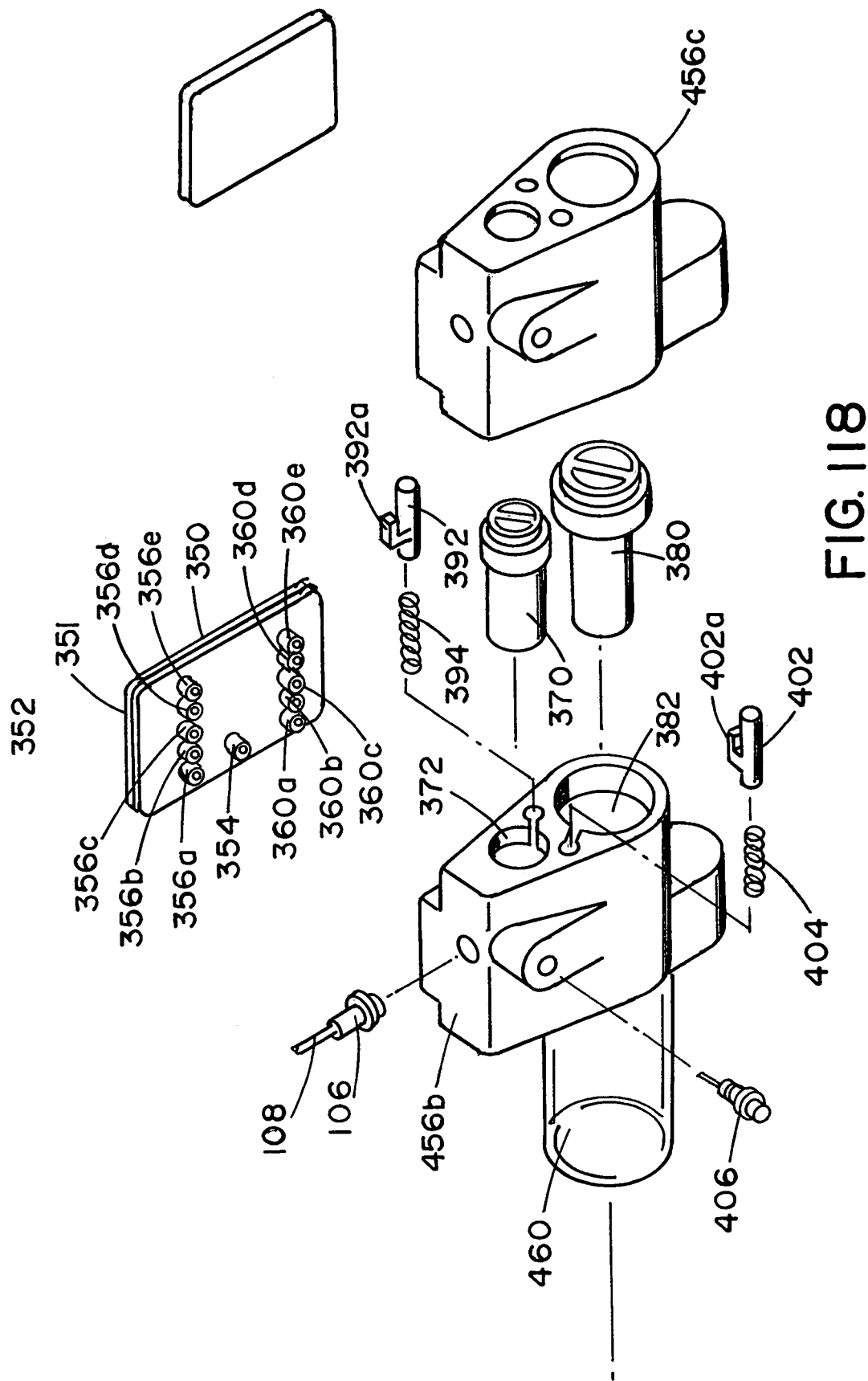
Figure 118A:
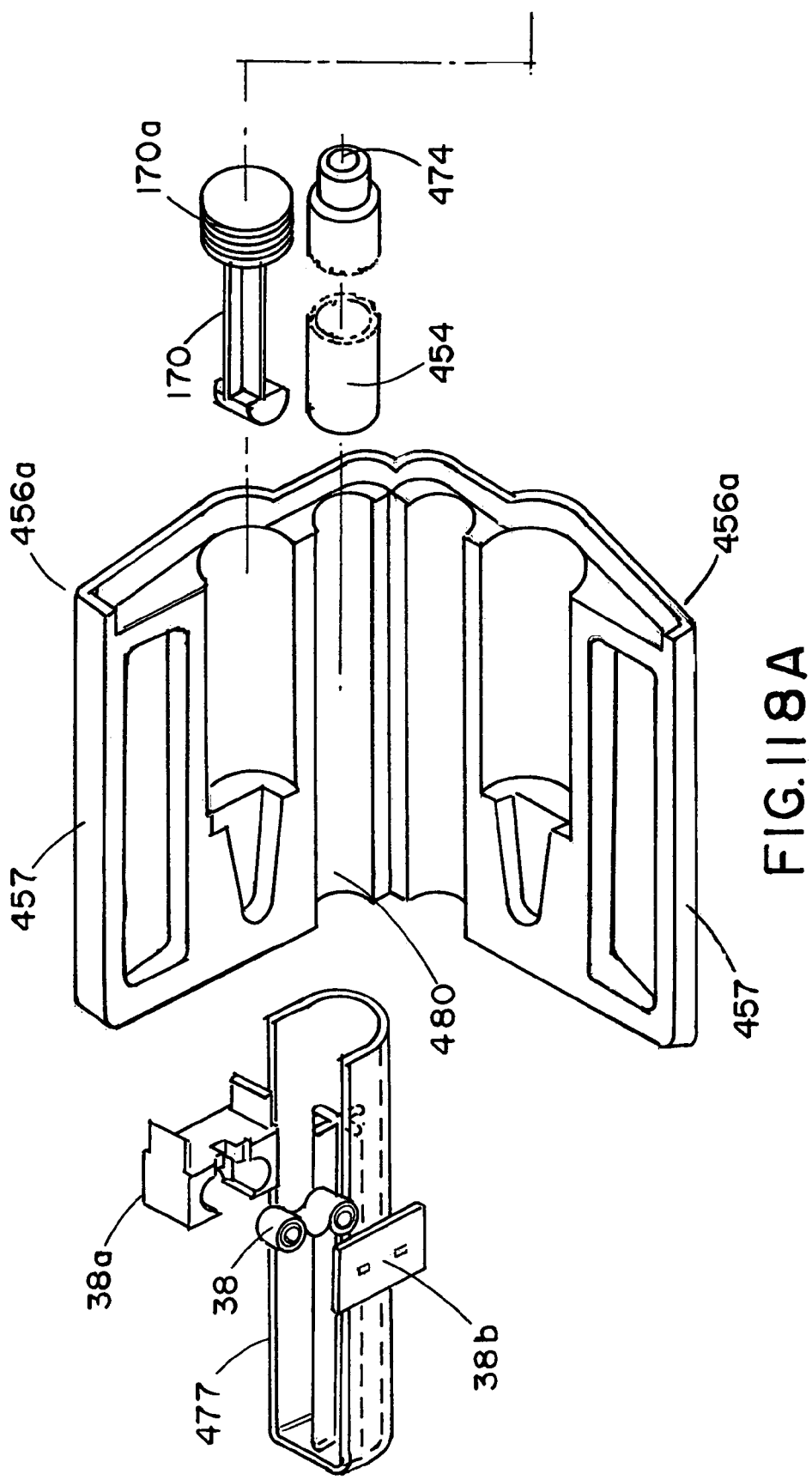

FIGS. 118 is and 118A when considered together comprise a generally perspective, exploded view of the form of the delivery device of the invention illustrated in FIG. 118 (hereinafter referred to as "FIG. 118").

Figure 119:
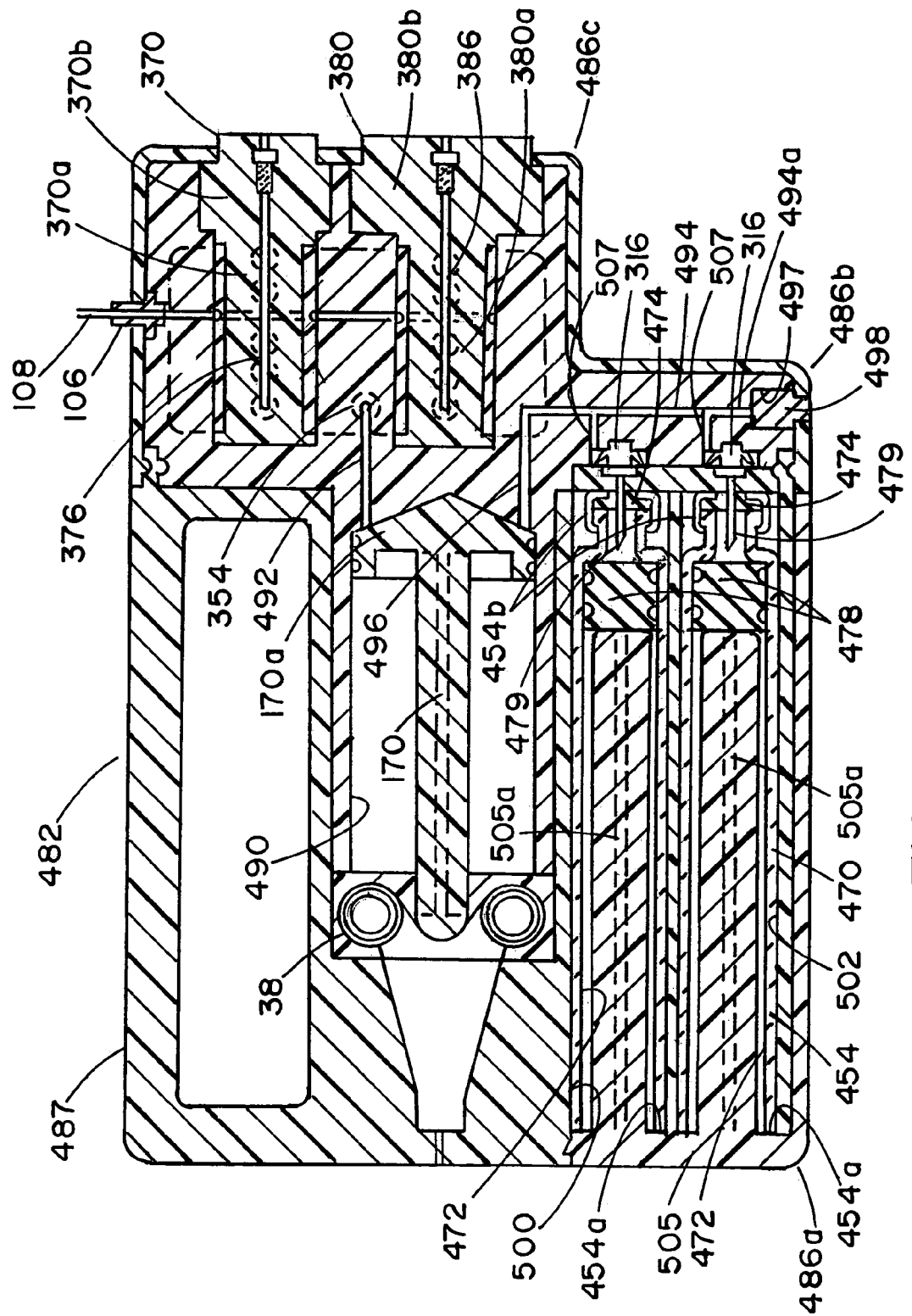

FIG. 119 is a longitudinal cross-sectional view of still another form of the apparatus of the invention.

Figure 120:
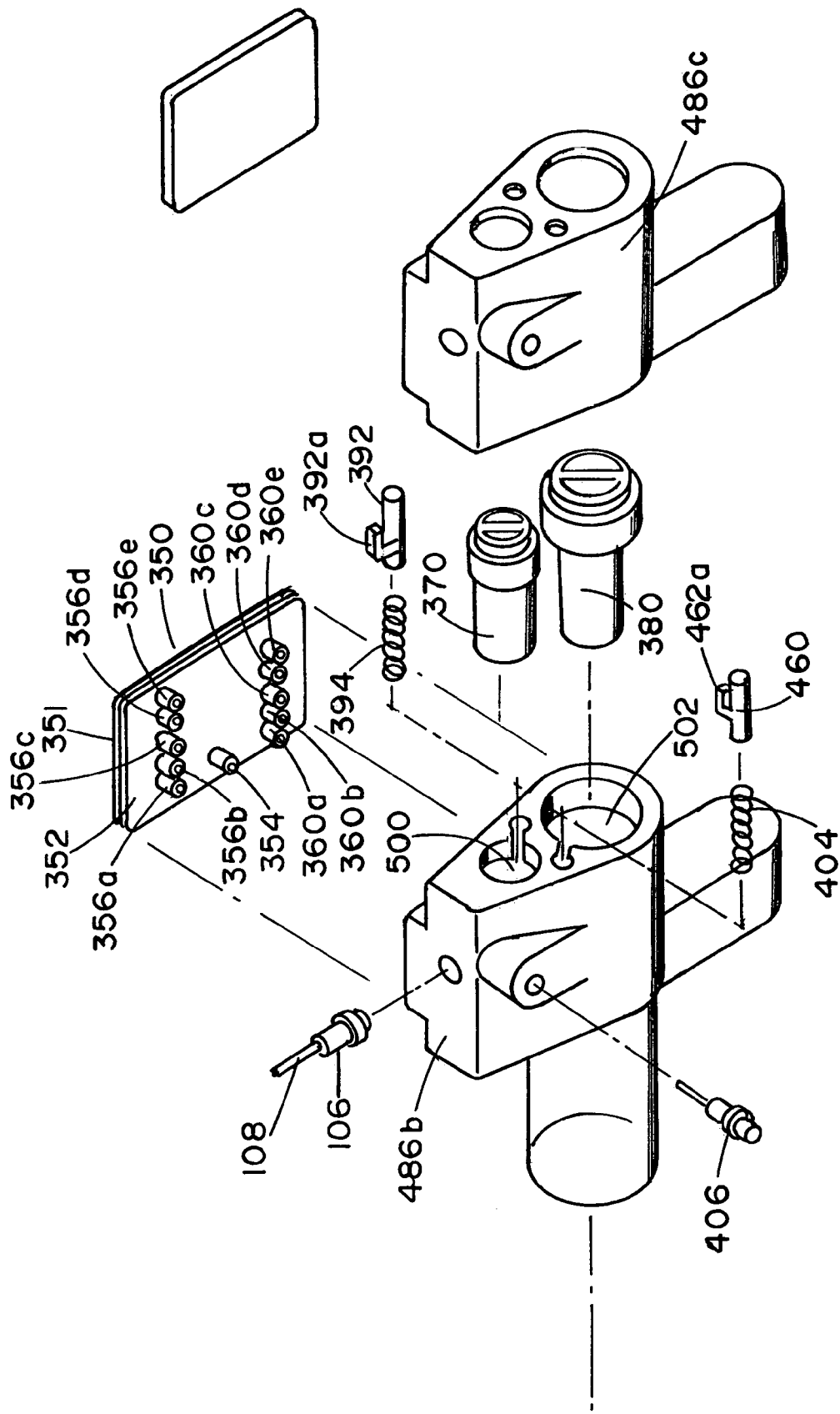
Figure 120A:
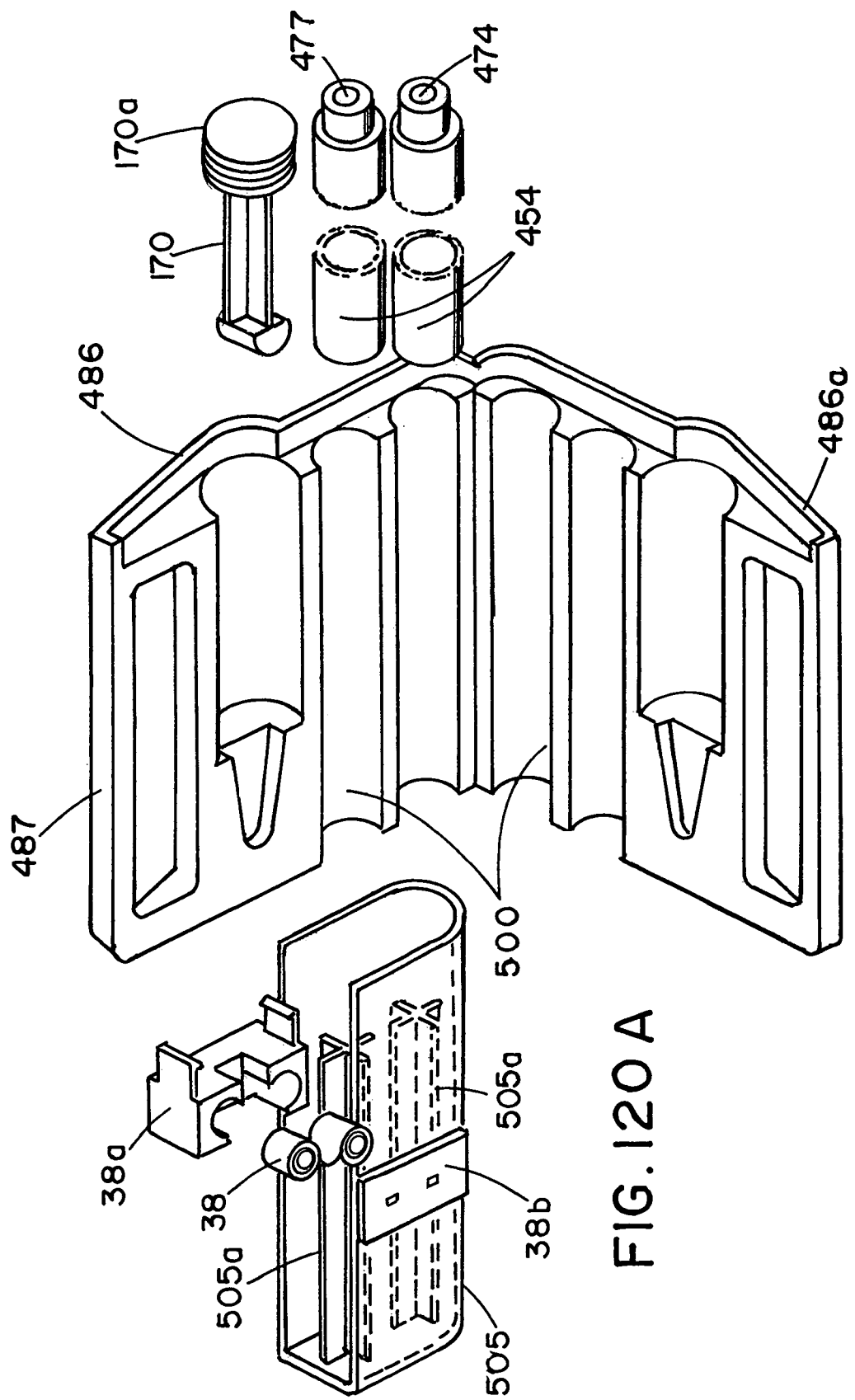

FIGS. 120 and 120A when considered together comprise a generally perspective, exploded view of the form of the delivery device of the invention illustrated in FIG. 115 (hereinafter referred to as "FIG. 120").

Figure 121:
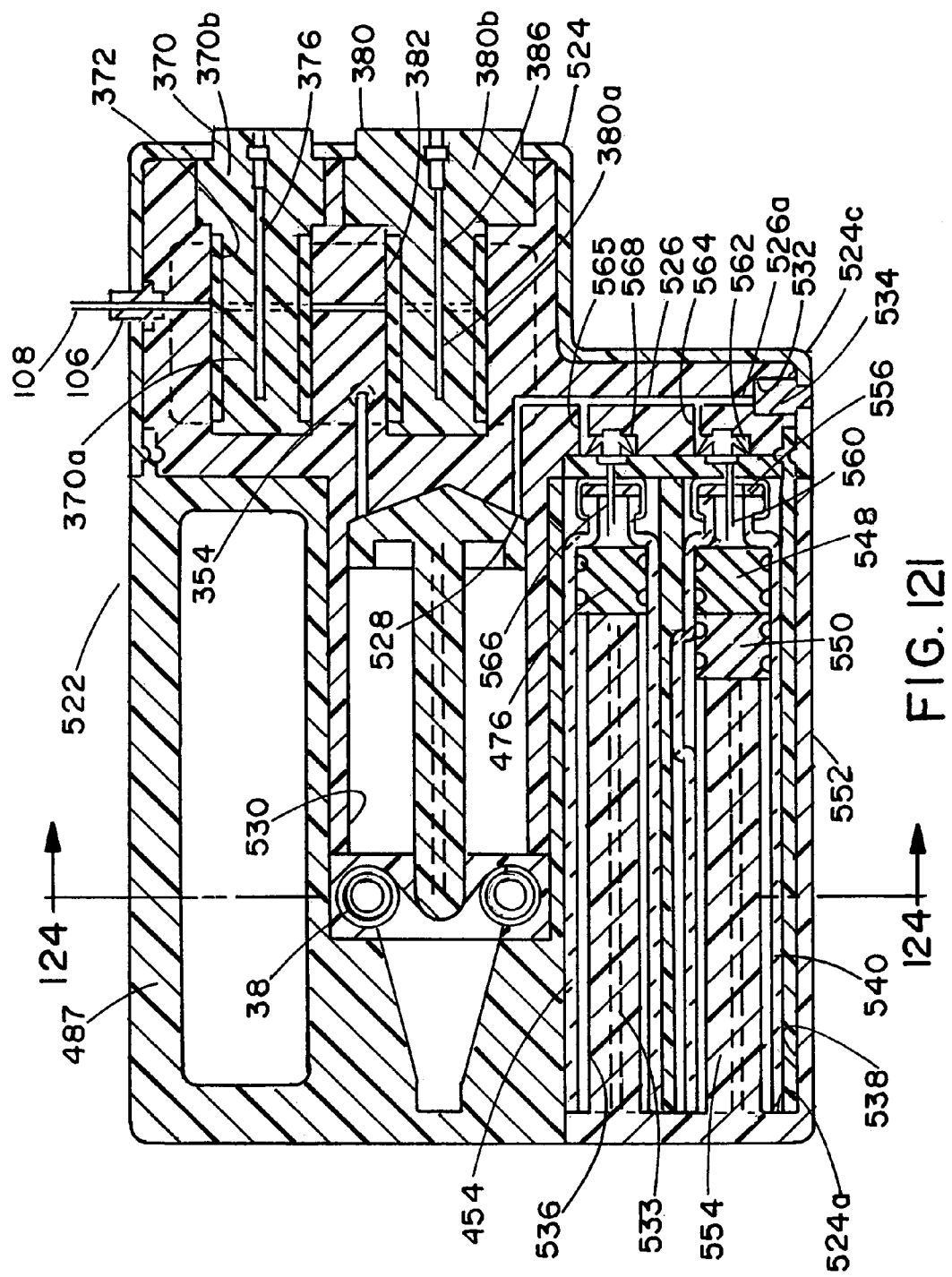

FIG. 121 is a longitudinal cross-sectional view of yet another form of the apparatus of the invention.

Figure 122:
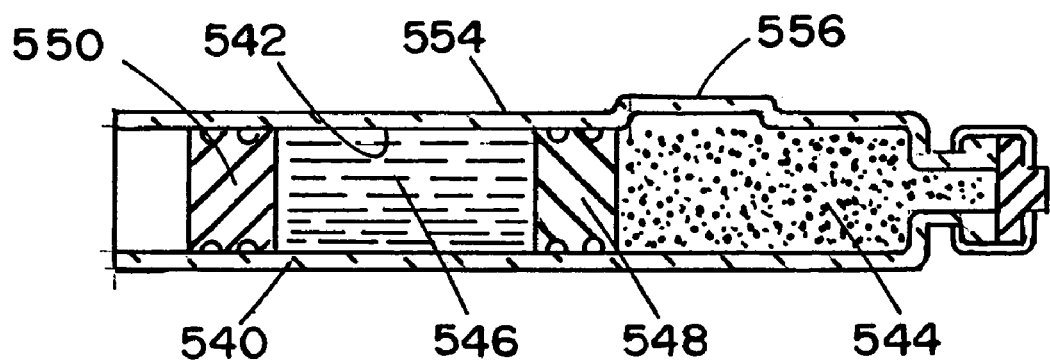

FIG. 122 is a longitudinal cross-sectional view of the lower fill vial shown in FIG. 121.

Figure 123:
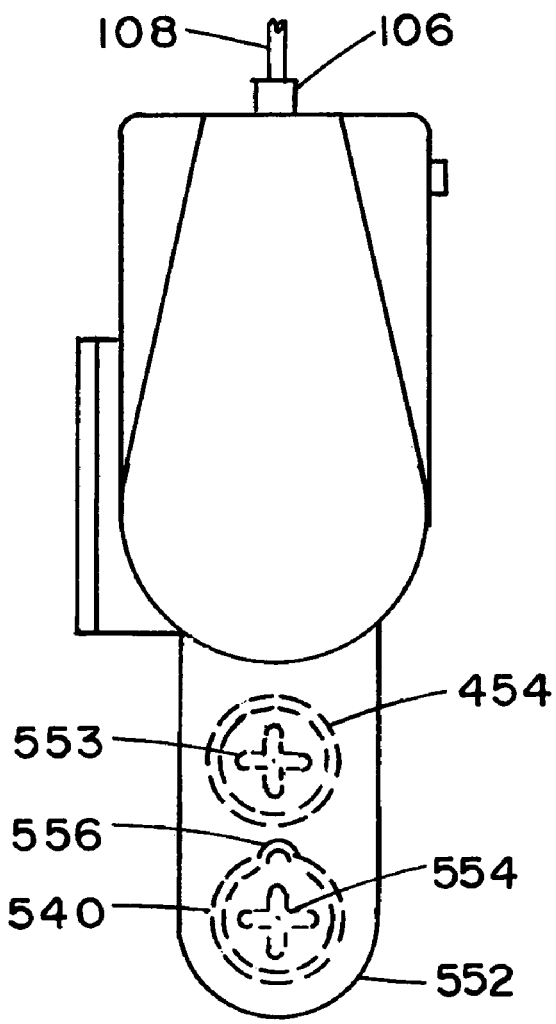

FIG. 123 is a rear view of apparatus shown in FIG. 121.

Figure 124:
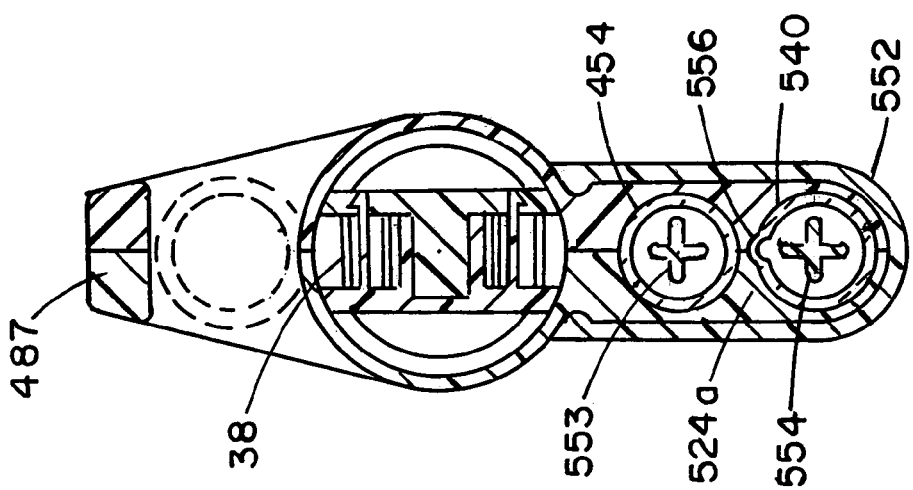

FIG. 124 is a cross-sectional view taken along lines 124-124 of FIG. 121.

Figure 125:
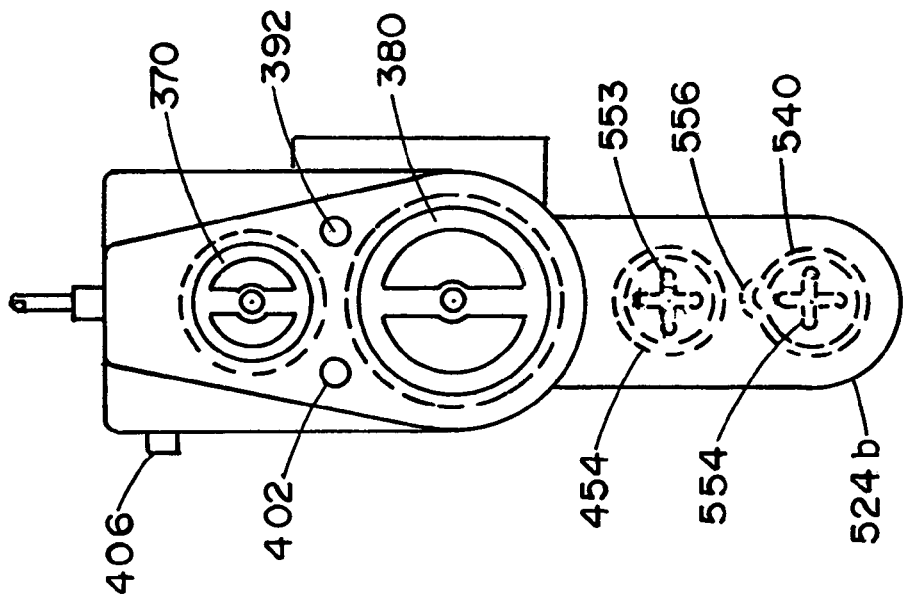

FIG. 125 is a front view of apparatus shown in FIG. 121.

Figure 126:
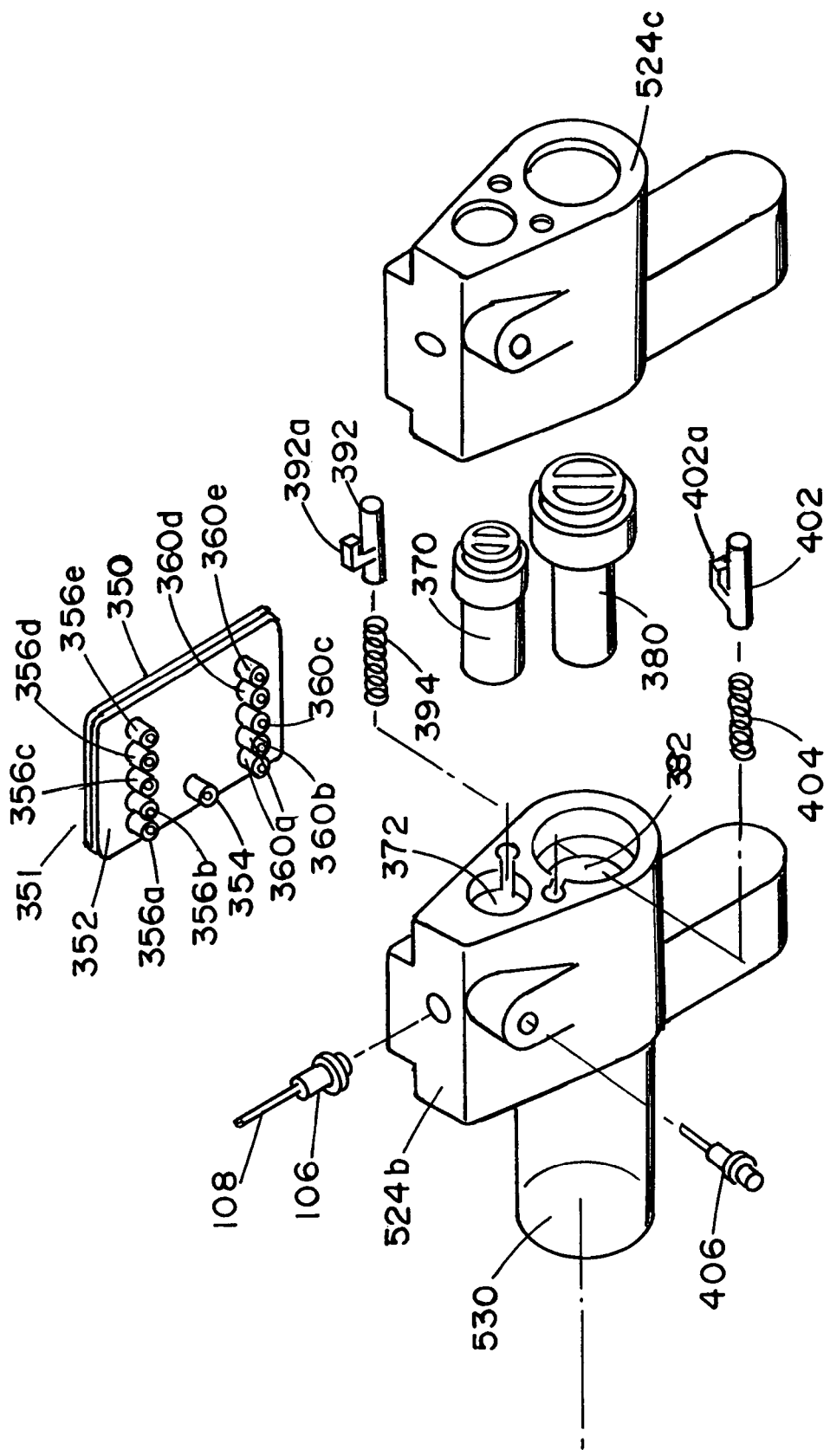
Figure 126A:
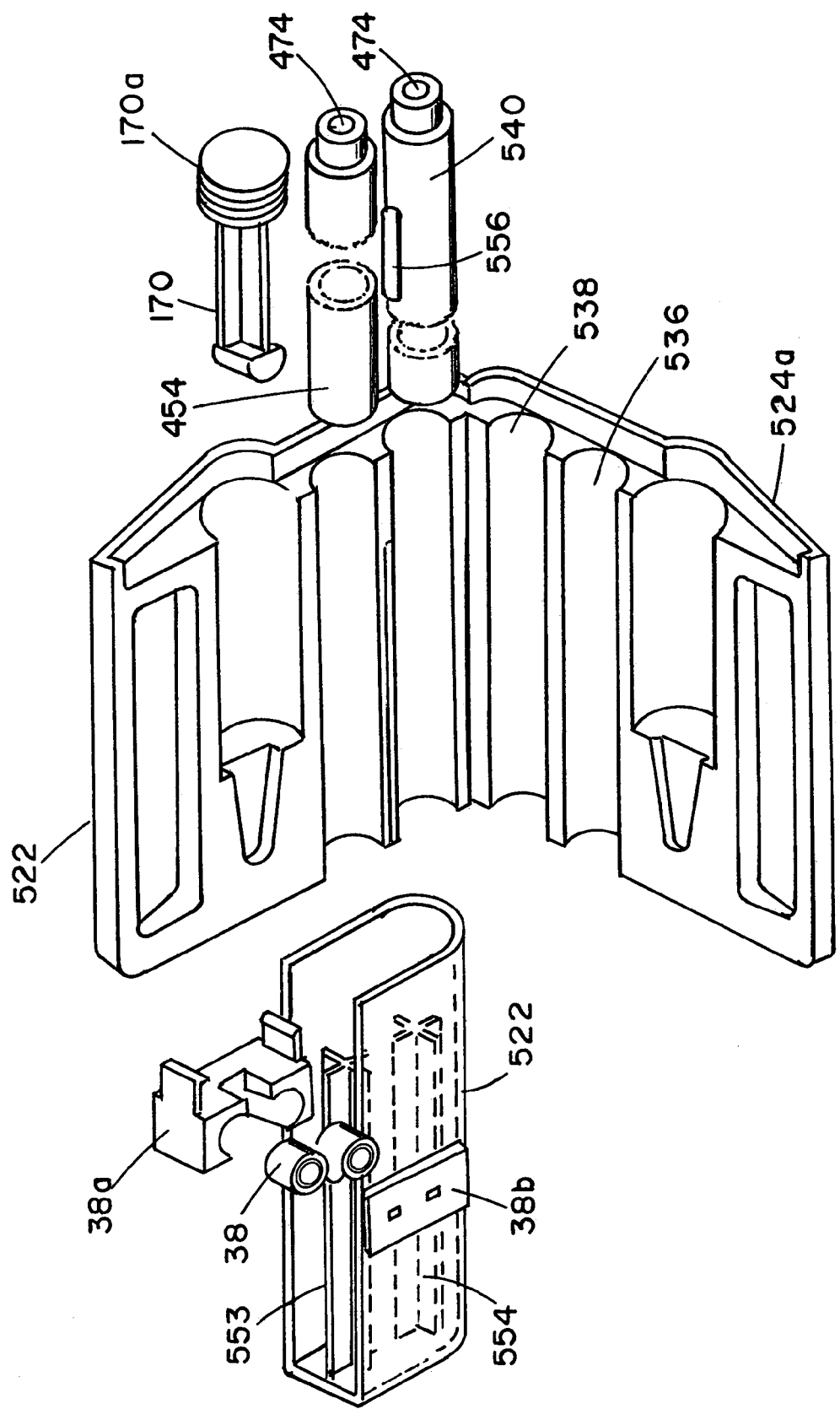

FIGS. 126 is and 126A when considered together comprise a generally perspective, exploded view of the form of the delivery device of the invention illustrated in FIG. 121 (hereinafter referred to as "FIG. 126").

DISCUSSION OF THE INVENTION

Referring to the drawings and particularly to FIGS. 1 through 7, one form of the apparatus of the present form of the invention is there illustrated and generally designated by the numeral 32. As best seen in FIGS. 2, 6 and 7, the apparatus here comprises a snap together outer housing 34 having a first, second and third portions 34a, 34b and 34c respectively. Housing portion 34a comprises the reservoir portion, housing portion 34b comprises the rate control portion and housing portion 34c comprises the fill and delivery portion.

Disposed within first portion 34a of outer housing 34 is the novel stored energy means of the invention for causing the fluid contained within fluid reservoir 36 to controllably flow outwardly of the housing and into the fluid dispensing means. In the present form of the invention, this important stored energy means comprises a constant force spring member 38 that is carried within a spring support 38a mounted within portion 34a of the outer housing. Spring member 38 is first extended in the manner shown in FIG. 12 by fluid flowing into reservoir 36 and then controllably retracts in the manner shown in FIG. 6 to cause fluid flow from the outer housing, through the dispensing means of the invention and toward the patient. Constant force spring 38, which is a special variety of extension spring, is readily commercially available from several sources including Barnes Group Inc. of Bristol, Conn., Stock Drive Products/Sterling Instrument of Hyde Park, N.Y. and Walker Corporation of Ontario, Calif. Constant force spring 38 is basically a high stress, long deflection device that offers great advantages when used in applications where very low or zero gradient is desired, where space is a factor and where very high reliability is required. Constant force springs, such as spring 38, provides markedly superior constant force loading when compared to conventional helical extension or like springs. Spring 38, which acts on a pusher member 40 of the character shown in FIGS. 6, 12 and 13, can be constructed from a wide variety of materials including stainless steel.

Figure 12:
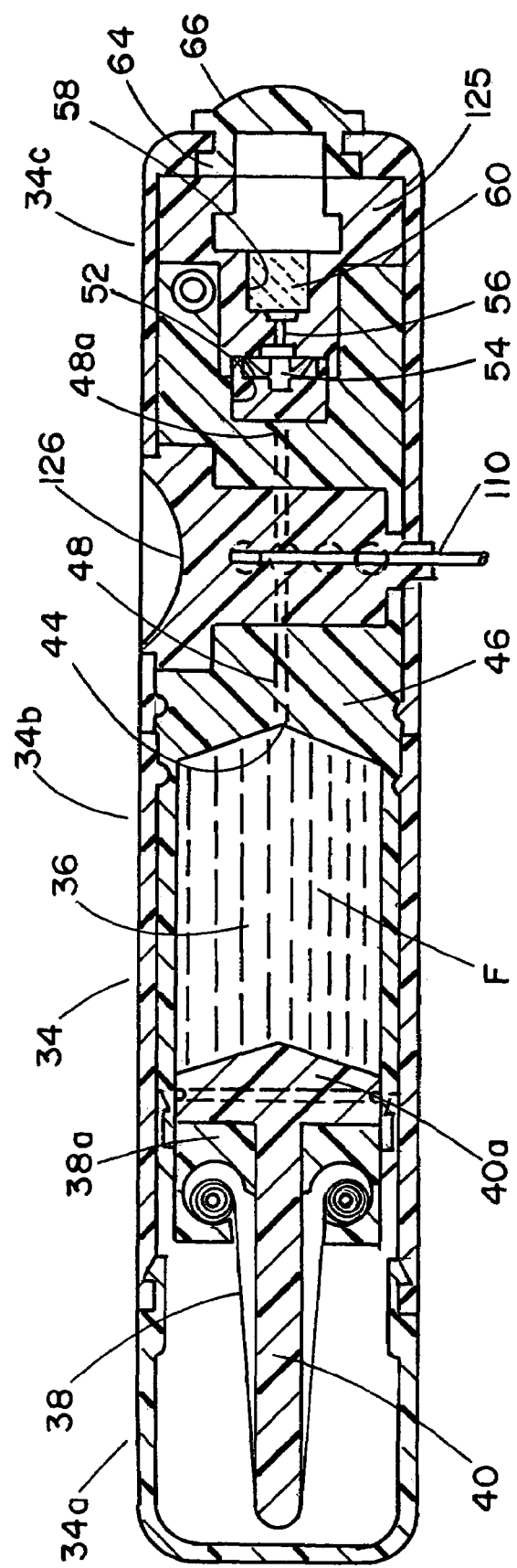
FIG. 12 is a cross-sectional view, similar to FIG. 6, but showing the reservoir of the device in a filled condition.

After the spring is extended in the manner shown in FIG. 12, it will tend to uniformly return toward its starting configuration and in so doing will exert a constant force on pusher member 40, which is housed within housing portion 34a in the manner shown in FIGS. 6, 7 and 12. As the spring returns to its starting configuration, the fluid contained within the fluid reservoir 36 will be caused to flow outwardly through outlet 44 formed in the rate control housing 46 at a substantially constant rate (FIG. 7).

Forming an important aspect of the apparatus of the present invention is fill means, which is carried by the third portion 34c of outer housing 34 for filling the reservoir 36 with the fluid to be dispensed. As best seen in FIG. 7, rate control housing 46 includes a fluid passageway 48 in communication with inlet 50 of fluid reservoir 36. Proximate its forward end 48a, fluid passageway 48 communicates with a cavity 52 formed within the third portion 34c of the housing. Disposed within cavity 52 is a conventional, umbrella type check valve 54 which permits fluid flow toward fill passageway 48, but blocks fluid flow in the opposite direction. Cavity 52 communicates, via a stub passageway 56, with a cavity 58 that houses a pierceable septum 60, which comprises a part of one form of the fill means of the invention. Septum 60 may be a conventional slit septum, the character well understood by those skilled in the art 60, which is pierceable by the cannula of a filling syringe assembly which contains the medicinal fluid to be dispensed and which, in a manner presently to be described, can be used to fill or partially fill reservoir 36 via passageway 48.

Figure 16:
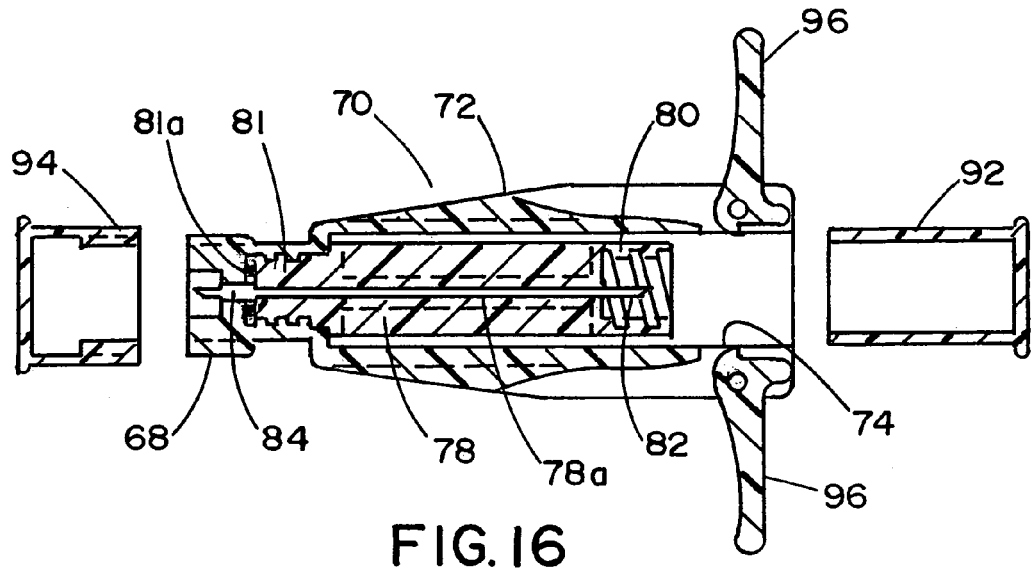
FIG. 16 is a cross-sectional view similar to FIG. 15, but showing the protective end closure caps removed and the finger-engaging wing like members extended.
Figure 15:
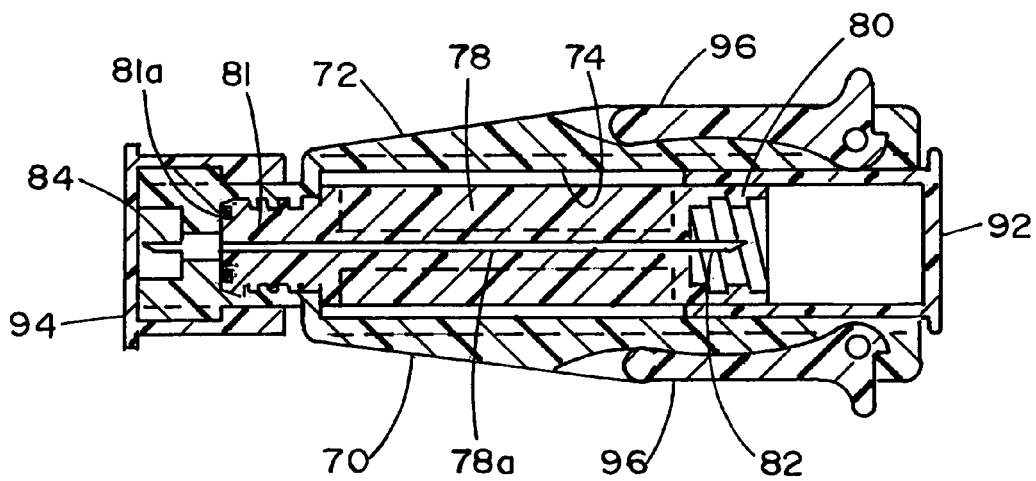
FIG. 15 is an enlarged, longitudinal cross-sectional view of the sale syringe assembly of the invention.

Third portion 34c of housing 34 includes bayonet type connector portion 64 that is normally closed by a closure cap 66 (FIGS. 6 and 7). Connector portion 64 of the housing is adapted to receive the connector portion 68 of the fill syringe assembly of the invention, which is generally designated in FIG. 14 by the numeral 70 (see also FIG. 16B). As shown in FIGS. 14, 15 and 16, the syringe fill assembly 70 includes a hollow housing 72 that is provided with a chamber 74 for telescopically receiving a medicament containing fill vial 76 (FIG. 17), the construction of which will presently be described.

An elongated support 78, which is mounted within chamber 74 of the syringe fill assembly 70, includes threaded end portions 80 and 81 and a central flow passageway 78a. Support 78 carries at one end a hollow needle 82 having a flow passageway which communicates, via passageway 78a, with the flow passageway of a second needle or cannula 84 that is carried interiorly of the syringe connector 68. Syringe connector 68 is threadably interconnected within portion 81 of support 78 by means of an O-ring 81a (FIG. 16A). Second cannula 84 is adapted to pierce septum 60 when the syringe assembly is operably interconnected with third portion 34c of housing 34 in the manner shown in FIG. 19 of the drawings. Chamber 74, elongated support 78 and hollow needles 82 and 84 comprise a part of the fill means of the apparatus of the invention.

Referring particularly to FIG. 17, the medicament containing fill vial 76 includes a body portion 76a, having a fluid chamber 88 for containing the injectable fluid medicament. Chamber 88 is provided with a first open end 88a and second closed end 88b. First open end 88a is sealably closed by closure means here provided in the form of an externally threaded elastomeric plunger 90 which is telescopically movable within chamber 88 from a first location where the plunger is disposed proximate first open end 88a to the second, device-fill location where the plinger is disposed proximate second closed end 88b.

After removal of a closure member 92 from the syringe assembly in the manner shown in FIG. 16, vial 76 can be inserted into chamber 74 (FIGS. 17 and 18). As the fill vial is so introduced and the plunger 90 is threadably interconnected with threaded end 80 of support 78, the sharp end of the elongated needle 82 will pierce the central wall 90a of the elastomeric plunger in the manner shown in FIG. 18. Following removal of cover member 94 which covers connector portion 68 of the syringe assembly (FIG. 16), the assembly shown in FIG. 18 of the drawings can be mated with the fluid dispenser in the manner shown in FIG. 19. This done, the gripping fingers 96 can be retracted from the retracted position shown in FIG. 15 to the extended position shown in FIG. 16.

Figure 19:
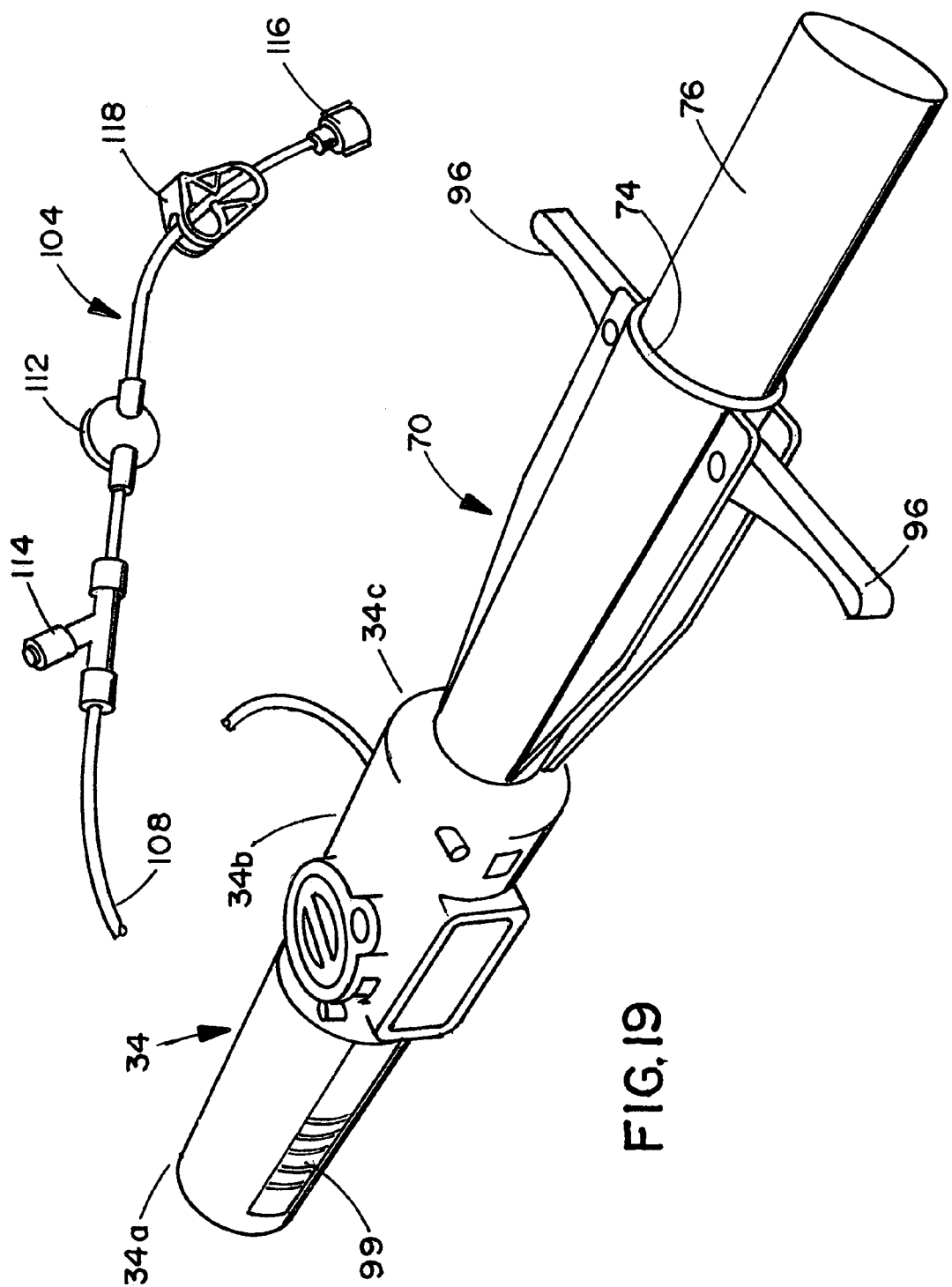
FIG. 19 is a generally perspective view illustrating the fill syringe assembly shown in FIG. 18 mated with the fluid delivery device of the invention.

With the syringe fill assembly of the invention mated with the fluid dispenser in the manner of shown in FIG. 19, the caregiver can grip the fingers 96 with his or her fingers and can exert an inward pressure on vial 76 causing the vial to move inwardly of chamber 74. A continuous movement of the vial into chamber 74 will cause the structural support 78 to move the elastomeric plunger inwardly of the vial chamber 88 in a direction toward the second or closed end 88b of the vial chamber. As the plunger is moved inwardly of the vial, the fluid "F" (FIG. 12) contained within the vial chamber will be expelled there from into the hollow elongated needle 82. The fluid will then flow into hollow needle 84 which has pierced septum 60 and, as best seen in FIG. 19C, will then flow past conventional umbrella type check valve 54. When the reservoir fill control means, the character of which will presently be described, is in the open position, the fluid will flow into a stub passageway 92 and then into passageway 48. From passageway 48 the fluid will flow into inlet passageway 50 and then into reservoir 36.

As the fluid flows into reservoir 36, it will exert an inward pressure on the plunger end portion 40a of pusher member 40 causing it to move rearwardly of chamber 36 in the manner shown in FIG. 12. As the pusher member moves rearwardly of chamber 36 it will exert forces on spring member 38 causing it to it to expand from its retracted configuration shown in FIG. 6 to its expanded configuration shown in FIG. 12. This rearward movement of pusher member 40 can be viewed through the volume indicator window 99 indicating that the reservoir has changed from an empty configuration to a filled configuration (FIG. 2).

As the reservoir 36 fills with fluid, any gases trapped within the reservoir will be vented to atmosphere via vent means "V" mounted in portion 34b of the housing. This vent means here comprises a gas vent 102 that can be constructed of a suitable hydrophobic porous material such as a porous plastic.

Upon opening the fluid delivery path to the fluid delivery means of the invention, shown here as a conventional administration set 104 (FIG. 2), the stored energy means, or spring 38, will tend to return to its starting configuration thereby controllably urging fluid flow outwardly of reservoir 36 via the flow control means of the invention the character of which will presently be described.

Administration set 104 is connected to the second portion 34b of housing 34 by a connector 106 in the manner shown in FIG. 1 of the drawings. The proximal end 108a of administration line 108 of the administration set is in communication with an outlet fluid passageway 110 which is formed in housing portion 34b in the manner best seen in FIGS. 1 and 6, disposed between the proximal end and 103a the distal end 103b of the administration line are a conventional gas vent and filter 112. Provided at the distal end 103b is a luer connector 116 of conventional construction (FIG. 2).

A number of beneficial agents can be contained within vial 76 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

As the fluid contained within reservoir 36 is urged outwardly thereof by the stored energy means, the fluid will flow under pressure through the reservoir outlet 120 (FIG. 7) and then on toward the flow control means, or flow control assembly 126 of the invention. This important flow control means functions to precisely control the rate of fluid flow flowing from the reservoir 36 toward the patient. Turning to FIGS. 19A, 19B, 19C, and 19D the fill assembly 70 is shown mated with a fluid-dispensing component of a slightly different construction from that shown in FIGS. 6 through 13 of the drawings. Because this alternate form of fluid dispensing component is similar in many respects to the fluid dispensing component shown in FIGS. 6 through 13 of the drawings, like numerals are used in FIGS. 19A, 19B, 19C, and 19D to identify like parts.

As before, the apparatus here comprises a snap together outer housing 34 having a first, second and third portions 34a, 34b and 34c respectively. Housing portion 34a comprises the reservoir portion, housing portion 34b comprises the rate control portion and housing portion 34c comprises the fill and delivery portion.

Figure 19E:
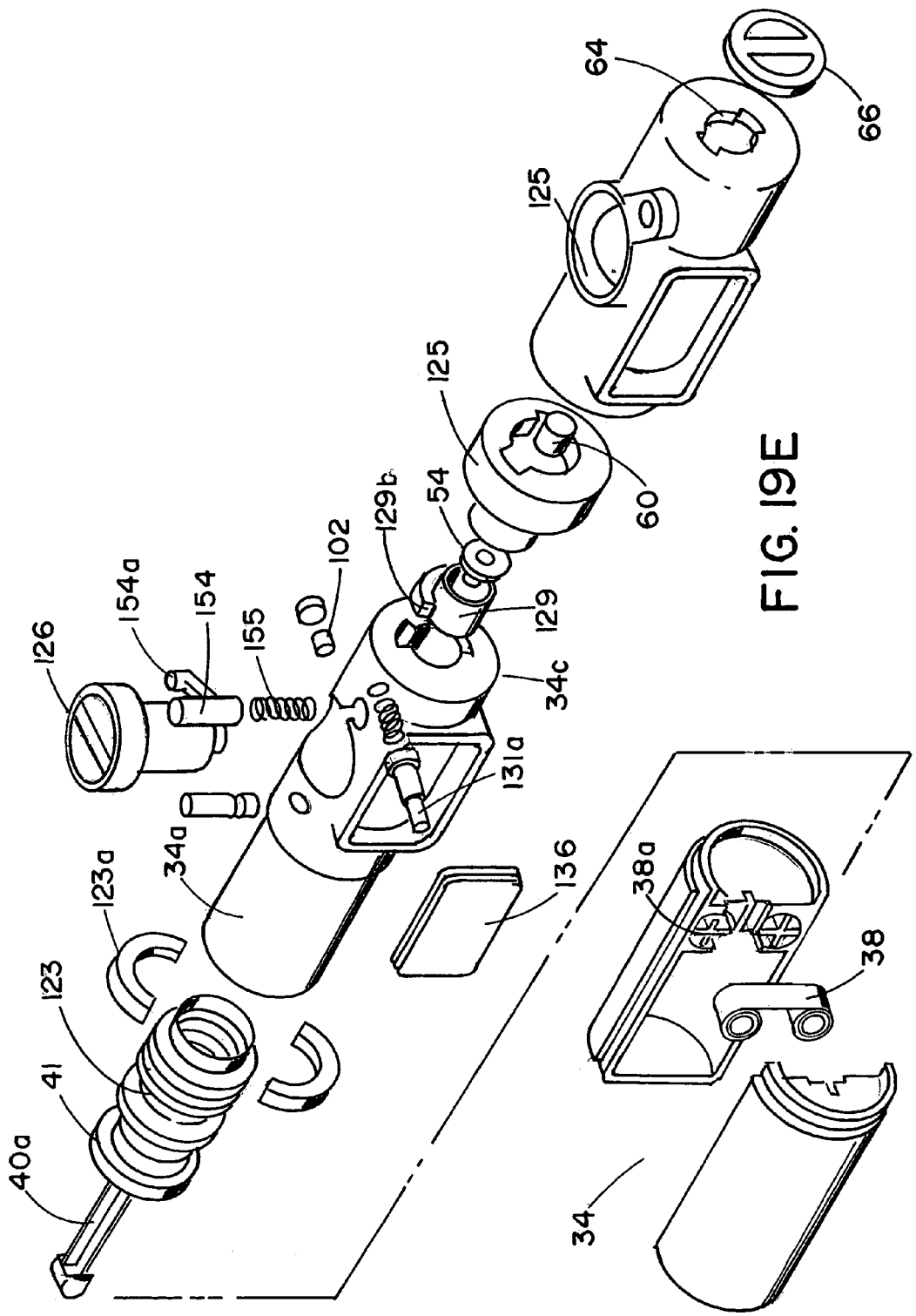
FIG. 19E is a generally perspective, exploded view of the form of the delivery device of the invention illustrated in FIG. 19A.

Disposed within first portion 34a of outer housing 34 is the novel stored energy means of the invention for causing the fluid contained within fluid reservoir 36a, which is of a different construction from reservoir 36, to controllably flow outwardly of the housing and into the fluid dispensing means. In this latest form of the invention, reservoir 36a is formed by an accordion like, expandable, contractible bellows 123, which is of the construction shown in FIGS. 19A and 19B. Bellows 123 is held in position within housing 34 by a split capture ring 123a (FIG. 19E). In a manner presently to be described bellows 123 expands during the filling step from the retracted position shown in FIG. 19A to the expanded position shown in FIG. 19C and is urged to return toward its starting position by the stored energy means of the invention. This important stored energy means, which is identical to that previously described, comprises a constant force spring member 38 that is carried within the first portion 34a of the outer housing.

After the spring is extended during the filling operation in the manner shown in FIG. 19C, it will tend to uniformly return toward its starting configuration and in so doing will exert a constant force on an alternate form of pusher member 40a, which is housed within housing portion 34a in the manner shown in FIGS. 19A and 19C. As the spring returns to its starting configuration, the cup like head portion 41 of the pusher member will exert a substantially constant force on the bellows 123 causing the fluid contained within fluid reservoir 36a to flow outwardly through outlet 44 formed in the rate control housing 46 at a substantially constant rate (FIG. 7).

Forming an important aspect of the apparatus of the present invention is fill means which is carried by the third portion 34c of outer housing 34 for filling either reservoir 36 or reservoir 36a with the fluid to be dispensed. As shown in the drawings, rate control housing 46 includes a fluid passageway 48 in communication with inlet 50 of the fluid reservoirs. Proximate its forward end 48a, fluid passageway 48 communicates with a cavity 52 formed within the third portion 34c of the housing. Disposed within cavity 52 is a conventional, umbrella type check valve 54 which permits fluid flow toward fill passageway 48, but blocks fluid flow in the opposite direction. Cavity 52 communicates, via a stub passageway 56, with a cavity 58 that houses a pierceable septum 60, which comprises a part of one form of the fill means of the invention. Septum 60 may be a conventional slit septum, the character well understood by those skilled in the art 60, which is pierceable by the cannula of a filling syringe assembly which contains the medicinal fluid to be dispensed and which, in a manner presently to be described, can be used to fill or partially fill reservoir 36 via passageway 48.

Third portion 34c of housing 34 includes bayonet type connector portion 64 that is normally closed by a closure cap 66 (FIGS. 6 and 7). Connector portion 64 of the housing is adapted to receive the connector portion 68 of the fill syringe assembly of the invention, which is generally designated in FIG. 14 by the numeral 70 (see also FIG. 16B). As shown in FIGS. 14, 15 and 16, the syringe fill assembly 70 includes a hollow housing 72 that is provided with a chamber 74 for telescopically receiving a medicament containing fill vial 76 (FIG. 17), the construction of which will presently be described.

An elongated support 78, which is mounted within chamber 74 of the syringe fill assembly 70, includes threaded end portions 80 and 81 and carries an elongated, longitudinally extending, hollow needle 82 having a central fluid flow passageway. The central fluid passageway of the hollow needle 82 communicates with the central fluid flow passageway of a second needle or cannula 84 that is carried interiorly of the syringe connector 68. Syringe connector 68 is threadably interconnected within portion 81 of support 78 in the manner shown in FIG. 16A. Second cannula 84 is adapted to pierce septum 60 when the syringe assembly is operably interconnected with third portion 34c of housing 34 in the manner shown in FIG. 19 of the drawings. Chamber 74, elongated support 78 and hollow needles 82 and 84 comprise a part of the fill means of the apparatus of the invention.

Referring particularly to FIG. 17, the medicament containing fill vial 76 includes a body portion 76a, having a fluid chamber 88 for containing the injectable fluid medicament. Chamber 88 is provided with a first open end 88a and second closed end 88b. First open end 88a is sealably closed by closure means here provided in the form of an externally threaded elastomeric plunger 90 which is telescopically movable within chamber 88 from a first location where the plunger is disposed proximate first open end 88a to the second, device-fill location where the plunger is disposed proximate second closed end 88b.

After removal of a closure member 92 from the syringe assembly in the manner shown in FIG. 16, vial 76 can be inserted into chamber 74 (FIGS. 17 and 18). As the fill vial is so introduced and the plunger 90 is threadably interconnected with threaded end 80 of support 78, the sharp end of the elongated needle 82 will pierce the central wall 90a of the elastomeric plunger in the manner shown in FIG. 18. Following removal of cover member 94 which covers connector portion 68 of the syringe assembly (FIG. 16), the assembly shown in FIG. 18 of the drawings can be mated with the fluid dispenser in the manner shown in FIG. 19. This done, the gripping fingers 96 can be retracted from the retracted position shown in FIG. 15 to the extended, opera of position shown in FIG. 16.

With the syringe fill assembly of the invention mated with the fluid dispenser in the manner of shown in FIGS. 19, 19A and 19C the caregiver can grip the fingers 96 with his or her fingers and can exert an inward pressure on vial 76 causing the vial to move inwardly of chamber 74. A continuous movement of the vial into chamber 74 will cause the structural support 78 to move the elastomeric plunger inwardly of the vial chamber 88 in a direction toward the second or closed end 88b of the vial chamber. As the plunger is moved inwardly of the vial, the fluid "F" (FIG. 12) contained within the vial chamber will be expelled there from into the hollow elongated needle 82. The fluid will then flow into hollow needle 84 which has pierced septum 60 and, as best seen in FIG. 7, will then flow past conventional umbrella type check valve 54, into a stub passageway 92 and thence into passageway 48. From passageway 48 the fluid will flow into inlet passageway 50 and then into either reservoir 36 or reservoir 36a.

As shown in FIG. 12, as the fluid flows into the reservoir 36, it will exert an inward pressure on the plunger end portion of pusher member 40 causing it to move the rearwardly of reservoir 36 in the manner shown in FIG. 12 and causing the plunger to exert forces on spring member 38. These forces will cause the spring to expand from its retracted configuration shown in FIG. 6 to its expanded configuration shown in FIG. 12. This rearward movement of pusher member 40 can be viewed through the volume indicator window 99 indicating that the reservoir has changed from an empty configuration to a filled configuration (FIG. 2).

As the reservoir 36 fills with fluid, any gases trapped within the reservoir will be vented to atmosphere via vent means "V" mounted in portion 34b of the housing. This vent means here comprises a gas vent 102 that can be constructed of a suitable hydrophobic porous material such as a porous plastic.

As shown in FIG. 19C, as the fluid flows into the reservoir 36a of the alternate form of the fluid delivery device, bellows 123 will expand causing it to exert an inward pressure on the plunger end portion 41 of pusher member 40a causing it to move rearwardly in the manner shown in FIG. 19C. This rearward movement of the plunger will cause it to exert forces on spring member 38 and will cause the spring to expand from its retracted configuration shown in FIG. 19A to its expanded configuration shown in FIG. 19C. This rearward movement of pusher member 40a can be viewed through the volume indicator window 99 indicating that the reservoir has changed from an empty configuration to a filled configuration (see FIG. 2).

Figure 10:
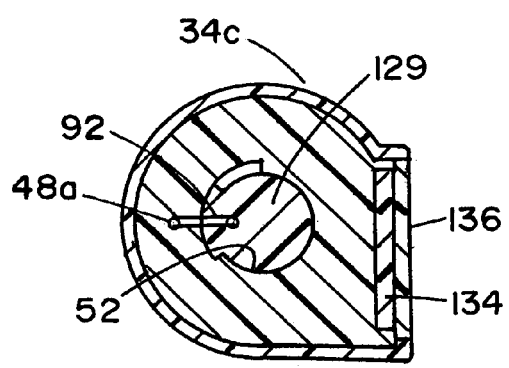
FIG. 10 is a cross-sectional view taken along lines 10-10 of FIG. 7.

This alternate form of the fluid delivery device, like the earlier described fluid delivery device, includes novel reservoir fill control means. As illustrated in FIGS. 6, 7, 10, 11, 19A, 19B, 19C, 19D, 33 and 34 the fill control means here comprises a generally cylindrical shaped control member 125 which is rotatable from a first off position shown in FIGS. 11, 19B and 33 to a second reservoir fill position shown in FIGS. 10, 19B and 34. As member 125 is rotated, a stub passageway 127 is moved into and out of index with an outlet passageway 129a formed in a control member 129 which is housed within portion and 34b of housing 34 (see FIGS. 10, 11, 19B and 19C). As indicated in FIGS. 10, 19D and 34, when outlet passageway 129a is in index with stub passageway 127, a fluid communication path between elongated needle 82 and the reservoir fill line 48 is established. With this construction, as the medicament vial 76 is urged forwardly of housing 72 in the manner indicated in FIG. 19C, fluid will flow into elongated needle 82, past check valve 54, into stub passageway 127, into fill line 48 and then into reservoir 36 filling the reservoir in the manner illustrated in FIG. 19C.

The reservoir fill control means of this latest form of the invention also includes locking means for preventing rotation of member 129. This locking means here comprises a locking assembly 131 which includes a spring loaded fill locking member 131a which is carried within housing portion 34c in the manner shown in FIGS. 2, 13 and 19E. More particularly, when member 131a is pushed inwardly it will engage a shoulder 129b formed on member 129 preventing its rotation (see FIG. 19E).

Once again, as the reservoir 36a fills with fluid, any gases trapped within the reservoir will be vented to atmosphere via vent means "V" mounted in portion 34b of the housing. This vent means here comprises a gas vent 102 that can be constructed of a suitable hydrophobic porous material such as a porous plastic.

Upon opening the fluid delivery path to the fluid delivery means of the invention, shown here as a conventional administration set 104 (FIG. 2), the stored energy means, or spring 38, will tend to return to its starting configuration thereby controllably urging fluid flow outwardly of reservoir 36 via the flow control means of the invention the character of which will presently be described.

Administration set 104 is connected to the second portion 34b of housing 34 by a connector 106 in the manner shown in FIG. 1 of the drawings. The proximal end 108a of administration line 108 of the administration set is in communication with an outlet fluid passageway 110 which is formed in housing portion 34b in the manner best seen in FIGS. 1, 2, 6 and 12. Disposed between the proximal end 103a and the distal end 103b of the administration line are a conventional gas vent and filter 112. Provided at the distal end 103b is a luer connector 116 of conventional construction (FIG. 2).

A number of beneficial agents can be contained within vial 76 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

As the fluid contained within reservoir 36 is urged outwardly thereof by the stored energy means, the fluid will flow under pressure through the reservoir outlet 120 (FIG. 7) and then on toward the flow control means, or flow control assembly 126 of the invention. This important flow control means functions to precisely control the rate of fluid flow flowing from the reservoir 36 toward the patient.

Figure 9:
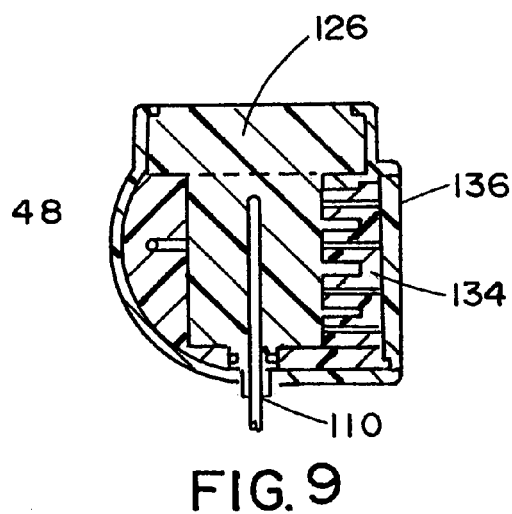
FIG. 9 is a cross-sectional view taken along lines 9-9 of FIG. 6.
Figures 30, 31, 32:
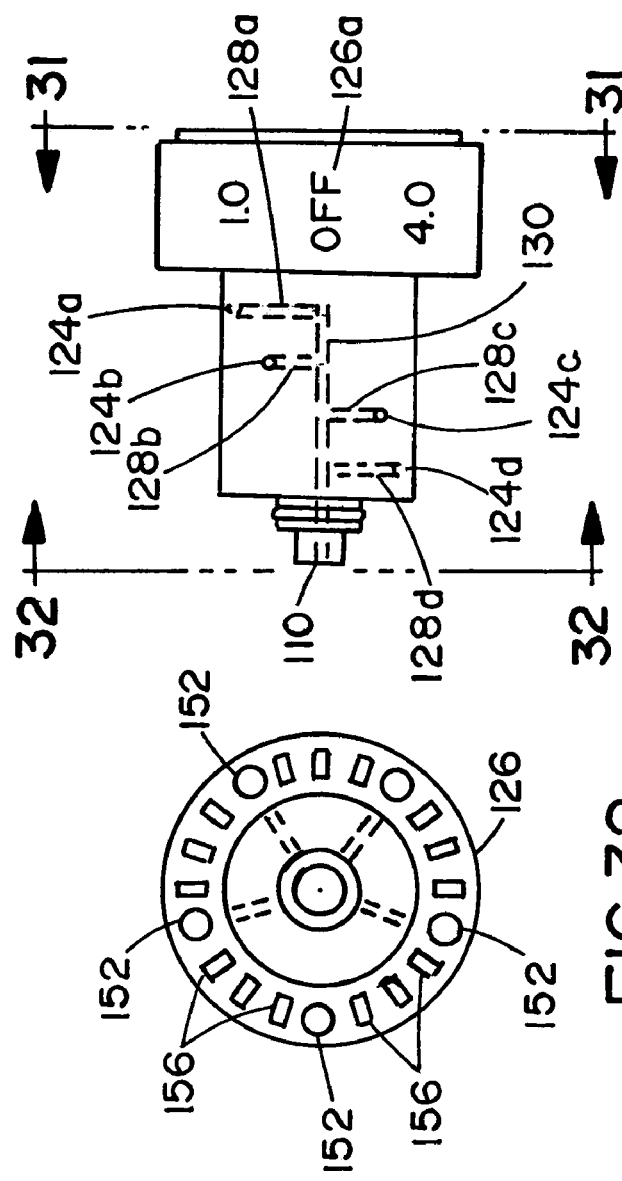
FIG. 30 is a side elevational, cross-sectional view of one form of the selector knob of the rate control assembly.
FIG. 31 is a view taken along lines 31-31 of FIG. 30.
FIG. 32 is a view taken along lines 32-32 of FIG. 30.
Figure 33:
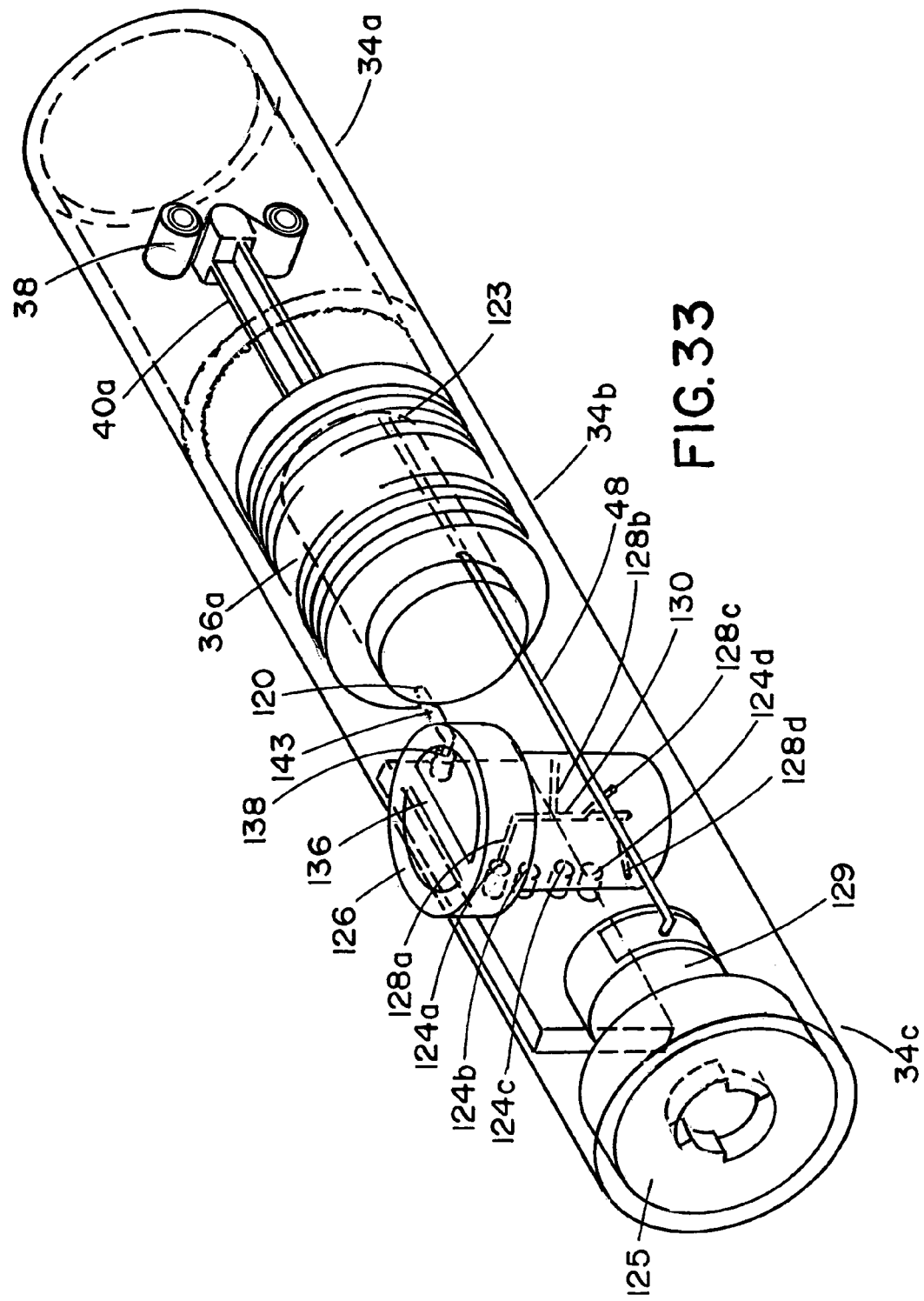
FIG. 33 is a generally perspective illustrative view of a portion of the fluid delivery device of the invention showing the fluid flow path during the fill step.
Figure 38:
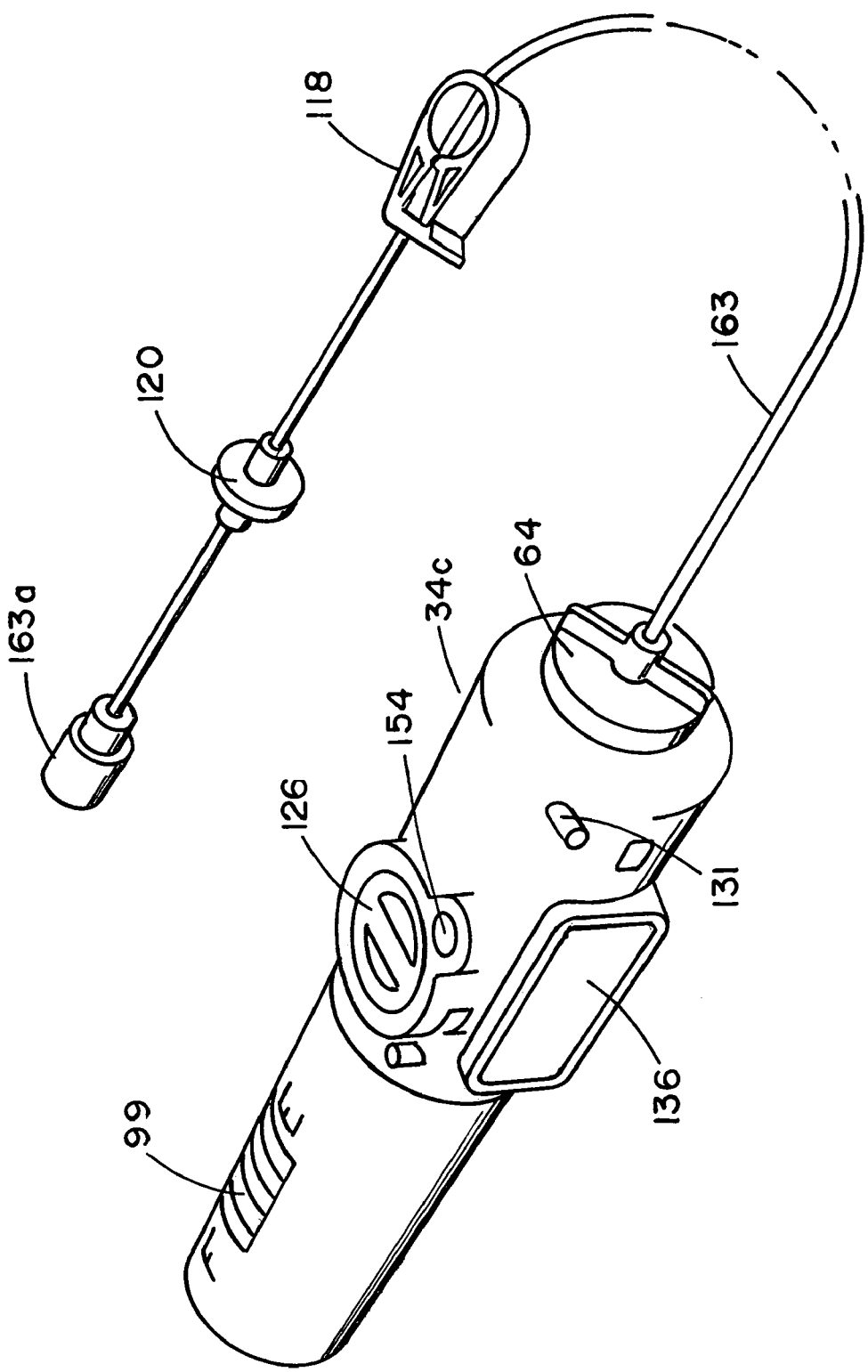
FIG. 38 is a generally perspective, top view of an alternate form of fluid dispensing apparatus of the present invention.
Figure 39:
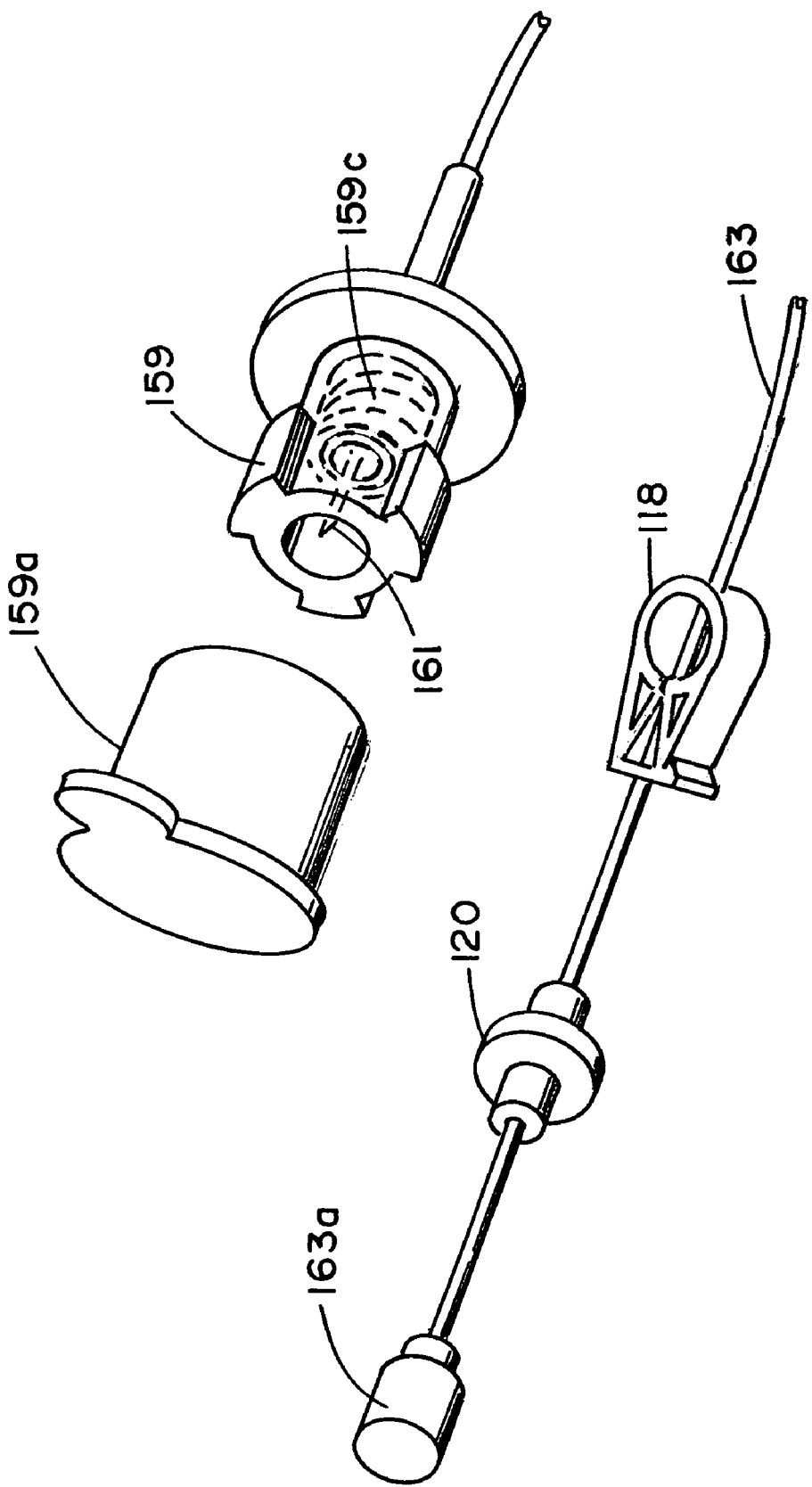
FIG. 39 is a generally perspective exploded view of the fill subassembly of the fluid dispensing device shown in FIG. 38.
Figure 40:
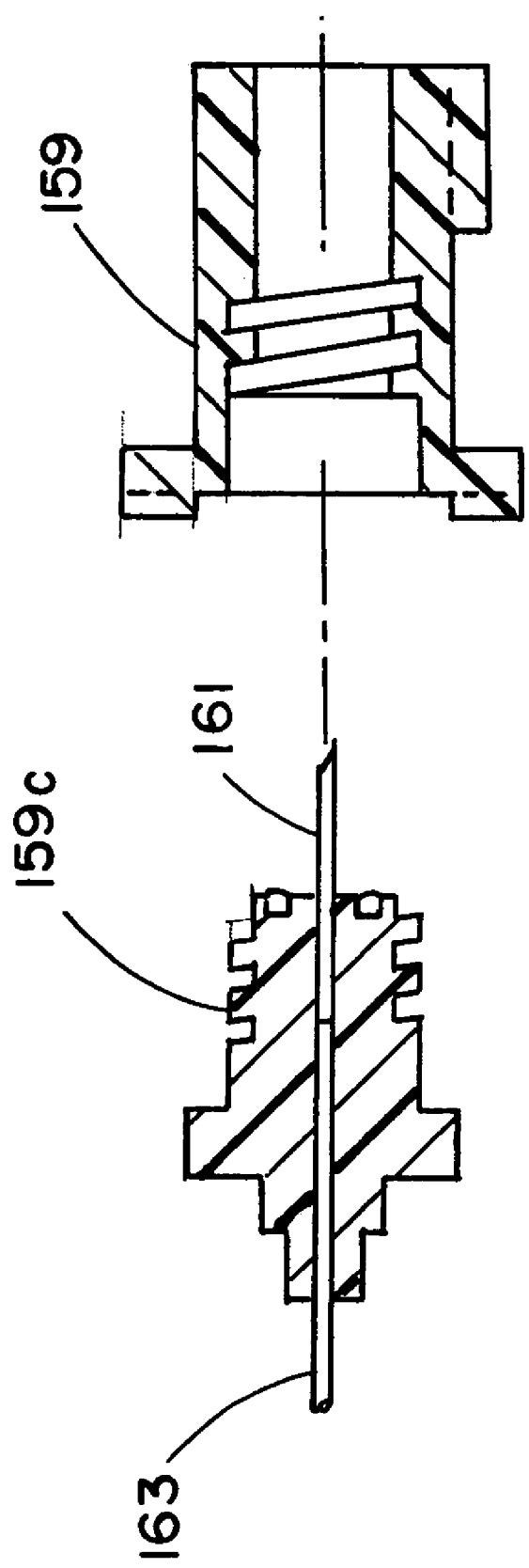
FIG. 40 is an enlarged cross-sectional, exploded view of the connector portion of the fill subassembly shown in FIG. 39.
Figures 41, 42, 43:
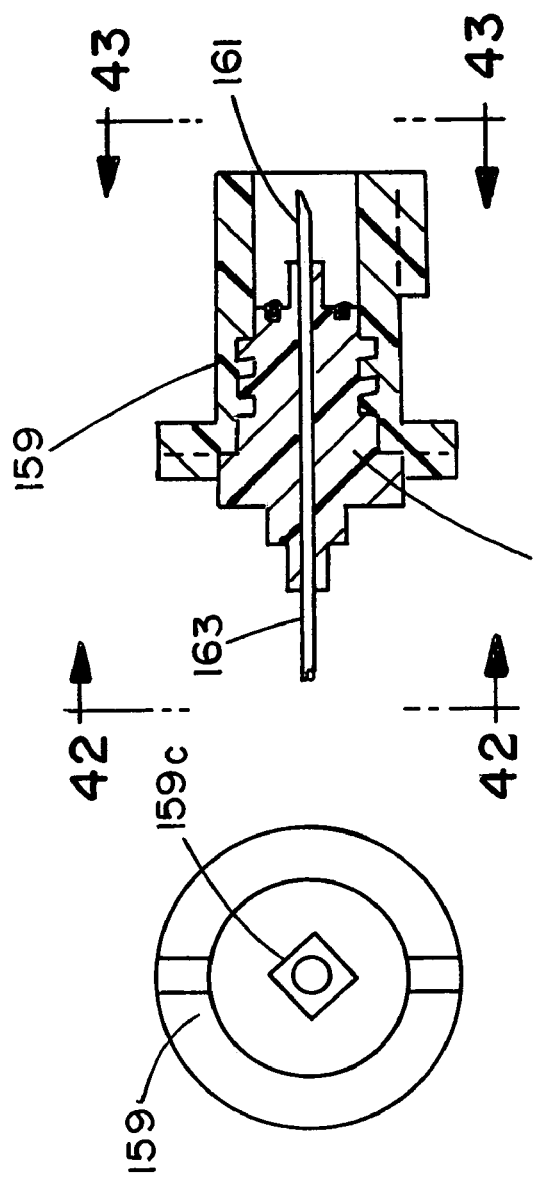
FIG. 41 is a cross-sectional view of the connector portion of the fill subassembly shown in an assembled configuration.
FIG. 42 is a view taken along lines 42-42 of FIG. 41.
FIG. 43 is a view taken along lines 43-43 of FIG. 41.
Figure 44:
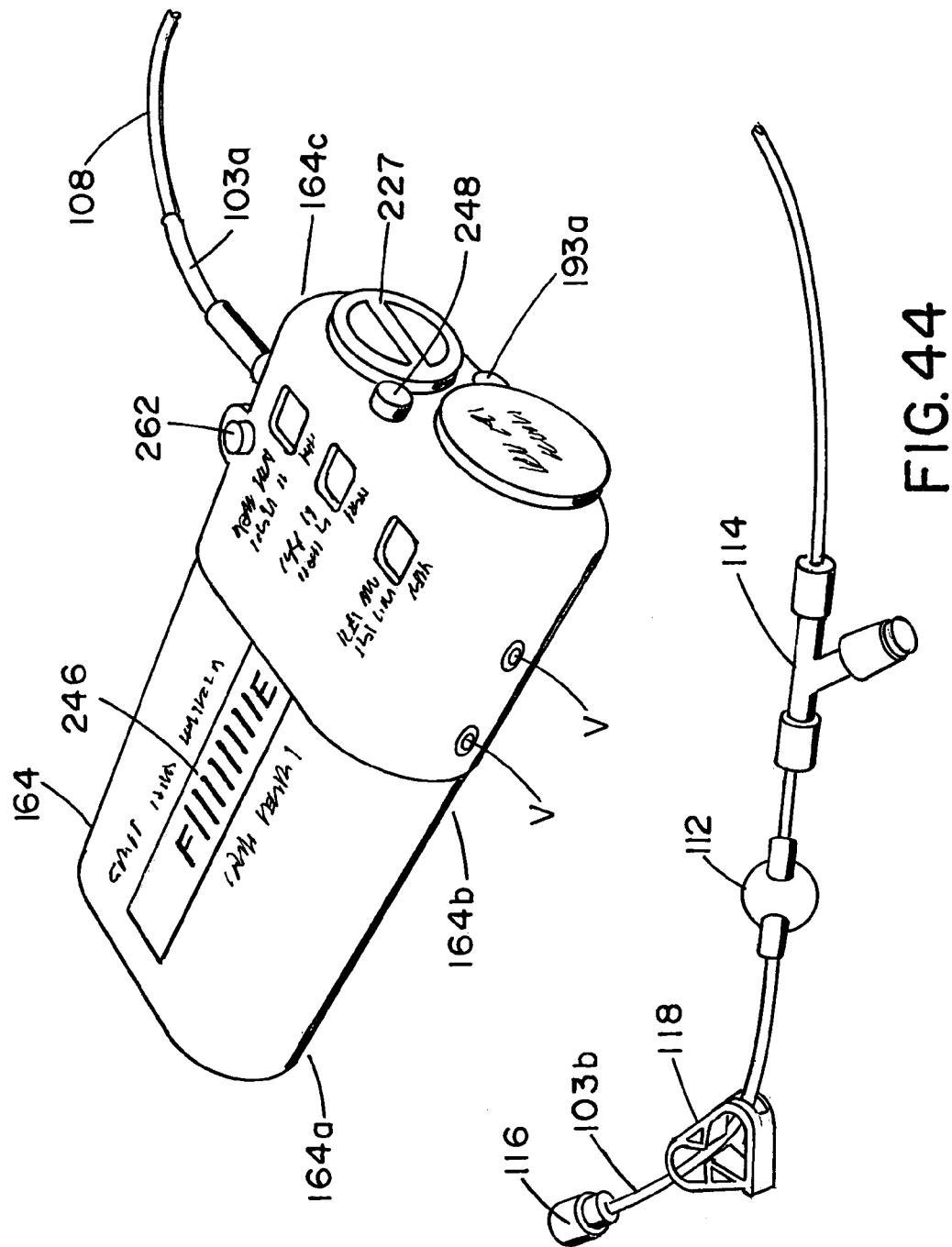
FIG. 44 is a generally perspective view of an alternate form of the fluid dispensing device of the present invention.
Figure 50:
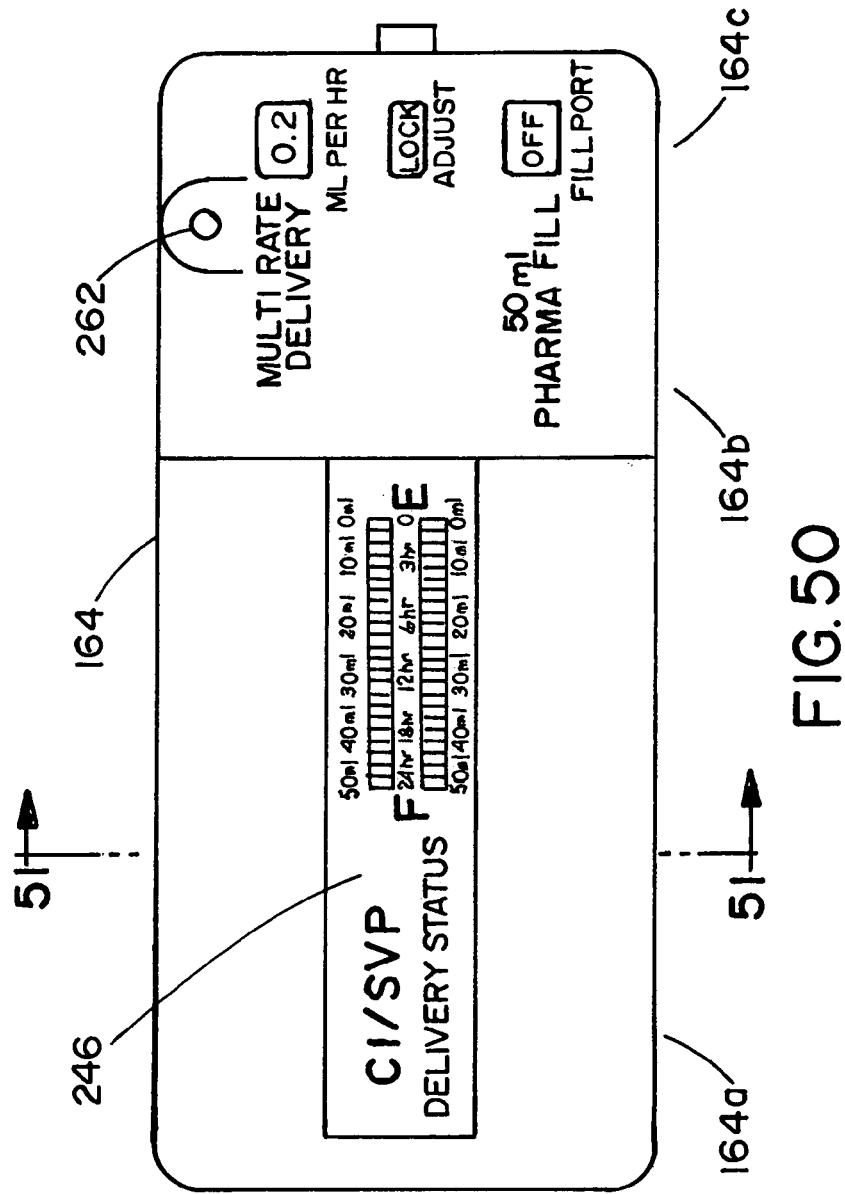
FIG. 50 is an enlarged, top elevational view of the housing of the fluid dispensing device shown in FIG. 44.
Figure 51:
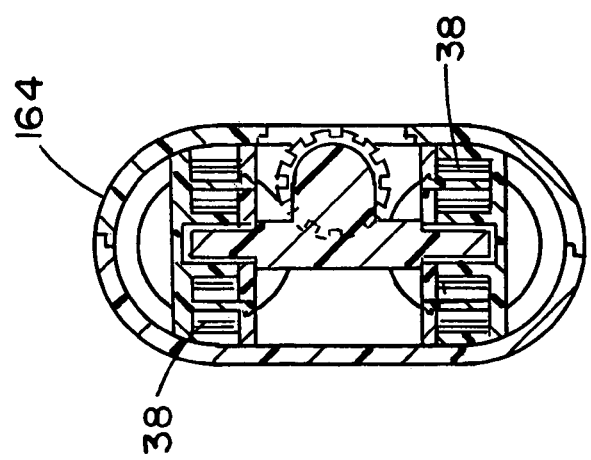
FIG. 51 is a cross-sectional view taken along lines 51-51 of FIG. 50.

Referring to FIGS. 6 through 9 and 20 through 24, it can be seen that flow control assembly 122 which is housed within housing portion 34c comprises the previously identified rate control housing 46 having a plurality of vertically spaced apart fluid inlets 124a, 124b, 124c and 124d respectively and a rate control, or selector 126 that is rotatably carried within a vertical bore 127 formed in housing 46 (see FIGS. 6, and 9). As illustrated in FIGS. 30 and 33, flow rate control or selector member 126 is uniquely provided with a plurality of radially extending flow control channels 128a, 128b, 128c and 128d respectively each having an inlet and an outlet in fluid communication with an axially extending passageway 130 formed in selector knob 126. As best seen in FIGS. 6 and 30, passageway 130 is in fluid communication with outlet 110 and with administration line 108. In a manner presently to be described, selector knob 126, which comprises a part of the selector means of the invention, functions to place a selected one of the inlets of the radially extending flow control channels of the selector knob in communication with a selected one of a plurality of a plurality of fluid flow micro channels formed in the rate control plate component 134 of the flow rate control assembly 136 of the invention (FIG. 28).

As best seen in FIG. 7, the rate control assembly 136 includes an inlet port 138 that is in communication with the outlet port 120 of reservoir 36 via a first and second stub passageways 44 and 142. As the pusher assembly 40 is urged forwardly by the stored energy means, the fluid contained within reservoir 36 will flow through the outlet port 120, through passageways 44 and 142 and into inlet 138 of the rate control assembly in a manner to permit each of the micro channels of the rate control plate 134 to fill with the medicinal fluid. As indicated in FIGS. 9 and 30 and as will be described in greater detail hereinafter, rotation of the selector knob 126 within bore 127 will permit each of the vertically spaced outlets of the micro channels to be aligned with a selected one of the inlets of the selector 126. The fluid can then flow into a selected one of the plurality of passages 128a, 128b, 128c and 128d, into axially extending passageway 130, into the administration line and then on to the patient at a precise rate of flow.

In the alternate form of the apparatus in which the fluid reservoir 36a is defined by the bellows component 123, the rate control assembly 136 functions in a similar manner. More particularly, as shown in FIG. 34, the inlet port 138 of the rate control assembly 126 is similarly in communication with the outlet port 120 of reservoir 36a via passageway 143. As the pusher assembly 40a is urged forwardly by the stored energy means, the fluid contained within reservoir 36a will flow through the outlet port 120, through passageway 143 and into inlet 138 of the rate control assembly in a manner to permit each of the micro channels of the rate control plate 134 to fill with the medicinal fluid. As previously described, rotation of the selector knob 126 within bore 127 will permit each of the vertically spaced outlets of the micro channels to be aligned with a selected one of the inlets 124a, 124b, 124c and 124d of the rate control housing 136. The fluid can then flow into a selected one of the plurality of passages 128a, 128b, 128c and 128d, into axially extending passageway 130, into the administration line and then on to the patient at a precise rate of flow.

It is to be understood that the flow micro channels 128 may be of different sizes, lengths and configurations as shown by FIG. 28. Further, the flow control micro channels may be rectangular in cross-section, or alternatively, they can be semicircular in cross-section, U-shaped in cross-section, or they may have any other cross-sectional configuration that may be appropriate to achieve the desired fluid flow characteristics.

To assist in rotating knob 126, the enlarged diameter portion 126a of the knob is provided with a finger gripping bar 150. As illustrated in FIGS. 30 and 32, selector knob 126 is provided with a plurality of circumferentially spaced apart indexing cavities 152 that closely receive an indexing finger 154a of locking member 154 which forms a part of the indexing means of the invention for appropriately indexing the selector knob. Disposed intermediate the indexing cavities 152 are circumferentially spaced ratcheting cavities 156 that receive a ratcheting tab 158 that is formed within bore 127 in a manner shown in FIG. 23 to provide tactile indication of rotation of the selector knob.

Figure 11:
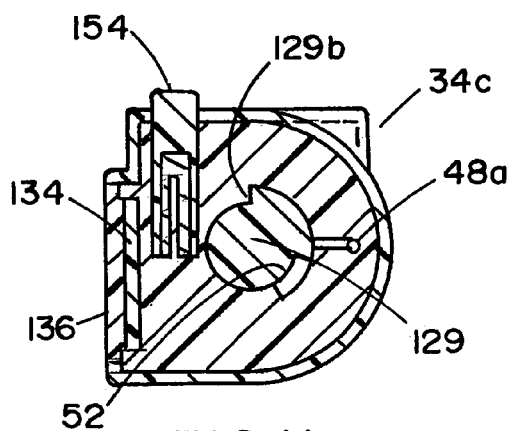
FIG. 11 is a cross-sectional view taken along lines 11-11 of FIG. 7.
Figure 8:
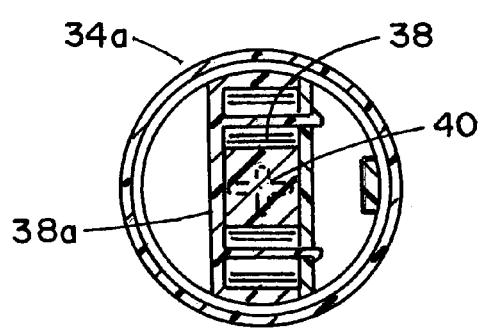
FIG. 8 is a cross-sectional view taken along lines 8-8 of FIG. 6.
Figure 13:
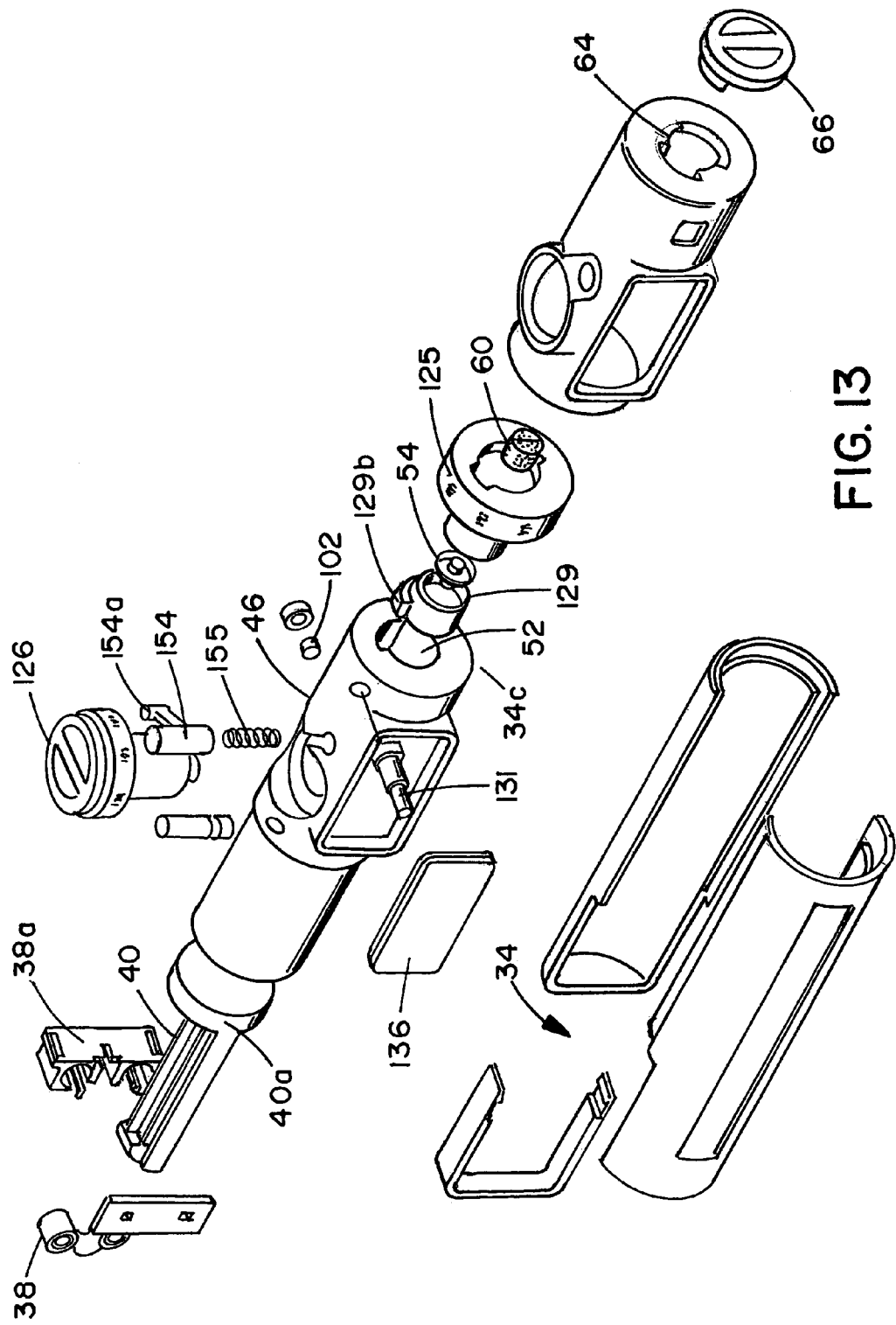
FIG. 13 is a generally perspective, exploded view of the form of the delivery device of the invention illustrated in FIGS. 1 and 2.

Also forming a part of the flow control means of the invention is the previously identified selector knob locking means for preventing rotation selector knob 126. This selector knob locking means here comprises a locking member 154 and a cooperating coil spring 155 (FIGS. 13, 11 and 19E). Locking member 154 includes indexing finger 154*a* which is continuously urged into a selected one of the indexing cavities 152 formed in knob 126 (FIG. 32). Accordingly, to permit rotation of knob 126 a downward force must be exerted on member 154 against the urging of spring 155 to move finger 154*a* out of the indexing cavity 152.

The details of the construction of the rate control plate, or member 134 and the various methods of making the rate control plate will now be considered. With respect to materials, the most appropriate materials for constructing the rate control plate are medical grade polymers. These types of polymers include thermoplastics, duroplastics, elastomers, polyurethanes, acrylics and epoxies. In other variations, the materials used for the flow control plate may be made of glass or silica. In further variations, the flow control component may be made of metals or inorganic oxides.

Using the foregoing materials, there are several ways that the flow control channels 128 can be made. These include injection molding, injection-compression molding, hot embossing and casting. The techniques used to make these imbedded fluid channels are now commonplace in the field of microfluidics, which gave rise to the lab-on-a-chip, bioMEMS and micro-total analysis systems (μ-TAS) industries. Additionally, depending on the size of the fluid channels required for a given flow rate, more conventional injection molding techniques can be used.

The first step in making the channels using an injection molding or embossing process is a lithographic step, which allows a precise pattern of channels to be printed on a "master" with lateral structure sizes down to 0.5 □m. Subsequently, electroforming is performed to produce the negative metal form, or mold insert. Alternatively for larger channel systems, precision milling can be used to make the mold insert directly. Typical materials for the mold insert or embossing tool are nickel, nickel alloys, steel and brass. Once the mold insert of embossing tool is fabricated, the polymer of choice may be injection molded or embossed to yield the desired part with imprinted channels.

Alternatively, channels can be made by one of a variety of casting processes. In general, a liquid plastic resin, for example, a photopolymer can be applied to the surface of a metal master made by the techniques described in the preceding paragraph and then cured via thermal or ultraviolet (UV) means. After hardening, the material is then "released" from the mold to yield the desired part. Additionally, there are similar techniques available that utilize CAD data of the desired channel configuration and direct laser curing of a liquid monomer to yield a polymerized and solidified part with imbedded channels. This process is available by contract, from, by way of example, example MicroTEC, mbH of Duisburg, Germany.

In order to seal the flow control channels, a planar top plate may be used. In this instance, the channel system may be sealed with a cover, or top plate, which is here defined as any type of suitable cover that functions to seal the channel. The top plate may be sealably interconnected with the base which contains the flow channels by several means, including thermal bonding, sonic welding, laser welding, adhesive bonding and vacuum application.

Thermal bonding may be performed by using a channel base plate material and planar top cover that are made of similar polymeric materials. In this case the two substrates are placed in contact with one another, confined mechanically and heated to 2-5° C. above their glass transition temperature. Following a holding period sufficient enough for the polymer molecules of the two surfaces interpenetrate with one another, the temperature is slowly reduced and a stress free bonded interface with imbedded micro channels is yielded.

Additionally, the top plate, or cover may be bonded to the base plate through the use of one or more suitable bonding materials or adhesives. The bonding material or adhesive may be of the thermo-melting variety or of the liquid or light curable variety. For thermo-melting adhesives, the adhesive material is melted into the two apposed surfaces, thereby interpenetrating these surfaces and creating a sealed channel structure.

Further, liquid curable boding materials or adhesives and light curable bonding materials or adhesives may be applied to one of the surfaces, for example the cover. Subsequently, the other surface is brought into contact with the coated surface and the adhesive is cured by air exposure or via irradiation with a light source. Liquid curable boding materials or adhesives may be elastomeric, for example, thermoplastic elastomers, natural or synthetic rubbers, polyurethanes, and silicones. Elastomeric bonding materials may or may not require pressure to seal the channel system. They may also provided closure and sealing to small irregularities in the apposed surfaces of the channel system.

A channel system may also be formed and sealed in cases where two surfaces are being joined and one of the surfaces has one or more apertures. In order to promote bonding between these two surfaces, a vacuum may be applied to the apertures. Bonding may then be accomplished by thermal methods or after previously having applied a bonding material or adhesive.

While the rate control plate, or base member can be constructed in various sizes, a rate control chip which is rectangular in shape and approximately 11 cm long and approximately 5 cm wide is suitable for the present application. Similarly, while the depth of the channels can vary depending upon the end use of the device, as a general rule the depth of the channels is on the order of approximately 10-100 um.

As previously mentioned, the cross section of the set of channels may vary in area over the members of the set of individual channels so as to achieve the specified flow rate of a particular channel. The cross section may also vary over the length of any particular channel so as to achieve the specified flow rate for the particular channel. Some examples of typical channel cross sections are square, rectangular, elliptical, circular, semi-circular and semi-elliptical. Channel cross sections may also be more complicated than those noted explicitly here.

A typical rate control system of the invention will, by way of example, be able to deliver fluid at five specified flow rates as, for example 0.25, 0.5, 1.0, 2.0 and 5.0 ml/hr. For optimum performance, the flow rate should be constant and within 10% of the desired specified value.

In operation, the flow of fluid through the flow control channels is controlled by taking advantage of the viscous drag imposed on the moving fluid by the walls of the channels. For a given imposed pressure and channel cross section the longer the channel the smaller the flow rate. The pressure required to achieve the desired flow rates in the micron channels is preferably in the range of from 0.01 to 1 ATM. However, for some applications it may be desirable to exceed these limits.

The path that the micro channels take in any given rate control plate, or chip may be straight, a single meander or two or more meanders. The turns of the meanders may be of any angle from approximately 45° to approximately 220°. The runs of straight path between turns of the meanders may be of any length that the chip can accommodate, but these straight runs would typically be from 50 um to 500 um in length.

As shown in FIG. 28, each of the micro channels has an outlet 139a, 139b, 139c and 139d which, upon rotation of selector 126, will align with a selected inlet passageway 48 the fluid will flow into inlet passageway 50 and then into reservoir 36 (see FIG. 12).

Figure 52:
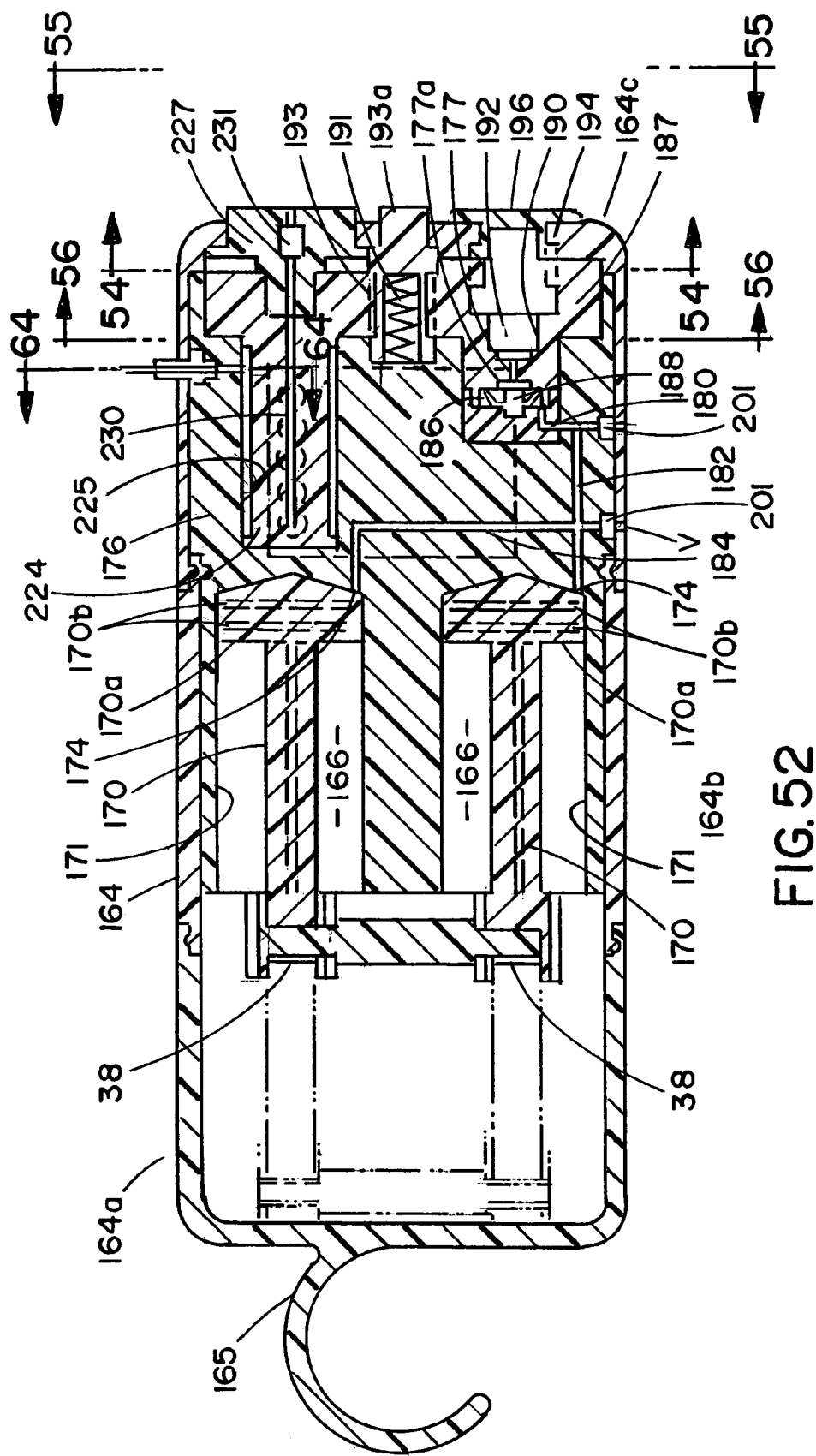
FIG. 52 is a longitudinal cross-sectional view of the fluid dispensing device shown in FIG. 45.

Turning next to FIGS. 44 through 92, still another form of the apparatus of the present invention is there illustrated and generally designated by the numeral 164. This apparatus is similar in some respects to the apparatus shown in FIGS. 1 through 43 and like numerals are used in FIGS. 44 through 92 to identify like components. As best seen in FIG. 52, the apparatus of this latest form of the invention includes a duel reservoirs and duel stored energy means. As before, the apparatus includes a snap together outer housing 164 having a first, second and third portions 164a, 164b and 164c respectively. Housing portion 164a comprises the dual reservoir and duel stored energy portion, housing portion 164b comprises the rate control portion and housing portion 164c comprises the fill and delivery portion. A gripping hook 165 is provided on housing portion 164a for use in conveniently supporting the housing.

The novel stored energy means of this latest form of the invention functions to cause the fluid contained within the identically configured, duel fluid reservoirs 166 (FIGS. 52 and 89) to controllably flow outwardly of the housing and into the fluid dispensing means. In the present form of the invention, this important stored energy means comprises a pair of constant force spring members 38 that are identical in construction and operation to the previously described constant force spring member 38. As depicted in FIGS. 89 and the 90, springs 38 acts on pusher members 170, which are of the character shown in FIGS. 52 and 89. As before, these pusher members can be constructed from a wide variety of materials including stainless steel. Each of the pusher members includes a head portion 170a which carry a pair of O-rings 170b which sealably engage the inner walls 171 which define reservoirs 166.

After the springs are extended in the manner shown in FIGS. 89 and 90, they will tend to uniformly return toward their starting configuration and in so doing will exert a constant force on the pusher members 170, which are housed within housing portion 164a in the manner shown in FIGS. 52 and 89. As the springs return to their starting configurations, the fluid contained within the fluid reservoirs 166 will be caused to flow outwardly through inlets-outlets 174 formed in the rate control housing 176 at a substantially constant rate (FIG. 52).

Figure 53:
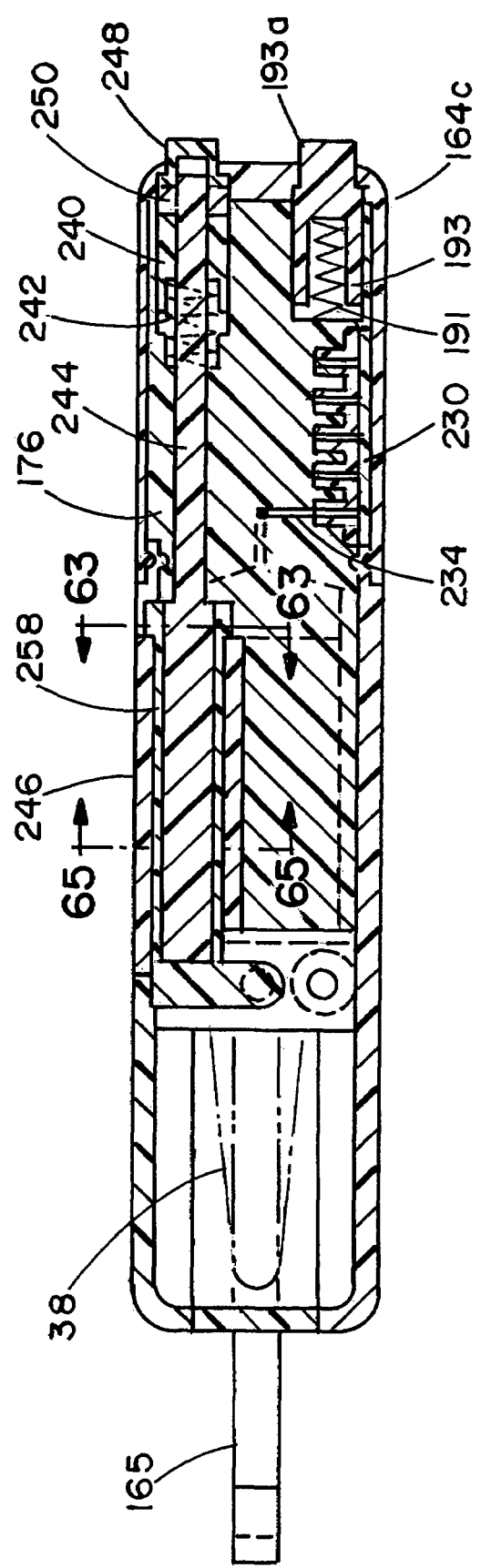
FIG. 53 is a cross-sectional view taken along lines 53-53 of FIG. 50.

Forming an important aspect of the apparatus of the present invention is fill means, which is carried by the third portion 164c of outer housing 164 for filling the reservoirs 166 with the fluid to be dispensed. As best seen in FIG. 53, rate control housing 176 includes a fluid passageway 177 which is in communication with inlets 174 of fluid reservoirs 166 via passageways 180, 182 and 184. Proximate its forward end 177a, fluid passageway 177 communicates within a cavity 186 formed within a syringe connector block 187 (FIG. 52). Disposed within cavity 186 is a conventional, umbrella type check valve 188 which permits fluid flow toward fill passageway 180, but blocks fluid flow in the opposite direction. Cavity 186 communicates, via passageway 177, with a cavity 190 that houses a pierceable septum 192, which comprises a part of one form of the fill means of the invention. Septum 192 may be a conventional slit septum, the character well understood by those skilled in the art, which is pierceable by the cannula of a filling syringe assembly which contains the medicinal fluid to be dispensed and which, in a manner presently to be described, can be used to fill or partially fill reservoirs 166 via passageways 182 and 184.

Figure 56:
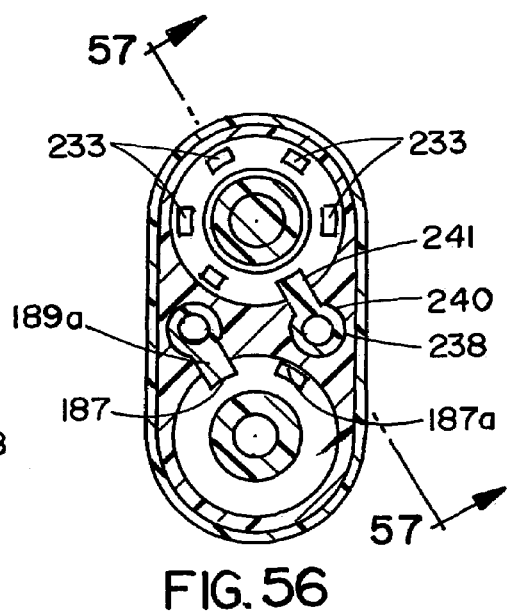
FIG. 56 is a cross-sectional view taken along lines 56-56 of FIG. 52.
Figure 58:
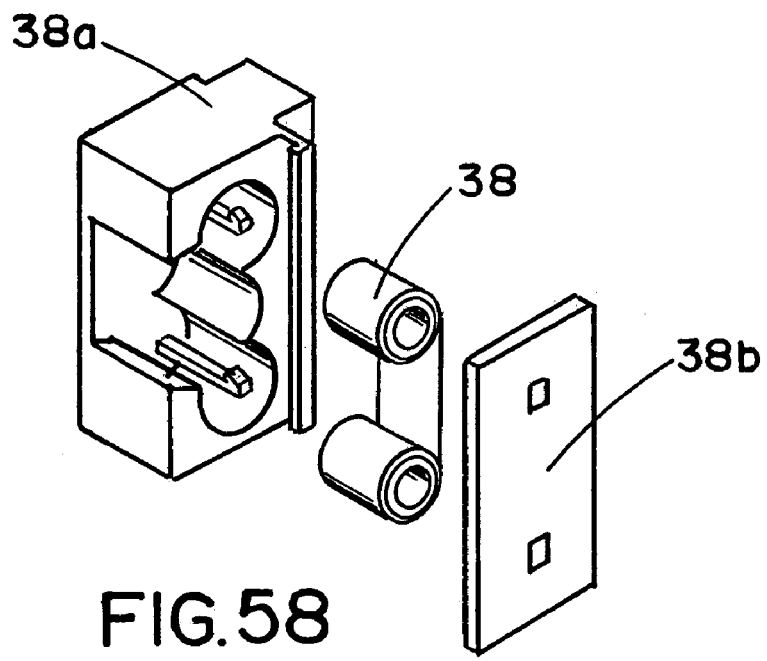
FIG. 58 is a generally perspective, exploded view of the stored energy means of this latest form of the invention.
Figures 59, 60, 61:
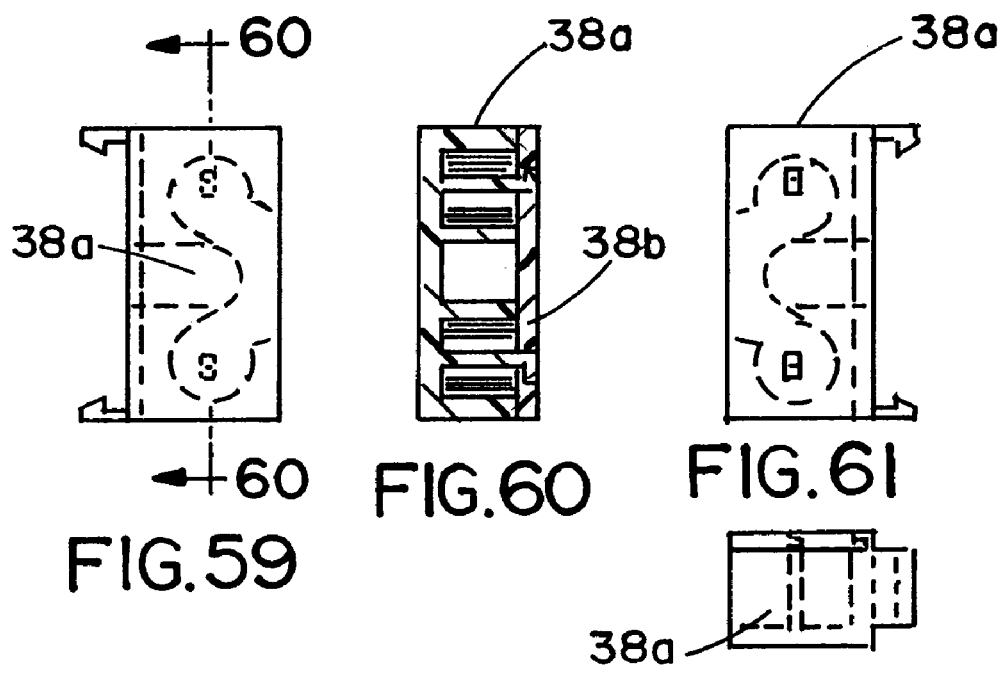
FIG. 59 is a left side view of the housing portion of the stored energy means shown in FIG. 58.
FIG. 60 is a cross-sectional view taken along lines 60-60 of FIG. 59.
FIG. 61 is a right side view of the housing portion of the stored energy means shown in FIG. 58.
Figure 62:
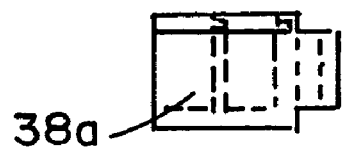
FIG. 62 is a top plan view of the housing portion of the stored energy means shown in FIG. 58.

Syringe connector block 187 includes bayonet type connector portion 194 that is normally closed by a closure cap 196 (FIGS. 48 and 52). Connector portion 194 of the housing is adapted to receive the connector portion 68 of the fill syringe assembly of the invention, which is substantially identical in construction and operation to that previously described and is generally designated by the numeral 70.). As illustrated in FIG. 56, syringe connector block 187 is provided with spaced apart indexing cavities 187a that closely receive an indexing member 189 which forms a part of the syringe fill indexing means of the invention for appropriately indexing syringe connector block 187.

Also forming a part of the syringe fill indexing means of the invention is connector block locking means for preventing rotation of the connector block. This connector block locking means here comprises, in addition to indexing member 189, a coiled spring 191 and an elongated push rod 193 which carries spring 191. Rod 193 has a push button end 193a which extends outwardly of housing portion 164c (FIG. 53). With this construction, when an inward force is exerted on push button end 193 against the urging of spring 191, the connector block can be rotated to a reservoir fill position wherein stub passageway 180 is aligned with passageway 182.

Figure 88:
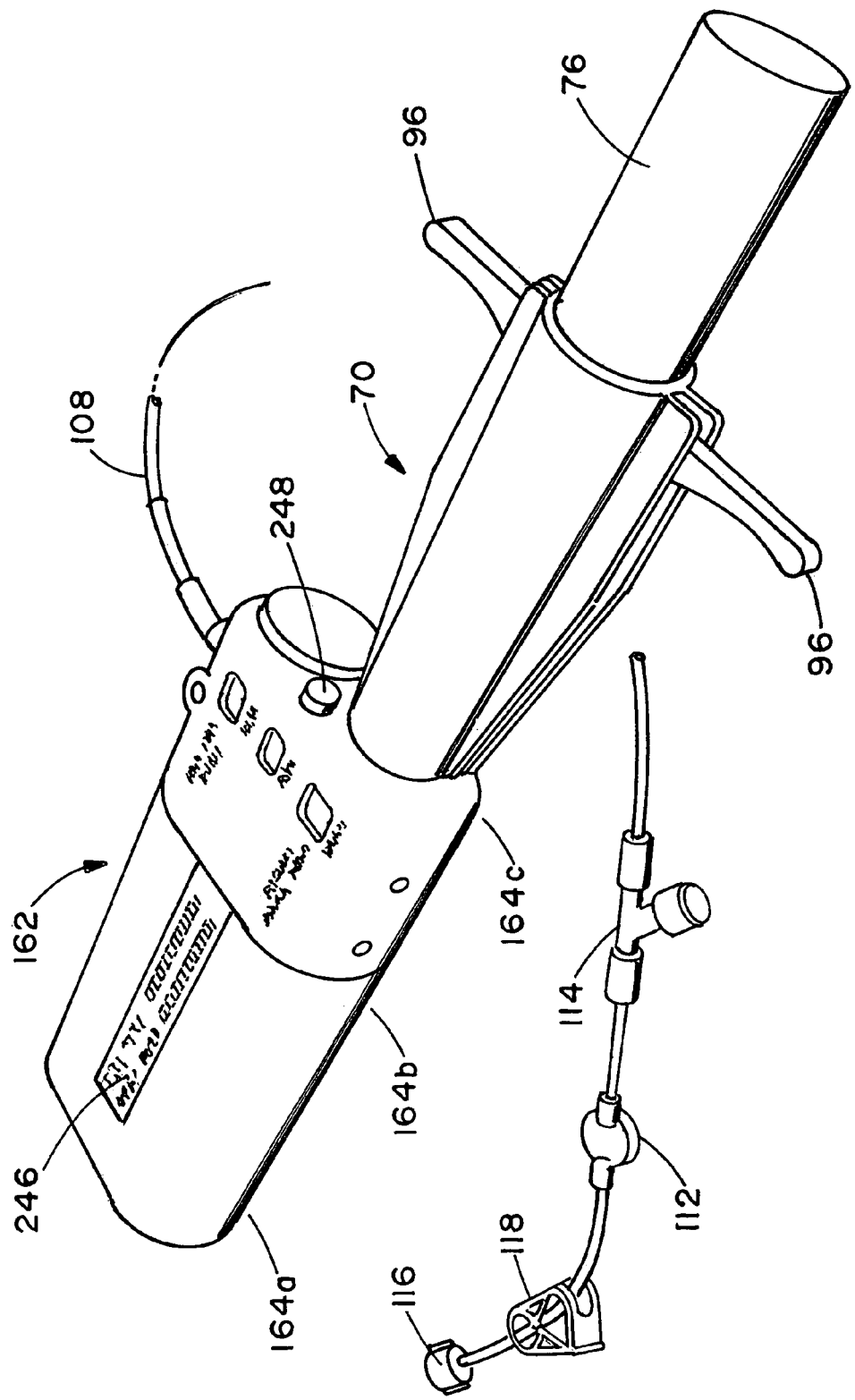
FIG. 88 is a generally perspective view illustrating the fill syringe assembly of the invention mated with the fluid delivery device of this latest form of the invention.

With the syringe fill assembly of the invention mated with the fluid dispenser in the manner of shown in FIG. 88 and the connector block rotated to the fill position, the caregiver can grip the fingers 96 with his or her fingers and can exert an inward pressure on the medicament vial 76 causing the vial to move inwardly. A continuous inward movement of the vial will cause the structural support 78 to move the elastomeric plunger inwardly of the vial chamber 88 in a direction toward the second or closed end 88b of the vial chamber. As the plunger is moved inwardly of the vial, the fluid "F" (FIG. 18) contained within the vial chamber will be expelled there from into the hollow elongated needle 82. The fluid will then flow into hollow needle 84 which has pierced septum 192 and, as best seen in FIG. 52, will then flow past conventional umbrella type check valve 188, into a stub passageway 180 and thence into passageway 182. From passageway 182 the fluid will flow into inlets 174 and then into reservoirs 166.

As the fluid flows into reservoirs 166, it will exert an inward pressure on the plunger end portions 170a of pusher members 170 causing them to move rearwardly of the reservoirs in the manner shown in FIG. 89. As the pusher members move rearwardly of reservoirs 166 they will exert forces on spring members 38 causing them to expand from its retracted configuration shown in FIG. 52 to their expanded configuration shown in FIGS. 89 and 90.

As the reservoirs 166 fill with fluid, any gases trapped within the reservoirs will be vented to atmosphere via vent means "V", shown here as vent ports 201 which are mounted in portion 164b of the housing (FIG. 52). These vent means can be constructed of a suitable hydrophobic porous material such as a porous plastic.

Upon opening the fluid delivery path to the fluid delivery means of the invention, which here comprises the earlier described conventional administration set 108 (FIG. 44), the stored energy means, or springs 38, will tend to return to their starting configurations thereby controllably urging fluid flow outwardly of the reservoirs via the flow control means of the invention the character of which will presently be described.

As the fluid contained within reservoirs 166 is urged outwardly thereof by the stored energy means, the fluid will flow under pressure through the reservoir outlets 174 (FIG. 52) and then on toward the flow control means, or flow control assembly of this latest form of the invention. As before, the important flow control means functions to precisely control the rate of fluid flow flowing from the reservoirs 166 toward the patient.

Referring to FIGS. 82 through 87, it can be seen that the flow control means of this latest form of the invention includes a flow rate control means, which is similar in many respects to the previously described flow rate control means and here comprises a base plate, or rate control member 214 and a mating cover member 216. Cover member 216 is provided with a fluid inlet port and 218 and a plurality of spaced apart fluid outlet ports 220a, 220b, 220c, 220d and 220e respectively. As illustrated in FIG. 87, flow rate control member, or base plate 214 is uniquely provided with a plurality of radically extending flow control channels 222a, 222b, 222c, 222d and 222e respectively, each having an inlet and an outlet. The outlets of the flow control channels are in communication with the spaced apart outlet ports of the cover member 216 and the inlet port is in fluid communication with reservoirs 166.

Also forming a part of the flow control means of this latest form of the invention is a selector knob assembly 226, which includes a uniquely configured selector knob 224 that is carried within a horizontal bore 225 formed in housing portion 164c and a control knob 227 that is adapted to mate with selector knob 224. Selector knob 224 is similar in some respects to the earlier described selector knob 126 and includes a body portion 224a and an enlarged diameter head portion 224b.

As illustrated in FIGS. 76 and 77, selector knob 224 is uniquely provided with a plurality of radically extending flow control channels 228a, 228b, 228c, 228d and 228e, each having an inlet port and an outlet port which is in fluid communication with an axially extending passageway 230. Axially extending passageway 230 is, in turn, in fluid communication with administration line 108. In a manner presently to be described, selector knob assembly 226, which comprises a part of the selector means of this latest form of the invention, functions to selectively align one of the inlets of the radially extending flow control channels of the selector knob with a selected one of the spaced apart fluid outlets 220a, 220b, 220c, 220d and 220e of the rate control housing 230 (FIG. 85).

As best seen in FIG. 91, inlet port 218 of the rate control assembly 230 is in communication with the outlet ports 174 of reservoirs 166 via a stub passageway 234 and passageway 184 with which it is in communication. As the pusher assembly 170 is urged forwardly by the stored energy means, the fluid contained within reservoirs 166 will flow through the outlet ports 174, through passageways 184 and 234 and into inlet 218 of the rate control assembly in a manner to permit each of the micro channels of the rate control plate 214 to fill with the medicinal fluid.

Rotation of the selector knob 224 and a manner presently to be described will permit each of the spaced outlets of the micro channels to selectively be aligned with a selected one of the outlet ports 220a, 220b, 220c, 220d and 124e of the rate control cover 216. The fluid can then flow into a selected one of the plurality of passages 228a, 228b, 228c, 228d and 228e formed in the rate control knob 224, into axially extending passageway 230, into the administration line and then on to the patient at a precise rate of flow. Any gases trapped within the flow rate control system can be vented to atmosphere via a vent 231 which is carried within a control knob, the character of which will presently be described.

As previously discussed, flow micro channels 222a, 222b, 222c, 222d and 222e may be of different sizes, lengths and configurations. Further, the flow control micro channels may be rectangular in cross-section, or alternatively, they can be semicircular in cross-section, U-shaped in cross-section, or they may have any other cross-sectional configuration that may be appropriate to achieve the desired fluid flow characteristics.

Figure 57:
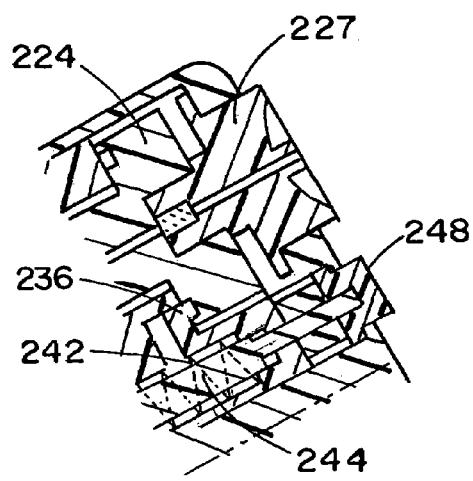
FIG. 57 is a cross-sectional view taken along lines 57-57 of FIG. 56.

To assist in rotating knob 224, the control knob 227, which is adapted to mate with knob 224, and is provided with a finger gripping bar 227a (FIG. 79). As illustrated in FIG. 78, selector knob 224 is provided with a plurality of circumferentially spaced apart indexing cavities 233 that closely receive an indexing finger 241 which forms a part of the indexing means of the invention for appropriately indexing the selector knob (FIG. 57).

Figure 66A:
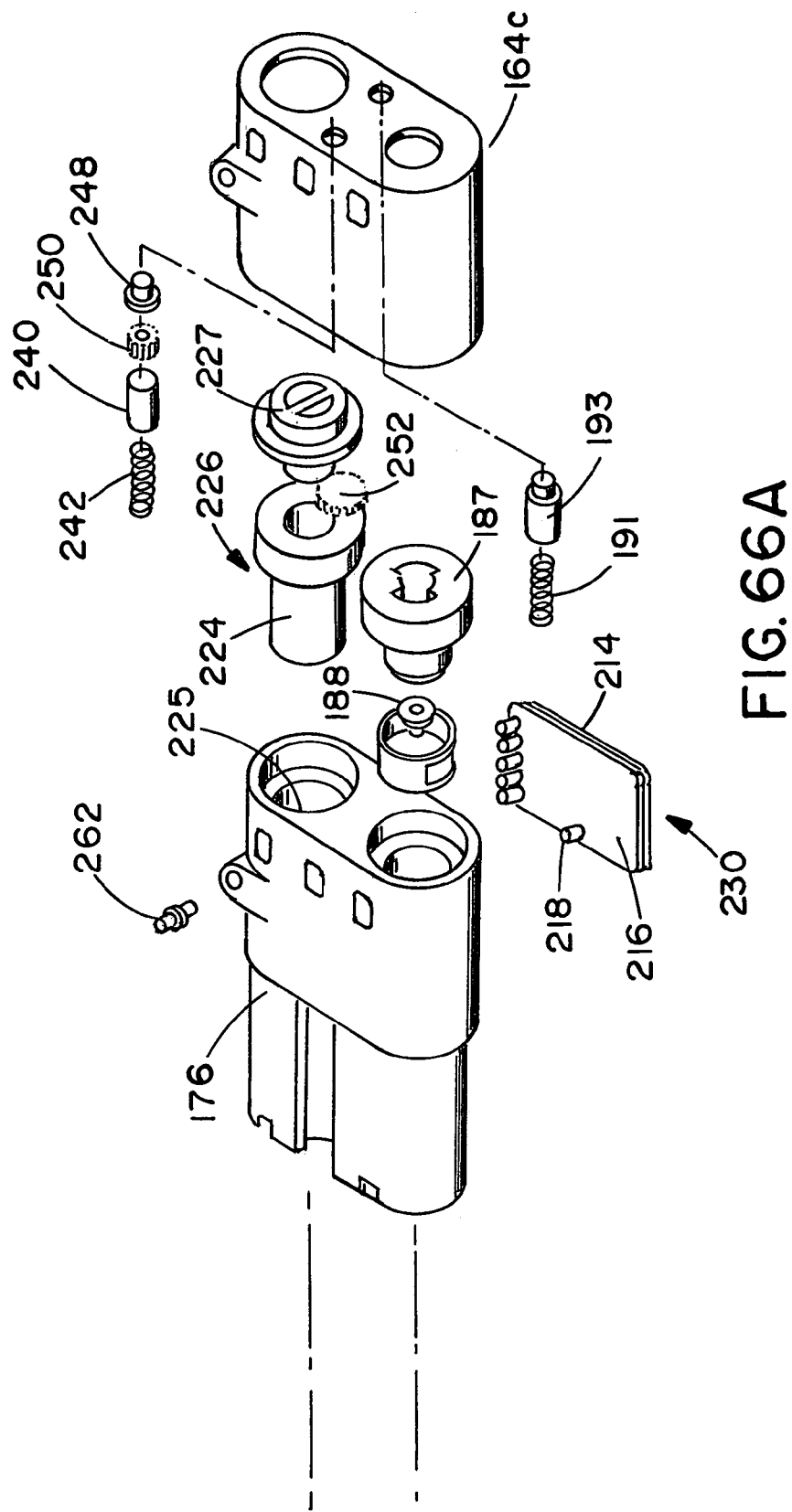
FIGS. 66A and 66B when considered together comprise a generally perspective, exploded view of the form of the delivery device of the invention illustrated in FIG. 44 (hereinafter referred to as "FIG. 66").
Figure 66B:
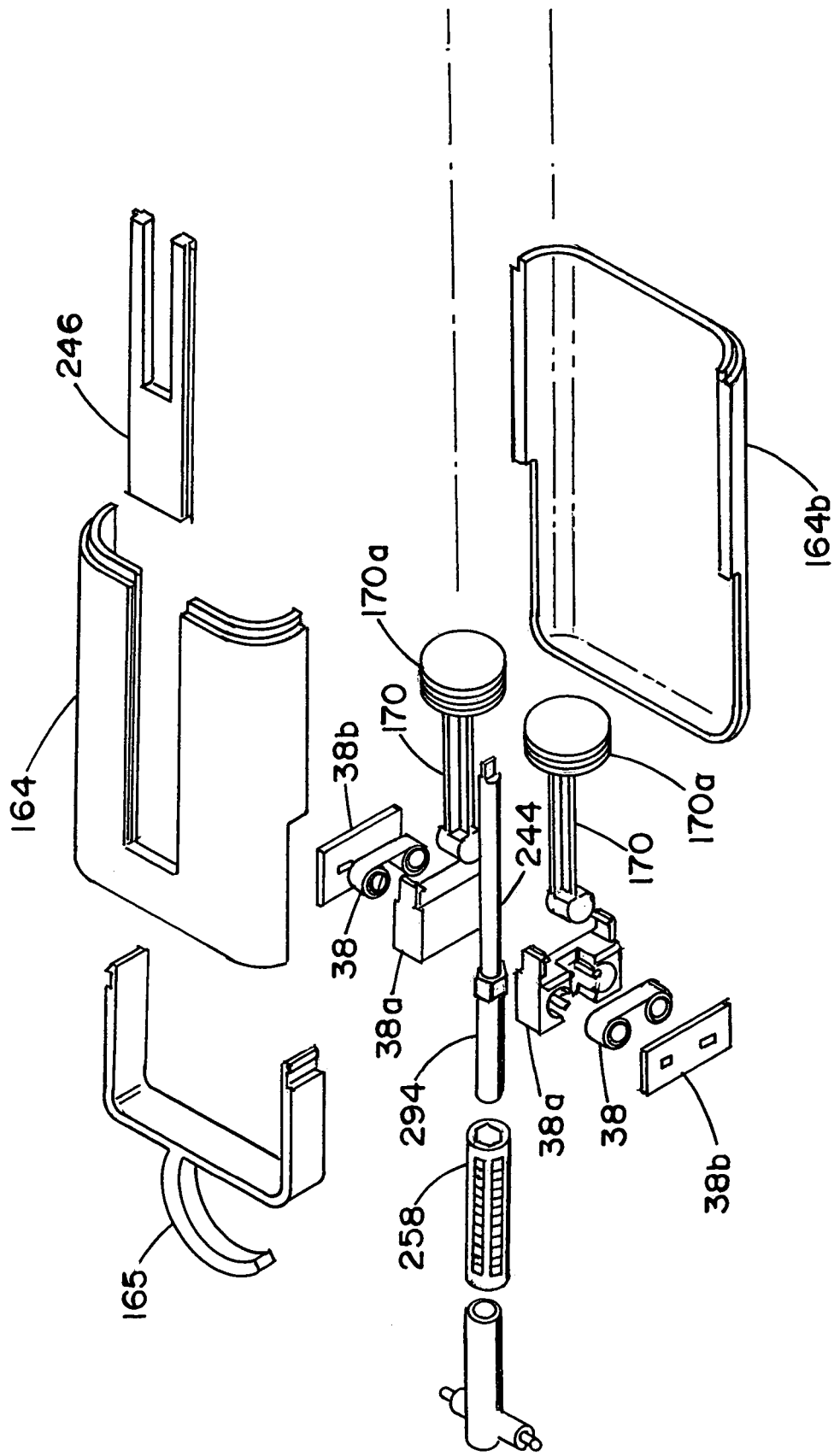
Figure 75:
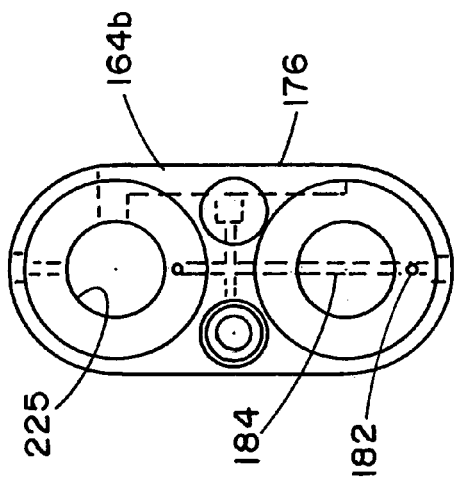
FIG. 75 is a view taken along lines 75-75 of FIG. 70.
Figure 73:
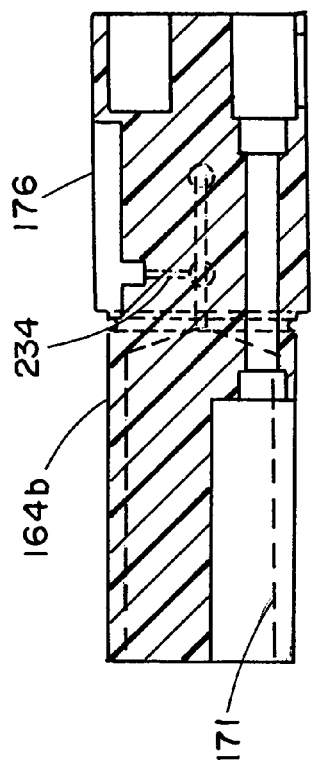
FIG. 73 is a cross-sectional view taken along lines 73-73 of FIG. 70.
Figure 74:
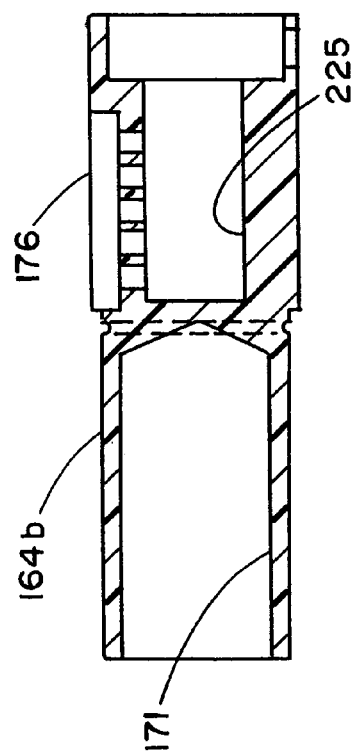
FIG. 74 is a cross-sectional view taken along lines 74-74 of FIG. 70.

Also forming a part of the flow control means of the invention is selector knob locking means for preventing rotation selector knob 224. This selector knob locking means here comprises a locking assembly 238 that includes a locking member 240 member that includes indexing finger 236 which is continuously urged into a selected one of the indexing cavities 233 formed in knob 224 by a coiled spring 242 which is carried by an elongated indicator shaft 244 (FIGS. 53 and 66). Indicator shaft 244 forms a part of the important flow-time indicating means of the apparatus of the invention. As will presently be discussed, the flow-time indicating means provides an indication of to the caregiver of the volume of medicament to be delivered to the patient over a particular period of time. The flow-time indicating means of the invention also includes an indicator plate 246 which is carried by housing 164 in the manner best seen in FIG. 45. Indicator plate 246 is provided with indicia 246a which indicates the volume of fluid to be delivered in milliliters and indicia 246b indicating the time of delivery in hours (FIG. 45).

Figure 54:
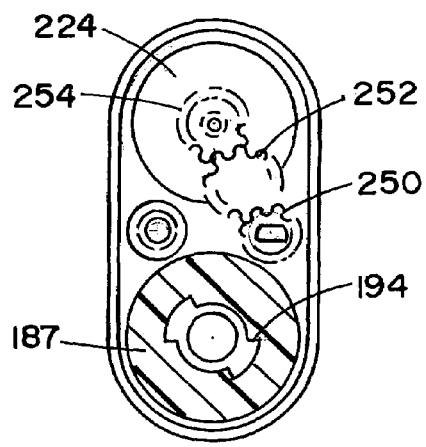
FIG. 54 is a cross-sectional view taken along lines 54-54 of FIG. 52.
Figure 55:
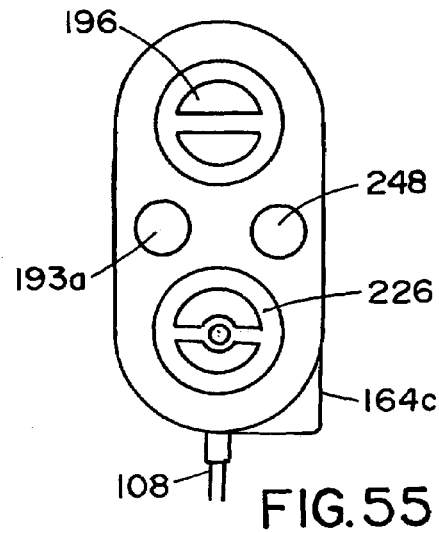
FIG. 55 is a view taken along lines 55-55 of FIG. 52.

As best seen in FIG. 53, provided proximate the forward end of indicator shaft 244 is a pushbutton 248 which extends outwardly from housing 164 and a control gear 250. Control gear 250 is mated with an idler gear 252, which, in turn, is mated with a drive gear 254 which forms a part of the flow control knob 227 (FIGS. 54, 80 and 81). With this construction, when an inward force is exerted on pushbutton 248 against the urging of spring 242, rotation of flow control knob 227 will impart rotation to selector knob 224. Rotation of control knob 227 will also impart rotation to idler gear 252 and to idler gear 250 which is interconnected with indicator shaft 244. Rotation out of indicator shaft 244 will also cause rotation of an indicator tube 258 which is carried within housing 176 proximate indicator plate 246. As the control knob 227 is rotated, selector knob 224 will rotate in a manner to bring a selected one of the radially extending passageways 228a, 228b, 228c, 228d and 228e into alignment with a selected one of the outlet ports 220a, 220b, 220c, 220d and 220e formed on rate control housing 214 thereby permitting fluid flow toward the patient through the rate control micro channel that is in communication with the selected outlet port. Indicator tube 258 is uniquely constructed so that as the selector knob 224 and the indicator shaft 244 are rotated, the indicia viewable through the indicator plate will correspond to the rate of fluid flow per hour permitted by the selected rate control micro channel which is in communication with the administration's set 108 via passageway 230 formed in the selector knob.

Figure 64:
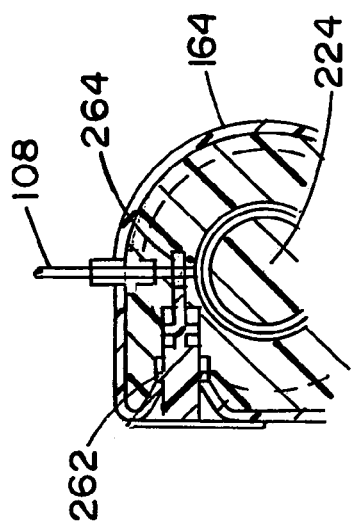
FIG. 64 is a cross-sectional view taken along lines 64-64 of FIG. 52.
Figure 65:
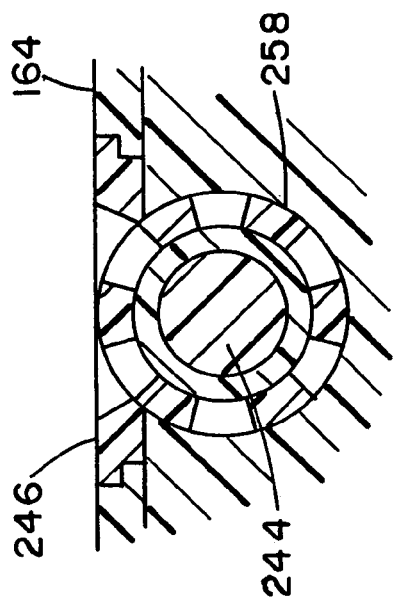
FIG. 65 is a view taken along lines 65-65 of FIG. 53.
Figure 63:
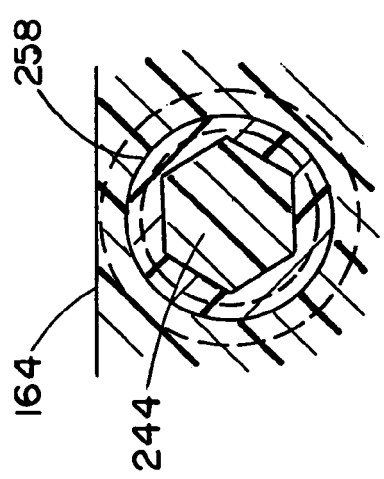
FIG. 63 is a cross-sectional view taken along lines 63-63 of FIG. 53.

Also forming an important feature of the apparatus of this latest form of the invention is disabling means for disabling the apparatus and preventing fluid flow into the administration line 108. As best seen in FIG. 64, this disabling means here comprises a shaft 262 which is carried by housing 164 and is a movable from an extended position shown in FIG. 44 to a disabling position shown in FIG. 64. Connected to shaft 262 is a reduced diameter portion 264 which, in the manner shown in FIG. 64, is adapted to block fluid flow through the outlet passageway of the device when the disabling shaft is in the disabling position shown in FIG. 64.

Figure 93:
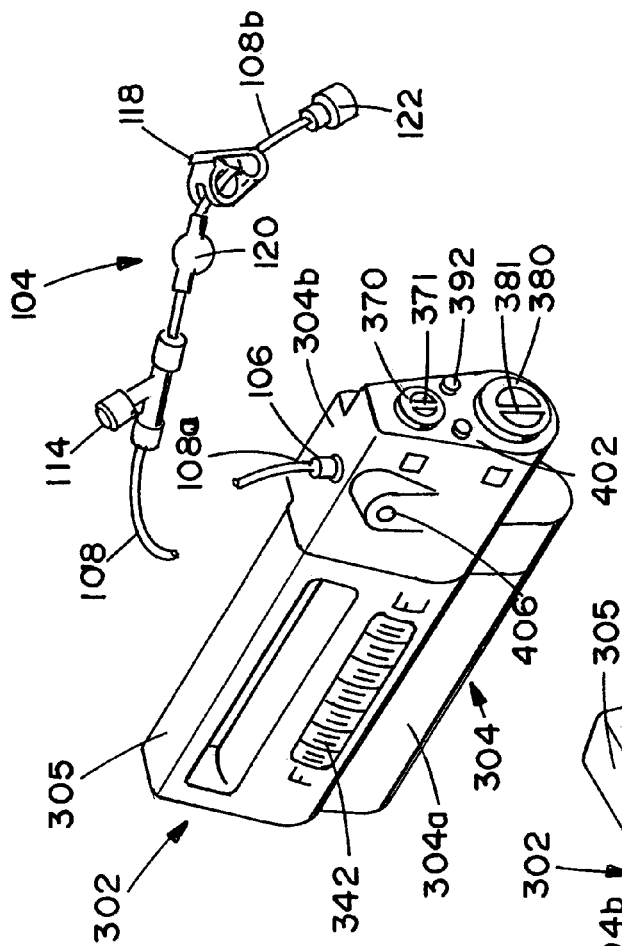
FIG. 93 is a generally perspective view of still another form of the fluid dispensing device of the present invention showing one side of the device.
Figure 94:
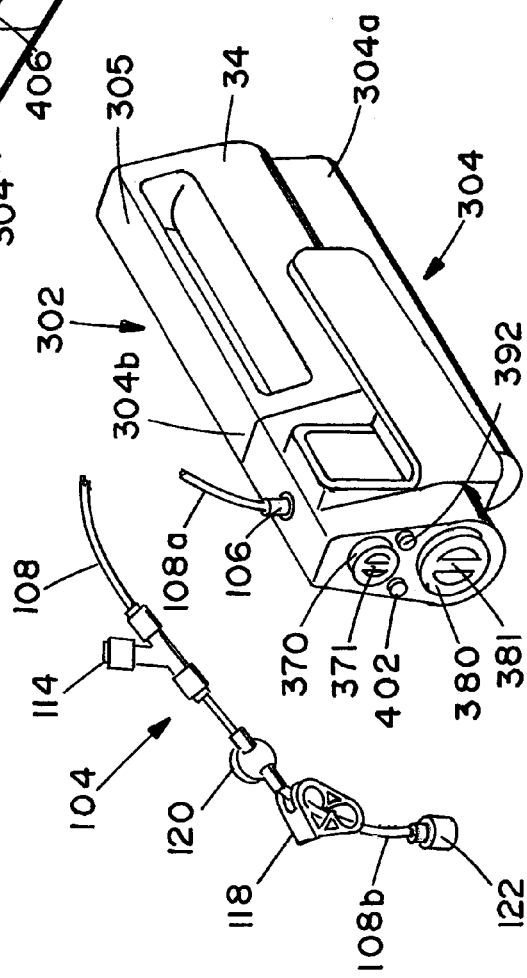
FIG. 94 is a generally perspective view of the alternate form of the fluid dispensing device showing the opposite side of the device.
Figure 104:
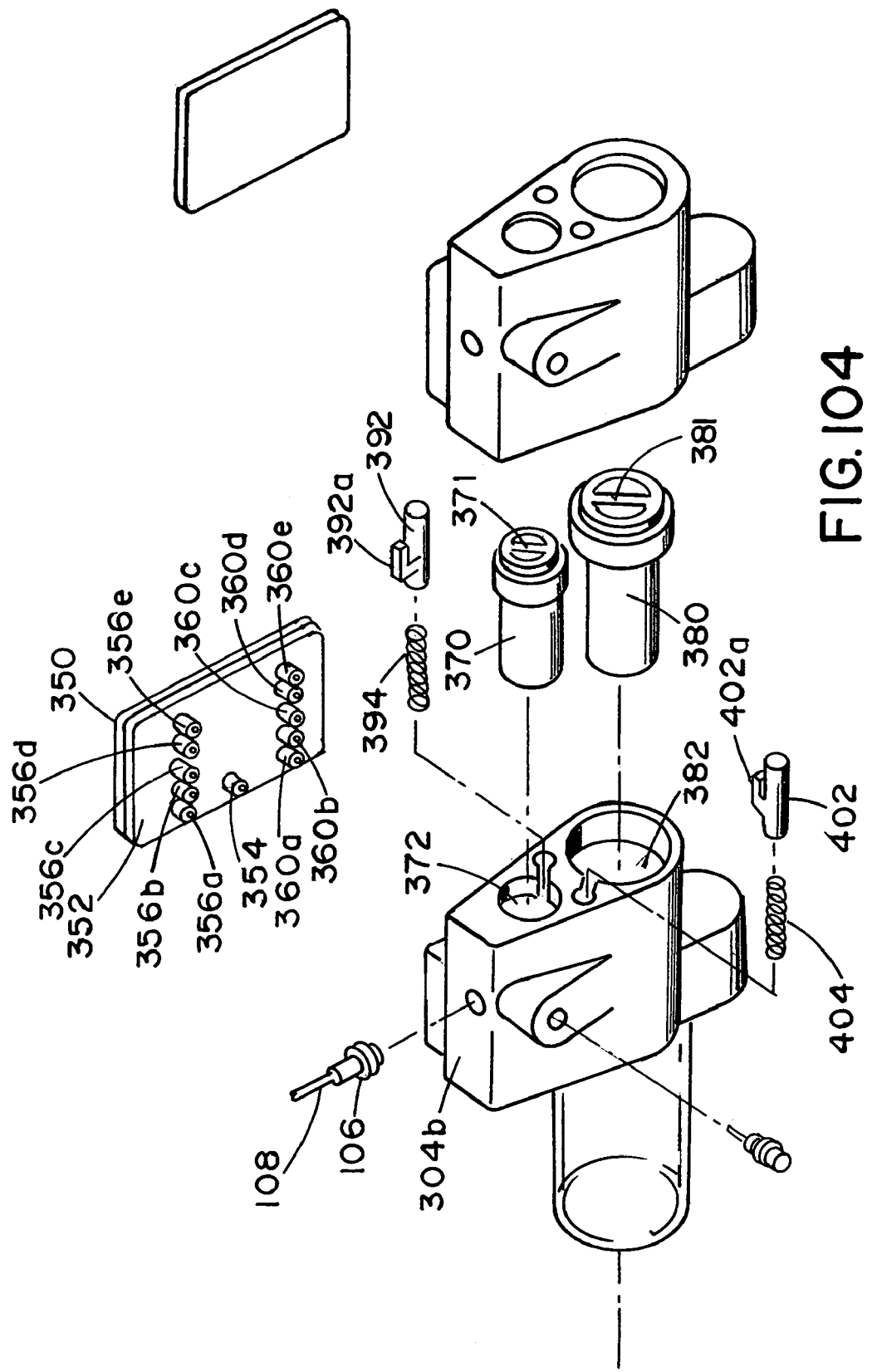
FIGS. 104 and 104A when considered together comprise a generally perspective, exploded view of the fluid-dispensing device shown in FIGS. 93 and 94 (hereinafter referred to as "FIG. 104").
Figure 104A:
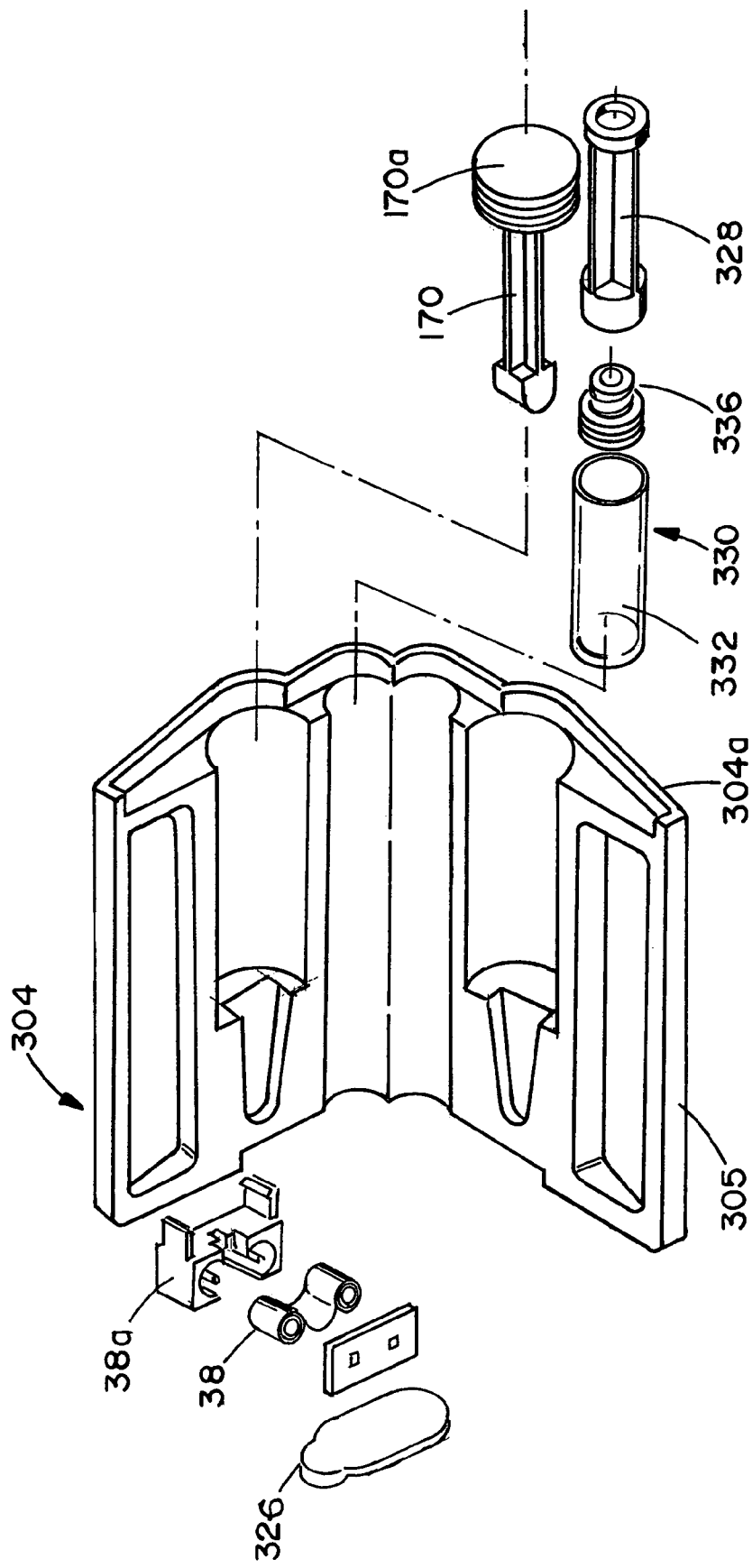

Referring next to FIGS. 93 through 114, still another form of the apparatus of the invention is there illustrated and generally designated by the numeral 302. Because this alternate form of the apparatus is similar in many respects to the apparatus previously described, like numerals are used in FIGS. 93 through 114 to identify like components. As best seen in FIGS. 93, 94 and 104, the apparatus here comprises a snap together outer housing 304 having first and second portions 304a and 304b respectively. Housing portion 304a comprises the reservoir portion while housing portion 304b comprises the rate control, fill and delivery and control portions. When snapped together the housing portions define a carrying handle 305.

Disposed within first portion 304a of outer housing 304 is the novel stored energy means of the invention for causing the fluid contained within fluid reservoir 306 to controllably flow outwardly of the housing and into the fluid dispensing means. As before, in this latest form of the invention, the stored energy means comprises a constant force spring member 38 that is carried within the first portion 304a of the outer housing. Spring member 38 is first extended by fluid flowing into reservoir 306 and then controllably retracts in the manner shown in FIG. 99 to cause fluid flow from the outer housing, through the dispensing means of the invention and toward the patient. Stored energy member, or constant force spring 38, is of similar construction and functions in a similar manner to that previously described. After the spring is extended it will tend to uniformly return toward its starting configuration and in so doing will exert a constant force on pusher member 170, which is housed within housing portion 304a in the manner shown in FIGS. 99 and 104. As the spring returns to its starting configuration, the fluid contained within the fluid reservoir 306 will be caused to flow outwardly through outlet 308 and toward the flow rate control means of the invention.

Figure 99:
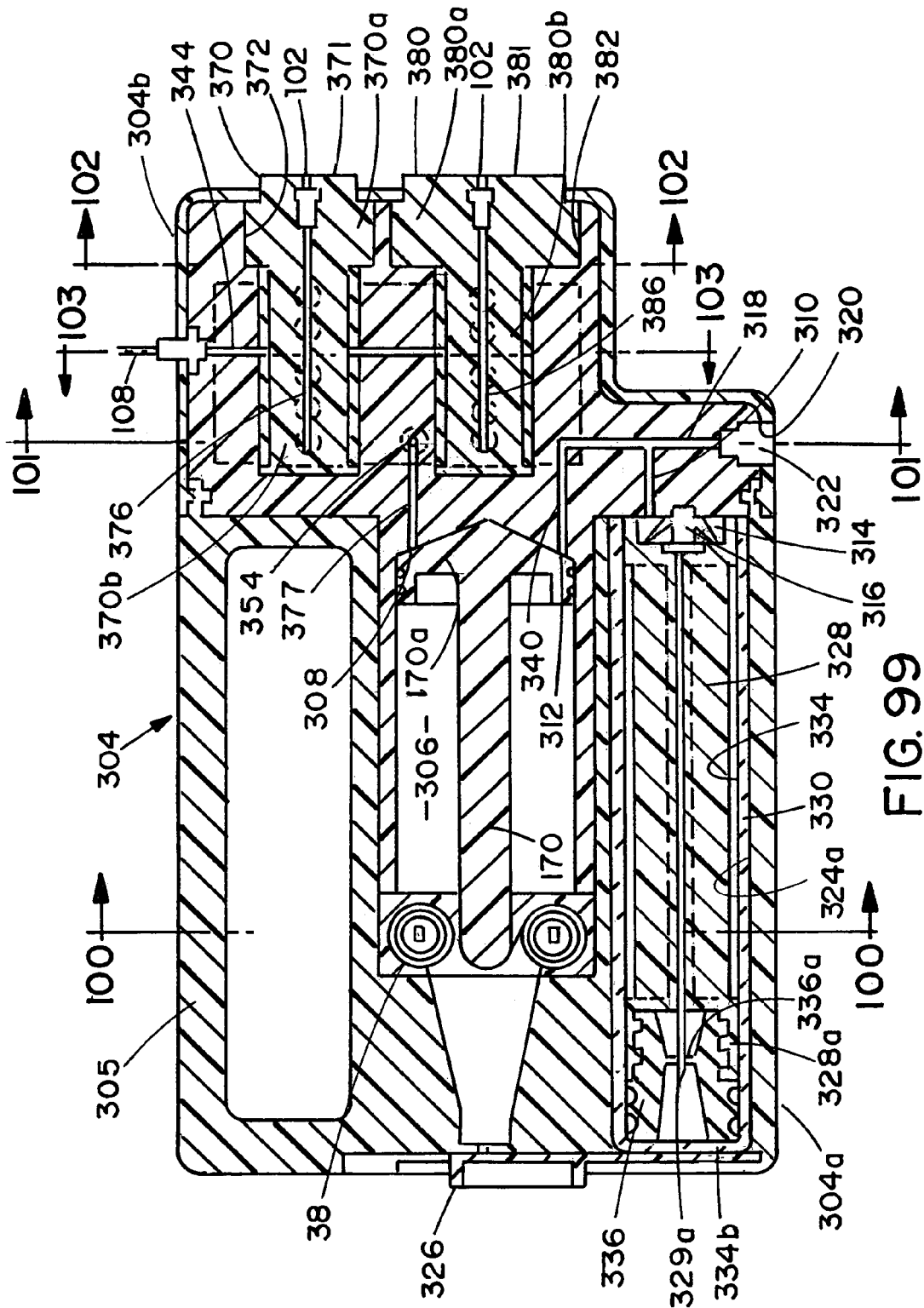
FIG. 99 is a cross-sectional view taken along lines 99-99 of FIG. 96.
Figure 100:
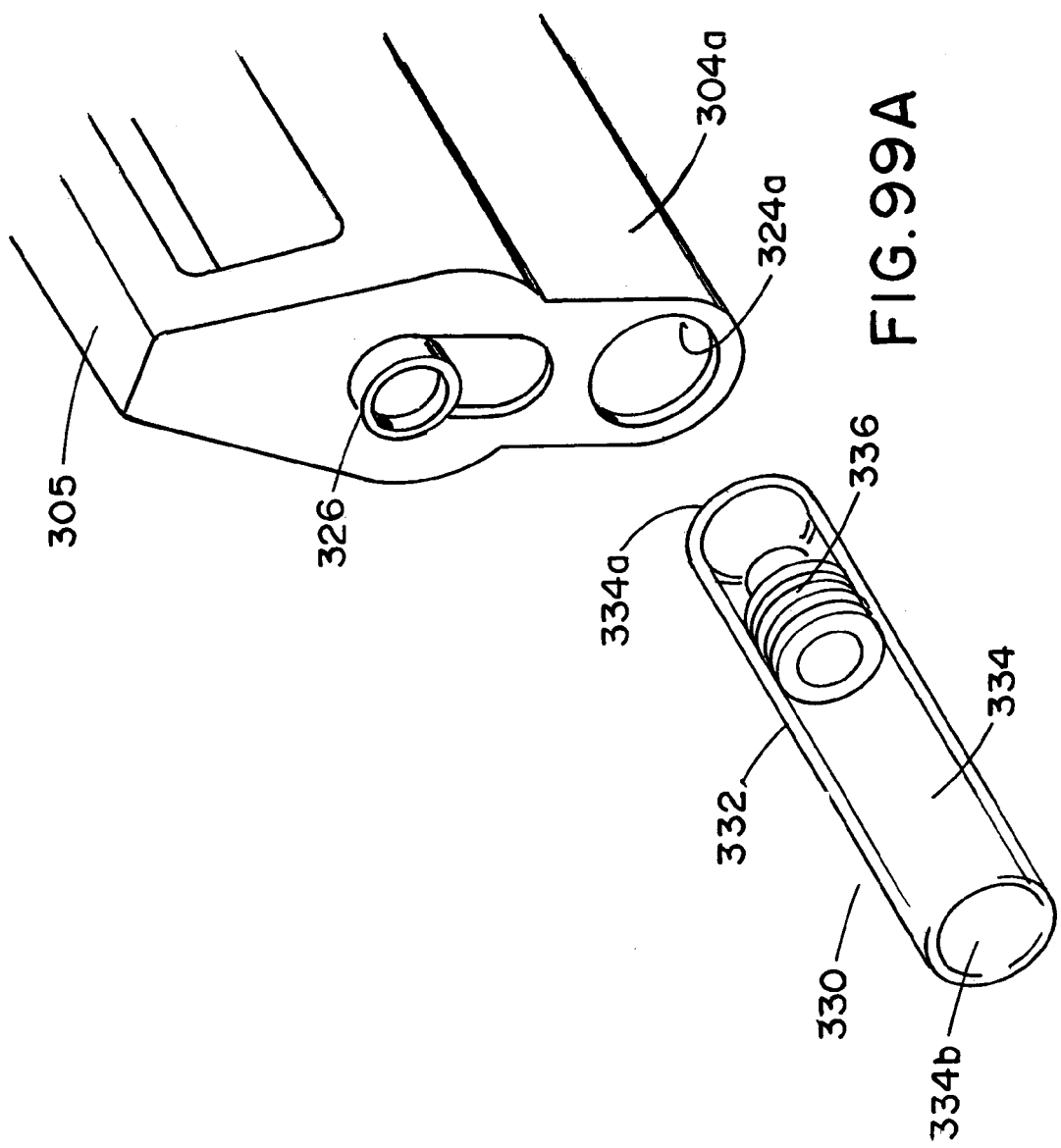
FIG. 100 a cross-sectional view taken along lines 100-100 of FIG. 99.

Forming an important aspect of the apparatus is the fill means, which is carried by the second portion 304b of outer housing 304 and functions to controllably fill the reservoir 306 with the fluid to be dispensed. As best seen in FIG. 99, housing portion 304b includes a fluid passageway 310 that communicates with inlet 312 of fluid reservoir 306. Fluid passageway 310 also communicates with a cavity 314 formed within second portion 304b of the housing. Disposed within cavity 314 is a conventional, umbrella type check valve 316 which permits fluid flow toward fill passageway 310, but blocks fluid flow in the opposite direction. Passageway 310 also communicates, via a passageway 318, with a cavity 320 that houses a pierceable septum 322, which comprises a part of one form of the fill means of the invention. Septum 322 may be a conventional slit septum, the character well understood by those skilled in the art, which is pierceable by the cannula of a filling syringe assembly (not shown) which contains the medicinal fluid to be dispensed and which, in a manner presently to be described, can be used to fill or partially fill reservoir 306 via passageway 310.

First portion 304a of housing 304 includes a connector portion 324 that is normally closed by a closure cap 326. Connector portion 324 is provided with a chamber 324a for telescopically receiving the medicament fill vial assembly of the invention the character of which will presently be described. An elongated support 328, which is mounted within chamber 324a includes a threaded end portion 328a and carries an elongated, longitudinally extending, hollow needle 329 having a central fluid flow passageway.

Referring particularly to FIG. 99a, the medicament containing fill vial assembly 330 includes a fill vial 332 having a fluid chamber 334 for containing the injectable fluid medicament. Chamber 334 is provided with a first open end 334a and second closed end 334b. First open end 334a is sealably closed by closure means here provided in the form of an externally threaded elastomeric plunger 336 which is telescopically movable within chamber 334 from a first location where the plunger is disposed proximate first open end 334a to the second, device-fill location where the plunger is disposed proximate second closed end 334b (FIG. 99).

Figure 113:
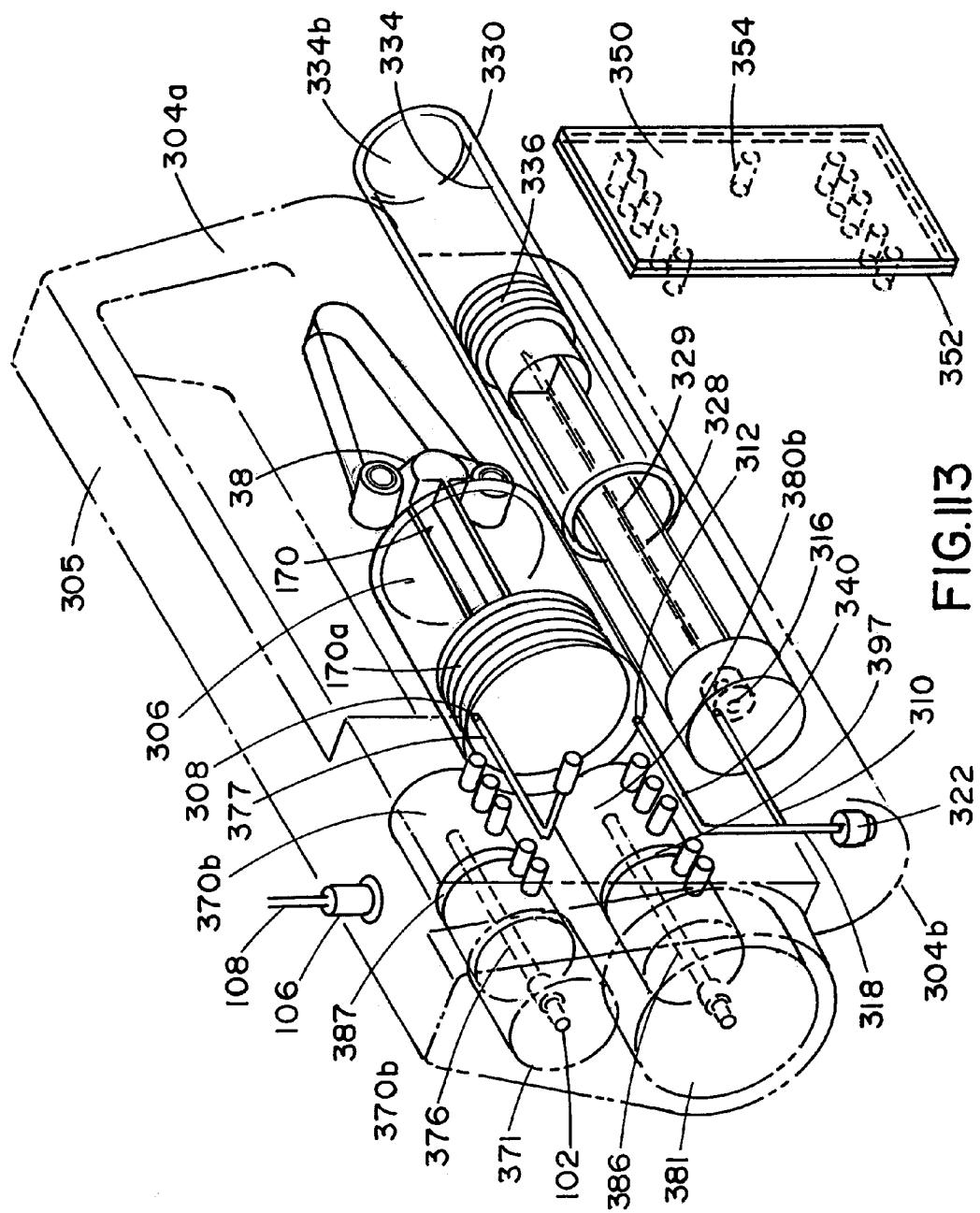

After removal of closure cap 326 from connector portion 324, vial assembly 330 can be inserted into chamber 324a (FIGS. 99, 99A and 113). As the fill vial assembly is so introduced and the plunger 336 is threadably interconnected with threaded end 328a of support 328, the sharp end 329a of the elongated needle 329 will pierce the central wall 336a of the elastomeric plunger in the manner shown in FIG. 99. An inward pressure exerted on the vial assembly will cause the vial to move inwardly of chamber 324a and will cause the structural support 328 to move the elastomeric plunger inwardly of the vial chamber 334 in a direction toward the second or closed end 334b of the vial chamber. As the plunger is moved inwardly of the vial, the fluid contained within the vial chamber will be expelled there from into the hollow elongated needle 329, which has pierced the central wall 336a of the elastomeric plunger. The fluid will then flow past conventional umbrella type check valve 316, into passageway 310 and thence into a passageway 340 which communicates with reservoir inlet 312. (see also FIG. 113)

As the fluid flows into reservoir 306, it will exert an inward pressure on the plunger end portion 170a of pusher member 170 causing it to move rearwardly of reservoir 306. As the pusher member moves rearwardly it will exert forces on spring member 38 causing it to it to expand from its retracted configuration shown in FIG. 99 to its expanded configuration. This rearward movement of pusher member 170 can be viewed through the volume indicator window 342 indicating that the reservoir has changed from an empty configuration to a filled configuration (FIG. 93).

As the reservoir 306 fills with fluid, any gases trapped within the reservoir will be vented to atmosphere via vent means "V", mounted in portion 304b of the housing. This vent means here comprises a gas vent 102 that can be constructed of a suitable hydrophobic porous material such as a porous plastic.

Upon opening the fluid delivery path to the fluid delivery means of the invention, shown here as a conventional administration set 104 (FIG. 93), the stored energy means, or spring 38, will tend to return to its starting configuration thereby controllably urging fluid flow outwardly of reservoir 306 via the flow control means of the invention the character of which will presently be described.

Administration set 104 is connected to the second portion 304b of housing 304 by a connector 106 in the manner shown in FIG. 93 of the drawings. The proximal end 108a of administration line 108 of the administration set is in communication with an outlet fluid passageway 344 which is formed in housing portion 304b in the manner best seen in FIG. 99. Disposed between the proximal end 108a and the distal end 108b of the administration line are a conventional gas vent and filter 120. Provided at the distal end 108b is a luer connector 122 of conventional construction (FIG. 1).

A number of beneficial agents can be contained within vial 332 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

As the fluid contained within reservoir 306 is urged outwardly thereof by the stored energy means, the fluid will flow under pressure through reservoir outlet 308 (FIG. 99) and then on toward the flow control means, or flow control assembly of this latest form of the invention. As before, the important flow control means functions to precisely control the rate of fluid flow flowing from the reservoir 306 toward the patient.

Referring to FIGS. 105 through 112, it can be seen that the flow control means of this latest form of the invention comprises a flow rate control means, which is similar in many respects to the previously described flow rate control means and here comprises an assembly 351 which includes a base plate, or rate control member 350 and a mating cover member 352. Cover member 352 is provided with a fluid inlet port 354 and a plurality of spaced apart, generally tubular shaped micro rate fluid outlet ports 356a, 356b, 356c, 356d and 356e respectively. As illustrated in FIG. 105, flow rate control member, or base plate 350 is uniquely provided with a plurality of micro rate flow control channels 358a, 358b, 358c, 358d and 358e respectively, each having an inlet and an outlet. In the manner indicated in FIG. 110, the outlets of the micro rate flow control channels are in communication with the spaced apart micro rate outlet ports of the cover member 350 and the inlet port is in fluid communication with reservoirs 306. Cover member 352 is also provided with a plurality of spaced apart, generally tubular shaped macro rate fluid outlet ports 360a, 360b, 360c, 360d and 360e respectively. Flow rate control member, or base plate 350 is also uniquely provided with a plurality of macro rate flow control channels 362a, 362b, 362c, 362d and 362e respectively, each having an inlet and an outlet. The outlets of the macro rate flow control channels are in communication with the spaced apart macro rate outlet ports of the cover member 350.

As indicated in FIG. 109, inlet port 354 is provided with a filter member 365 of conventional construction for filtering particulates from the fluid flowing toward the various rate control channels.

Also forming a part of the flow control means of this latest form of the invention is a micro rate selector knob 370 that is carried within a horizontal bore 372 formed in housing portion 304b. Selector knob 370 includes a body portion 370b and an enlarged diameter head portion 370a. As illustrated in FIGS. 99, 103A and 103B, selector knob 370 is uniquely provided with a plurality of radially extending flow control channels 374a, 374b, 374c, 374d and 374e, each having an inlet port and an outlet port which is in fluid communication with an axially extending passageway 376. Axially extending passageway 376 is, in turn, in fluid communication with administration line 108. In a manner presently to be described, micro selector knob, which comprises a part of the selector means of this latest form of the invention, functions to selectively align one of the inlets of the radially extending flow control channels of the selector knob with a selected one of the spaced apart micro rate fluid outlets 356a, 356b, 356c, 356d and 356e of the rate control housing 352 (FIGS. 103B and 103C).

Also forming a part of the flow control means of this latest form of the invention is a macro rate selector knob 380 that is carried within a horizontal bore 382 formed in housing portion 304b. Selector knob 380 includes an enlarged diameter head portion 380a and a generally cylindrical body portion 380b. As illustrated in FIG. 103D, selector knob 380 is uniquely provided with a plurality of radially extending flow control channels 384a, 384b, 384c, 384d and 384e, each having an inlet port and an outlet port which it is in fluid communication with an axially extending passageway 386. Axially extending passageway 386 is, in turn, in fluid communication with administration line 108.

In a manner presently to be described, selector knob 380, which also comprises a part of the selector means of this latest form of the invention, functions to selectively align one of the inlets of the radially extending flow control channels of the macro selector knob with a selected one of the spaced apart macro rate fluid outlets 360a, 360b, 360c, 360d and 360e of the rate control housing 352 (FIG. 107).

Figure 114:
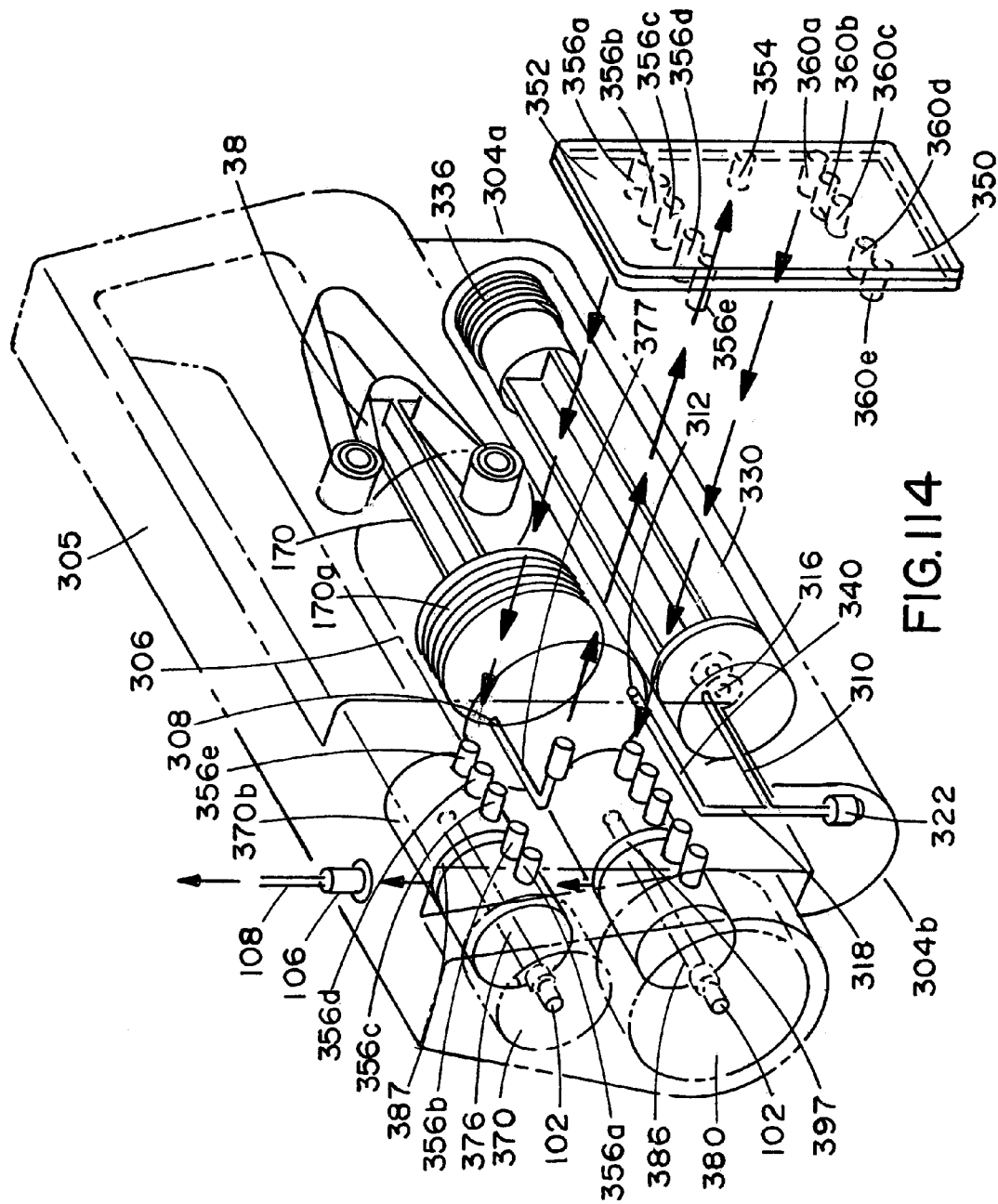

As best seen in FIGS. 99 and 114, inlet port 354 of the rate control assembly is in communication with the outlet port 308 of reservoir 306 via a passageway 377 with which it is in communication. As the pusher assembly 170 is urged forwardly by the stored energy means, the fluid contained within reservoirs 306 will flow through the outlet port 308, through passageway 377 and into inlet 354 of the rate control assembly in a manner to permit each of the micro channels and each of the macro channels of the rate control plate 350 to fill with the medicinal fluid to be dispensed to the patient.

In using the apparatus, rotation of the micro rate selector knob 370 will permit each of the spaced outlets of the micro channels to selectively be aligned with a selected one of the outlets 356a, 356b, 356c, 356d and 356e of the rate control cover 352. The fluid can then flow into a selected one of the plurality of passages 374a, 374b, 374c, 374d and 374e, formed in the micro rate selector knob 370, into axially extending passageway 376, into the administration line via a circumferentially extending fluid flow passageway 387 (see FIGS. 103, 103C and 114), into the administration line 108 and then on to the patient at a precise micro rate of flow. To assist in rotating knob 370, the knob is provided with a finger gripping bar 371 (FIG. 93).

As shown in FIG. 103A, selector knob 370 is provided with a plurality of circumferentially spaced apart indexing cavities 390 that closely receive the end of an indexing finger 402a of an outwardly extending locking arm 402 which forms a part of the flow control means of the invention and functions to prevent rotation selector knob 370. (FIGS. 102 and 104). Finger 402a is continuously urged into a selected one of the indexing cavities 390 formed in knob 370 by a coiled spring 404 (FIGS. 97 and 104).In order to permit rotation of knob 370, arm 404 must be pushed inwardly against the urging of spring 404.

In a similar manner, rotation of the macro rate selector knob 380 will permit each of the spaced outlets of the macro channels to selectively be aligned with a selected one of the outlets 360a, 360b, 360c, 360d and 360e of the rate control cover 352. The fluid can then flow into a selected one of the plurality of passages 384a, 384b, 384c, 384d and 384e formed in the micro rate selector knob 380, into axially extending passageway 386, into the administration line via a circumferentially extending fluid flow passageway 397 (see FIGS. 103D and 114), and then on to the patient at a precise macro rate of flow. To assist in rotating knob 380, the knob is provided with a finger gripping bar 381 (FIG. 93).

As shown in FIG. 103D, selector knob 380 is provided with a plurality of circumferentially spaced apart indexing cavities 399 that closely receive the end of an indexing finger 392a of an outwardly extending locking arm 392, which forms a part of the flow control means of the invention and functions to prevent rotation selector knob 380. (FIGS. 97, 98, 102 and 104). Finger 392a is continuously urged into a selected one of the indexing cavities 399 formed in knob 380 by a coiled spring 404 (FIGS. 97 and 104). In order to permit rotation of knob 380, arm 392 must be pushed inwardly against the urging of spring 394.

The apparatus of this latest form of the invention also includes disabling means for irrevocably disabling the device and rendering it inert. Referring to FIGS. 93, 96 and 103, this disabling means here comprises a disabling shaft 406 that is telescopically movable within a passageway 408 formed within housing portion 304b. As best seen in FIG. 96, shaft 406 has a distal end 406a, which, upon insertion of the shaft distal end into passageway 344, will block fluid flow through the passageway. A friction fit retainer 409 normally holds shaft 406 in the retracted position.

Referring next to FIGS. 115 and 116 still another embodiment of the apparatus of the invention is there illustrated and generally designated by the numeral 412. This apparatus is similar in some respects to the apparatus shown in FIGS. 99 through 114 and like numerals are used in FIGS. 115 and 116 to identify like components. As best seen in FIG. 115, the primary difference between this latest form of the invention and that shown in FIGS. 99 through 114 concerns the provision of a differently configured reservoir fill means for filling the device reservoir. More particularly, as will presently be described in greater detail, this alternate form of fill means comprises two fill vials or containers, rather than one.

As illustrated in FIG. 115, the apparatus here comprises a snap together outer housing 414 having first and second portions 414a and 414b respectively. Housing portion 414a comprises the reservoir portion while housing portion 414b comprises the rate control, fill and delivery and control portions. When snapped together the housing portions define a carrying handle 415.

Disposed within first portion 414a of outer housing 414 is the novel stored energy means of the invention for causing the fluid contained within fluid reservoir 416 to controllably flow outwardly of the housing and into the fluid dispensing means. As before, in this latest form of the invention, the stored energy means comprises a constant force spring member 38 that is carried within the first portion 414a of the outer housing. Spring member 38 first extends due to fluid flowing into reservoir 416 and then controllably retracts in the manner shown in FIG. 115 to cause fluid flow from the device reservoir, through the dispensing means of the invention and toward the patient. Stored energy member, or constant force spring 38, is of similar construction and functions in a similar manner to that previously described. After the spring is extended it will tend to uniformly return toward its starting configuration and in so doing will exert a constant force on pusher member 170, which is housed within housing portion 414b in the manner shown in FIG. 115. As the spring returns to its starting configuration, the fluid contained within the fluid reservoir 416 will be caused to flow outwardly through outlet 416a and toward the flow rate control means of the invention.

With regard to the fill means of this latest form of the invention, which is also carried by first portion 414a of the outer housing, this important fill means functions to fill the reservoir 416 with the fluid to be dispensed. This fill means here comprises the previously described septum fill means, which is identical to that previously described, and also includes a vial fill means which includes two, rather than the one, fill vial or fill containers.

As to the septum fill means, as illustrated in FIG. 115, second housing portion 414b includes a fluid passageway 420 which is in communication with inlet 422 of fluid reservoir 416. Proximate its lower end 420a, fluid passageway 420 communicates with a cavity 424 formed within the second housing portion. Disposed within cavity 424 is a pierceable septum 426 that comprises a part of the septum fill means of this latest form of the invention. As before, septum 426 is pierceable by the needle of the syringe which contains the medicinal fluid to be dispensed and which can be used in a conventional manner to fill or partially fill reservoir 416 via passageway 422.

First portion 414a of the housing also includes a first chamber 428 for telescopically receiving a first medicament containing fill vial 330 and a second chamber 430 for receiving a second identical medicament containing vial also designated by the numeral 330. The fill vials 330 are of identical construction to vial 330 of the earlier described embodiment. Telescopically receivable within each of the fluid chambers of the vials are elongated supports 432. Each of the elongated supports 432 has an integrally threaded end portion 432a and each carries a longitudinally extending, elongated hollow needle 434. Each of the hollow needles 434 has a flow passageway that communicates with a fluid passageway 420 provided in housing portion 414b (FIG. 115). First chamber 428, second chamber 430, elongated supports 432 and hollow needles 434 together comprise the alternate form of the vial fill means of the apparatus of this latest form of the invention. Hollow needles 434 also communicate with a cavities 435 formed within second portion 414b of the housing so that as the fluid contained within the vial reservoirs is urged outwardly thereof by pushers 432 and into needles 434, fluid will flow into cavities 435. Disposed within each cavity is a conventional, umbrella type check valve 316 which permits fluid flow toward fill passageway 420, but blocks fluid flow in the opposite direction.

A number of beneficial agents can be contained within vials 430 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Forming another very important aspect of the apparatus of this latest form of the invention is a novel flow control means that are carried by second portion 414b of outer housing 414. This flow control means, which is identical in construction and operation to that described in connection with the embodiment of the invention shown in FIGS. 99 through 114, functions to precisely control the rate outwardly of fluid flow from reservoir 416 and toward the patient. This flow control means here comprises an assembly 351 (FIGS. 108 and 116) which includes a base plate, or rate control member 350 and a mating cover member 352. Cover member 352 is provided with a fluid inlet port 354 and a plurality of spaced apart, generally tubular shaped micro rate fluid outlet ports 356a, 356b, 356c, 356d and 356e respectively. As illustrated in FIG. 105, flow rate control member, or base plate 350 is uniquely provided with a plurality of micro rate flow control channels 358a, 358b, 358c, 358d and 358e respectively, each having an inlet and an outlet. In the manner indicated in FIG. 110, the outlets of the micro rate flow control channels are in communication with the spaced apart micro rate outlet ports of the cover member 350 and the inlet port is in fluid communication with reservoir 416. Cover member 352 is also provided with a plurality of spaced apart, generally tubular shaped macro rate fluid outlet ports 360a, 360b, 360c, 360d and 360e respectively. Flow rate control member, or base plate 350 is also uniquely provided with a plurality of macro rate flow control channels 362a, 362b, 362c, 362d and 362e respectively, each having an inlet and an outlet (FIG. 105). The outlets of the macro rate flow control channels are in communication with the spaced apart macro rate outlet ports of the cover member 350.

Also forming a part of the flow control means of this latest form of the invention is a micro rate selector knob 370 that is carried within a horizontal bore 372 formed in housing portion 414b. As before, selector knob 370 includes a body portion 370a and an enlarged diameter head portion 370b. As illustrated in FIGS. 99, 103A and 103B, selector knob 370 is uniquely provided with a plurality of radially extending flow control channels 374a, 374b, 374c, 374d and 374e, each having an inlet port and an outlet port which is in fluid communication with an axially extending passageway 376. Axially extending passageway 376 is, in turn, in fluid communication with administration line 108, which is also identical in construction and operation to that shown in FIGS. 99 through 114. As earlier described, the micro selector knob functions to selectively align one of the inlets of the radially extending flow control channels of the selector knob with a selected one of the spaced apart micro rate fluid outlets 356a, 356b, 356c, 356d and 356e of the rate control housing 350 (FIGS. 103B and 103C).

Also forming a part of the flow control means of this latest form of the invention is a macro rate selector knob 380 that is carried within a horizontal bore 382 formed in housing portion 414b. Selector knob 380 includes an enlarged diameter head portion 380a and a generally cylindrical body portion 380b. As illustrated in FIG. 103D, selector knob 380 is uniquely provided with a plurality of radially extending flow control channels 384a, 384b, 384c, 384d and 384e, each having an inlet port and an outlet port which it is in fluid communication with an axially extending passageway 386. Axially extending passageway 386 is, in turn, in fluid communication with administration line 108.

As before, selector knob 380 functions to selectively align one of the inlets of the radially extending flow control channels of the macro selector knob with a selected one of the spaced apart macro rate fluid outlets 360a, 360b, 360c, 360d and 360e of the rate control housing 350 (FIG. 107).

As best seen in FIG. 115, inlet port 354 of the rate control assembly is in communication with the outlet port 416a of reservoir 416 via a passageway 441 with which it is in communication. As the pusher assembly 170 is urged forwardly by the stored energy means, the fluid contained within reservoir 416 will flow through the outlet port 416a, through passageway 441 and into inlet 354 of the rate control assembly in a manner to permit each of the micro channels and each of the macro channels of the rate control plate 350 to fill with the medicinal fluid to be dispensed to the patient.

In using the apparatus of this latest form of the invention, rotation of the micro rate selector knob 370 will permit each of the spaced outlets of the micro channels to selectively be aligned with a selected one of the outlets 356a, 356b, 356c, 356d and 356e of the rate control cover 352. The fluid can then flow into a selected one of the plurality of passages 374a, 374b, 374c, 374d and 374e, formed in the micro rate selector knob 370, into axially extending passageway 376, into the administration line via a circumferentially extending fluid flow passageway 387 (see FIGS. 103, 103C and 114), into the administration line 108 and then on to the patient at a precise micro rate of flow.

As before, selector knob 370 is provided with a plurality of circumferentially spaced apart indexing cavities that closely receive the end of an indexing finger 392a of an outwardly extending locking arm 392 (FIG. 116) which forms a part of the flow control means of the invention and functions to prevent rotation selector knob 370. (see also FIGS. 102 and 104). Finger 392a is continuously urged into a selected one of the indexing cavities 390 formed in knob 370 by a coiled spring 394 (FIGS. 97, 104 and 116). As before, in order to permit rotation of knob 370, arm 392 must be pushed inwardly against the urging of spring 394.

In a similar manner, rotation of the macro rate selector knob 380 will permit each of the spaced outlets of the macro channels to selectively be aligned with a selected one of the outlets 360a, 360b, 360c, 360d and 360e of the rate control cover 352. The fluid can then flow into a selected one of the plurality of passages 384a, 384b, 384c, 384d and 384e formed in the micro rate selector knob 380, into axially extending passageway 386, into the administration line via a circumferentially extending fluid flow passageway 397 (see FIGS. 103 and 114), and then on to the patient at a precise macro rate of flow.

As shown in FIG. 103D, selector knob 380 is also provided with a plurality of circumferentially spaced apart indexing cavities 399 that closely receive the end of an indexing finger 402a of an outwardly extending locking arm 402 (FIG. 116), which forms a part of the flow control means of the invention and functions to prevent rotation selector knob 380 (FIGS. 97, 98, 102, 104 and 116). Finger 402a is continuously urged into a selected one of the indexing cavities 399 formed in knob 380 by a coiled spring 404 (FIGS. 97, 104 and 116). In order to permit rotation of knob 380, arm 402 must be pushed inwardly against the urging of spring 404.

The apparatus of this latest form of the invention also includes disabling means for irrevocably disabling the device and rendering it inert. This disabling means is identical in construction and operation to that described in connection with FIGS. 99 through 114.

Turning to FIGS. 117 and 118 yet another embodiment of the apparatus of the invention is there illustrated and generally designated by the numeral 452. This apparatus is also similar in some respects to the apparatus shown in FIGS. 99 through 114 and like numerals are used in FIGS. 117 and 118 to identify like components. As best seen in FIG. 117, the primary difference between this latest form of the invention and that shown in FIGS. 99 through 114 concerns the provision of a differently configured reservoir fill means for filling the device reservoir. More particularly, as will presently be described in greater detail, this alternate form of fill means comprises a cartridge fill vial or container 454, having a hollow glass or plastic body portion that defines a fluid chamber that is closed by a pierceable, elastomeric septum.

As best seen in FIG. 117, the apparatus here comprises a snap together outer housing 456 having a first and second portions 456a and 456b respectively. Housing portion 456a comprises the reservoir portion while housing portion 456b comprises the rate control, fill and delivery and control portions. When snapped together the housing portions define a carrying handle 457.

Disposed within first portion 456a of outer housing 456 is the novel stored energy means of the invention for causing the fluid contained within fluid reservoir 460 to controllably flow outwardly of the housing and into the fluid dispensing means. As before, in this latest form of the invention, the stored energy means comprises a constant force spring member 38 that is carried within the first portion 456a of the outer housing. Spring member 38 first extends due to fluid flowing into reservoir 460 and then controllably retracts in the manner shown in FIG. 117 to cause fluid flow from the device reservoir, through the dispensing means of the invention and toward the patient. Stored energy member, or constant force spring 38, is of similar construction and functions in a similar manner to that previously described. After the spring is extended it will tend to uniformly return toward its starting configuration and in so doing will exert a constant force on pusher member 170, which is housed within housing portion 456*a* in the manner shown in FIG. 117. As the spring returns to its starting configuration, the fluid contained within the fluid reservoir 460 will be caused to flow outwardly through outlet 462 and toward the flow rate control means of the invention.

With regard to the fill means of this latest form of the invention, which is also carried by the outer housing, this important fill means functions to fill the reservoir 460 with the fluid to be dispensed. This fill means here comprises the previously described septum fill means, which is identical to that previously described, and also includes a vial fill means which includes the cartridge type fill vial or fill container 454.

As to the septum fill means, as illustrated in FIG. 117, second housing portion 456*b* includes a fluid passageway 464 which is in communication with inlet 466 of fluid reservoir 460. Proximate its lower end 464*a*, fluid passageway 464 communicates with a cavity 468 formed within the second housing portion. Disposed within cavity 468 is a pierceable septum 470 that comprises a part of the septum fill means of this latest form of the invention. As before, septum is pierceable by the needle of the syringe (not shown) which contains the medicinal fluid to be dispensed and which can be used in a conventional manner to fill or partially fill reservoir 460 via passageway 464.

As shown in FIG. 117, cartridge fill vial 454 comprises a hollow glass or plastic body portion 470 that defines a fluid chamber 472. Fill vial 454 has an open first end 454*a* and a second end 454*b* that is closed by a pierceable, elastomeric septum 474. An elastomeric plunger 478 is reciprocally movable within fluid chamber 472. As shown in FIG. 117, a hollow needle 479 is mounted within second portion 456*b* of the device housing and is located proximate the inboard end of chamber 472. Hollow needle 479 is adapted to pierce septum 474 when the fill vial is inserted into a chamber 480 provided in housing portion 456*a* and pushed into the position shown in FIG. 117 by the pusher means, or pusher assembly 477. Hollow needle 479 also communicates with a cavity 480 formed within second portion 456*b* of the housing so that as the fluid contained within the vial reservoirs is urged outwardly thereof by pusher 477*a* of the pusher assembly 477 fluid will flow into cavity 480. Disposed within cavity 480 is a conventional, umbrella type check valve 316 which permits fluid flow toward fill passageway 464, but blocks fluid flow in the opposite direction.

A number of beneficial agents can be contained within vial 454 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Forming another very important aspect of the apparatus of this latest form of the invention is a novel flow control means that are carried by second portion 456*b* of outer housing 456. This flow control means, which is identical in construction and operation to that described in connection with the embodiment of the invention shown in FIGS. 99 through 114, functions to precisely control the rate outwardly of fluid flow from reservoir 460 and toward the patient. This flow control means here comprises an assembly 351 (FIGS. 108 and 118) which includes a base plate, or rate control member 350 and a mating cover member 352. Cover member 352 is provided with a fluid inlet port 354 and a plurality of spaced apart, generally tubular shaped micro rate fluid outlet ports 356*a*, 356*b*, 356*c*, 356*d* and 356*e* respectively. As illustrated in FIG. 105, flow rate control member, or base plate 350 is uniquely provided with a plurality of micro rate flow control channels 358*a*, 358*b*, 358*c*, 358*d* and 358*e* respectively, each having an inlet and an outlet. In the manner indicated in FIG. 110, the outlets of the micro rate flow control channels are in communication with the spaced apart micro rate outlet ports of the cover member 350 and the inlet port is in fluid communication with reservoir 460. Cover member 352 is also provided with a plurality of spaced apart, generally tubular shaped macro rate fluid outlet ports 360*a*, 360*b*, 360*c*, 360*d* and 360*e* respectively. Flow rate control member, or base plate 350 is also uniquely provided with a plurality of macro rate flow control channels 362*a*, 362*b*, 362*c*, 362*d* and 362*e* respectively, each having an inlet and an outlet (FIG. 105). The outlets of the macro rate flow control channels are in communication with the spaced apart macro rate outlet ports of the cover member 350.

Also forming a part of the flow control means of this latest form of the invention is a micro rate selector knob 370 that is carried within a horizontal bore 372 formed in housing portion 456*b*. As before, selector knob 370 includes a body portion 370*a* and an enlarged diameter head portion 370*b*. As illustrated in FIGS. 99, 103A and 103B, selector knob 370 is uniquely provided with a plurality of radially extending flow control channels 374*a*, 374*b*, 374*c*, 374*d* and 374*e*, each having an inlet port and an outlet port which is in fluid communication with an axially extending passageway 376. Axially extending passageway 376 is, in turn, in fluid communication with administration line 108, which is also identical in construction and operation to that shown in FIGS. 99 through 114. As earlier described the micro selector knob functions to selectively align one of the inlets of the radially extending flow control channels of the selector knob with a selected one of the spaced apart micro rate fluid outlets 356*a*, 356*b*, 356*c*, 356*d* and 356*e* of the rate control housing 350 (FIGS. 103B and 103C).

Also forming a part of the flow control means of this latest form of the invention is a macro rate selector knob 380 that is carried within a horizontal bore 382 formed in housing portion 456*b*. Selector knob 380 includes an enlarged diameter head portion 380*a* and a generally cylindrical body portion 380*b*. As illustrated in FIG. 103D, selector knob 380 is uniquely provided with a plurality of radially extending flow control channels 384*a*, 384*b*, 384*c*, 384*d* and 384*e*, each having an inlet port and an outlet port which it is in fluid communication with an axially extending passageway 386. Axially extending passageway 386 is, in turn, in fluid communication with administration line 108.

As before, selector knob 380 functions to selectively align one of the inlets of the radially extending flow control channels of the macro selector knob with a selected one of the spaced apart macro rate fluid outlets 360*a*, 360*b*, 360*c*, 360*d* and 360*e* of the rate control housing 350 (FIG. 108).

As best seen in FIG. 117, inlet port 354 of the rate control assembly is in communication with the outlet port 462 of reservoir 460 via a passageway 483 with which it is in communication. As the pusher assembly 170 is urged forwardly by the stored energy means, the fluid contained within reservoir 460 will flow through the outlet port 462, through passageway 483 and into inlet 354 of the rate control assembly in a manner to permit each of the micro channels and each of the macro channels of the rate control plate 350 to fill with the medicinal fluid to be dispensed to the patient.

In using the apparatus, rotation of the micro rate selector knob 370 will permit each of the spaced outlets of the micro channels to selectively be aligned with a selected one of the outlets 356a, 356b, 356c, 356d and 356e of the rate control cover 352. The fluid can then flow into a selected one of the plurality of passages 374a, 374b, 374c, 374d and 374e, formed in the micro rate selector knob 370, into axially extending passageway 376, into the administration line 108 via a circumferentially extending fluid flow passageway 387 (see FIGS. 103, 103C and 114) and then on to the patient at a precise micro rate of flow.

As before, selector knob 370 is provided with a plurality of circumferentially spaced apart indexing cavities that closely receive the end of an indexing finger 392a of an outwardly extending locking arm 392 (FIG. 118) which forms a part of the flow control means of the invention and functions to prevent rotation selector knob 370. (see also FIGS. 102 and 104). Finger 392a is continuously urged into a selected one of the indexing cavities 390 formed in knob 370 by a coiled spring 394 (FIGS. 97, 104 and 118). In order to permit rotation of knob 370, arm 392 must be pushed inwardly against the urging of spring 394.

In a similar manner, rotation of the macro rate selector knob 380 will permit each of the spaced outlets of the macro channels to selectively be aligned with a selected one of the outlets 360a, 360b, 360c, 360d and 360e of the rate control cover 352. The fluid can then flow into a selected one of the plurality of passages 384a, 384b, 384c, 384d and 384e formed in the micro rate selector knob 380, into axially extending passageway 386, into the administration line via a circumferentially extending fluid flow passageway 397 (see FIGS. 103 and 114), and then on to the patient at a precise macro rate of flow.

As shown in FIG. 103D, selector knob 380 is also provided with a plurality of circumferentially spaced apart indexing cavities 399 that closely receive the end of an indexing finger 402a of an outwardly extending locking arm 402 (FIG. 118), which forms a part of the flow control means of the invention and functions to prevent rotation selector knob 380, (FIGS. 97, 98, 102, 104 and 118). Finger 402a is continuously urged into a selected one of the indexing cavities 399 formed in knob 380 by a coiled spring 404 (FIGS. 97, 104 and 116). In order to permit rotation of knob 380, arm 402 must be pushed inwardly against the urging of spring 404.

The apparatus of this latest form of the invention also includes disabling means for irrevocably disabling the device and rendering it inert. This disabling means is identical in construction and operation to that described in connection with FIGS. 99 through 114.

Turning to FIGS. 119 and 120 still another form of the apparatus of the present form of the invention is there illustrated and generally designated by the numeral 482. This apparatus is also similar in some respects to the apparatus shown in FIGS. 94 through 114 and like numerals are used in FIGS. 119 and 120 to identify like components. As best seen in FIG. 119, the primary difference between this latest form of the invention and that shown in FIGS. 99 through 114 concerns the provision of a differently configured reservoir fill means for filling the device reservoir. More particularly, as will presently be described in greater detail, this alternate form of fill means comprises a pair of identical cartridge fill vial or containers 454, each having a hollow glass or plastic body portion that defines a fluid chamber that is closed by a pierceable, elastomeric septum.

The apparatus here comprises a snap together outer housing 486 having first and second portions 486a and 486b respectively and a front cover 486c. Housing portion 486b comprises the reservoir portion and the rate control, fill and delivery and control portions. When snapped together the housing portions define a carrying handle 487.

Disposed within first portion 486a of outer housing 486 is the novel stored energy means of the invention for causing the fluid contained within fluid reservoir 490 to controllably flow outwardly of the housing and into the fluid dispensing means. As before, in this latest form of the invention, the stored energy means comprises a constant force spring member 38 that is carried within the first portion 486a of the outer housing. Spring member 38 first extends due to fluid flowing into reservoir 490 and then controllably retracts in the manner shown in FIG. 119 to cause fluid flow from the outer housing, through the dispensing means of the invention and toward the patient. Stored energy member, or constant force spring 38, is of identical construction and functions in the same manner as that previously described. After the spring is extended it will tend to uniformly return toward its starting configuration and in so doing will exert a constant force on pusher member 170, which is housed within housing portion 486b in the manner shown in FIG. 119. As the spring returns to its starting configuration, the fluid contained within the fluid reservoir 490 will be caused to flow outwardly through outlet 492 and toward the flow rate control means of the invention.

With regard to the fill means of this latest form of the invention, which is also carried by first portion 486b of the outer housing, this important fill means functions to fill the reservoir 490 with the fluid to be dispensed. This fill means here comprises the previously described septum fill means, which is identical to that previously described, and also includes a vial fill means which includes two, rather than the one, cartridge type fill vials or fill containers.

As to the septum fill means, as illustrated in FIG. 119, second housing portion 486b includes a fluid passageway 494 which is in communication with inlet 496 of fluid reservoir 490. Proximate its lower end 494a, fluid passageway 494 communicates with a cavity 497 formed within the second housing portion. Disposed within cavity 497 is a pierceable septum 498 that comprises a part of the septum fill means of this latest form of the invention. As before, septum 498 is pierceable by the needle of the syringe (not shown) which contains the medicinal fluid to be dispensed and which can be used in a conventional manner to fill or partially fill reservoir 490 via passageway 494.

First portion 486a of the housing also includes a first chamber 500 for telescopically receiving a first medicament containing fill vial 454 and a second chamber 502 for receiving a second, identical medicament containing vial 454. The fill vials 454 are of identical construction to vial 454 of the earlier described embodiment. More particularly, as shown in FIG. 119, each cartridge fill vial 454 comprises a hollow glass or plastic body portion 470 that defines a fluid chamber 472. Each fill vial 454 also has an open first end 454a and a second end 454b that is closed by a pierceable, elastomeric septum 474. An elastomeric plunger 478 is reciprocally movable within each fluid chamber 472. As shown in FIG. 119, a pair of hollow needles 479 are mounted within second portion 486b of the device housing and are located proximate the inboard end of chambers 472. Hollow needles 479 are adapted to pierce septums 474 when the fill vial is inserted into chambers 500 and 502 provided in housing portion 486a and pushed into the position shown in FIG. 119 by the pusher means, or pusher assembly 505. Hollow needles 479 communicate with spaced apart cavities 507 formed within second portion 486b of the housing so that as the fluid contained within the vial reservoirs is urged outwardly thereof by pusher 505a of the pusher assembly 505 fluid will flow into cavities 507. Disposed within each cavity 507 is a conventional, umbrella type check valve 316 which permits fluid flow toward fill passageway 494, but blocks fluid flow in the opposite direction.

A number of beneficial agents can be contained within vials 454 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Forming another very important aspect of the apparatus of this latest form of the invention is a novel flow control means that are carried by second portion 486b of outer housing 486. This flow control means, which is identical in construction and operation to that described in connection with the embodiment of the invention shown in FIGS. 99 through 114, functions in the manner previously described to precisely control the rate outwardly of fluid flow from reservoir 490 and toward the patient.

Turning next to FIGS. 121 through 126, yet another form of the apparatus of the present invention is there illustrated and generally designated by the numeral 522. This apparatus is similar in some respects to the apparatus shown in FIGS. 119 and 120 and like numerals are used in FIGS. 121 through 126 to identify like components. As best seen in FIG. 121, the primary difference between this latest form of the invention and that shown in FIGS. 119 and 120 concerns the provision of two different types of fill vials. This alternate form of fill means comprises the previously described septum fill means, which is identical to that previously described, and also includes a vial fill means which includes the two differently configured fill vials or fill containers.

As to the septum fill means, as illustrated in FIG. 121, second housing portion 524b includes a fluid passageway 526 which is in communication with inlet 528 of fluid reservoir 530. Proximate its lower end 526a, fluid passageway 526 communicates with a cavity 532 formed within the second housing portion. Disposed within cavity 532 is a pierceable septum 534 that comprises a part of the septum fill means of this latest form of the invention. As before, septum 534 is pierceable by the needle of a conventional syringe (not shown) which contains the medicinal fluid to be dispensed and which can be used in a conventional manner to fill or partially fill reservoir 530 via passageway 526.

First portion 524a of the housing 524 also includes a first chamber 536 for telescopically receiving the first medicament containing fill vial 454 and a second chamber 538 for receiving a second medicament containing vial 540. First vial 454, which is of identical construction to vial 454 of the earlier described embodiments, comprises a vial cartridge having a hollow glass or plastic body portion that defines a fluid chamber that is closed by a pierceable, elastomeric septum. However, the second vial cartridge 540 is of a uniquely different construction from the previously described medicament containing vials. More particularly, as will be discussed in greater detail hereinafter, this second vial cartridge is specially designed to enable the intermixing of a lypholized drug with a suitable diluent prior to the delivery of the mixture of the fluid reservoir of the device.

A number of beneficial agents can be contained within vials 454 and 540 and can be controllably dispensed to the patient, including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

As in the earlier described embodiments of the invention, another very important aspect of the apparatus of this latest form of the invention is a novel flow control means that are carried by second portion 524b of outer housing 524. This flow control means, which is identical in construction and operation to that described in connection with the first embodiment of the invention, functions to precisely control the rate outwardly of fluid flow from reservoir 530 and toward the patient.

With respect to second cartridge fill vial 540, this vial comprises a container of special design that includes a chamber 542 and uniquely contains a lyophilized drug 544 that is separated from a reconstituting fluid 546 by a barrier stopper 548 (FIG. 122). Lyophilized drug 544 can, by way of example, comprise anti-infectives or various other types of beneficial agents. Second cartridge fill vial 540 also includes an elastomeric plunger 550 that is reciprocally movable within fluid chamber 542.

As illustrated in FIGS. 121 and 126, a removable cover 552 of the device housing includes a pair of spaced apart pusher members 553 and 554 which engage plungers 476 and 550 respectively to push them forwardly of their respective container chambers.

As best seen in FIG. 122, cartridge assembly 540 comprises a vial 554 that is sealed at one end by plunger 550 and at the other end by a pierceable septum 556. Formed intermediate the ends of vial 554 is a raised outer wall portion 556 which permits fluid 546 to bypass a barrier stopper 548 as the barrier stopper is urged inwardly of the container by pressure exerted thereon by the fluid 546. Fluid 546 exerts pressure on barrier member 548 as a result of pusher member 554 exerting inward pressure on plunger 550, which pressure is, in turn, caused by the inward movement of plunger 550 as the cover 552 is mated with the apparatus housing.

A continued inward pressure exerted on plunger 548 will cause fluid 546 to flow past barrier member 548 via wall portion 556 so as to reconstitute lyophilized drug 544. Further pressure exerted on plunger 548 will cause the reconstituted drug formed by the fluid 546 which has been intermixed with drug 544 to flow through a hollow needle 560 which is carried by housing portion 524b, past a lower check valve 562, into a stub passageway 564, then into passageway 526 and finally into the device reservoir 530.

As the vial cover 552 is mated with the apparatus housing, pusher member 553 engages plunger 476 of vial 454 and moves it inwardly of the vial reservoir. Continued inward movement of the pusher member causes the fluid contained in the reservoir to be forced through a hollow needle 566, passed the upper umbrella check valve 568 mounted within second housing portion 524b, into a stub passageway 565, into a passageway 526 and finally into the device reservoir. As the fluid flows into reservoir 530, it will compress the stored energy means, or constant force spring 38 in the manner previously described.

Upon opening the fluid delivery path to the administration set, the stored energy means, or member 38, will tend to return to its starting configuration thereby controllably urging fluid flow outwardly of reservoir 530 via the flow control means of the invention which functions in the manner previously described.

Similarly, as in the earlier described embodiments, disabling means of the character previously described can be used to disable the apparatus of this latest form of the invention.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A dispensing apparatus for dispensing fluids to a patient comprising:
   (a) a housing having a fluid reservoir for containing fluid to be dispensed to the patient, said housing being provided with an inlet for permitting fluid flow into said fluid reservoir and an outlet for permitting fluid flow from said fluid reservoir;
   (b) fluid displacement means disposed within said housing for movement between a first position and a second position to cause said fluid contained within said fluid reservoir to flow toward said outlet;
   (c) stored energy means disposed within said outer housing for acting upon said fluid displacement means to cause said fluid displacement means to move toward said second position, said stored energy means comprising a constant force spring, said constant force spring being carried within a spring support mounted within said housing and comprising a high strength, long deflection device movable from a retracted configuration to an expanded configuration;
   (d) fill means carried by said housing for filling said reservoir with the fluid to be dispensed and for causing said constant force spring to move from said retracted configuration to said expanded configuration;
   (e) flow control means carried by said housing for controlling fluid flow from said reservoir to the patient, said flow control means comprising a selector member rotatably mounted within said housing, said selector member having a plurality of fluid passageways formed therein; and
   (f) dispensing means connected to said housing and in communication with said plurality of fluid passageways formed in said control member for dispensing fluid to the patient.

2. The apparatus as defined in claim 1 in which said housing includes a cavity in communication with said inlet of said fluid reservoir and in which said fill means comprises a pierceable septum disposed within said cavity.

3. The apparatus as defined in claim 1 in which said fill means comprises a fill vial receivable within said housing.

4. The apparatus as defined in claim 1 in which said housing further includes a connector portion and in which said fill means comprises a pierceable septum mounted within said housing and a fill syringe assembly interconnectable with said connector portion, said fill syringe assembly comprising:
   (a) a hollow housing having a chamber; and
   (b) a fill vial telescopically receivable with and said chamber of said hollow housing, said fill vial having a fluid reservoir and a plunger disposed within said fluid reservoir for movement between first and second positions.

5. The apparatus as defined in claim 1 in which said housing further includes a connector portion and in which said fill means comprises a pierceable septum mounted within said housing and a fill assembly including a connector component and a fill line connected to said connector component, said connector component being removably interconnectable with said connector portion of said housing.

6. The apparatus as defined in claim 1, further including volume indicator means carried by said housing for indicating the volume of fluid within said reservoir.

7. The apparatus as defined in claim 1, further including disabling means carried by said housing for preventing fluid flow toward the patient.

8. The apparatus as defined in claim 1, further including indicating means carried by said housing for indicating the volume of fluid being delivered to the patient over a particular period of time.

9. The apparatus as defined in claim 1 in which said flow control means further includes a flow rate control member mounted within said housing, said flow control member having a plurality of elongated fluidic flow control channels in communication with said plurality of fluid passageways formed in said selector member.

10. The apparatus as defined in claim 1 further including stop means for preventing rotation of said selector member.

11. The apparatus as defined in claim 1 in which said flow control means further comprises a second selector member rotatably mounted within said housing, said second flow selector member having a plurality of fluid passageways formed therein.

12. The apparatus as defined in claim 11 in which said flow control means further includes a flow rate control member mounted within said housing, said flow control member having a plurality of elongated fluidic flow control channels in communication with said plurality of fluid passageways formed in said second selector member.

13. The apparatus as defined in claim 12 in which said plurality of elongated fluidic flow control channels of said flow rate control member have a depth of approximately 10-100 um.

14. A dispensing apparatus for dispensing fluids to a patient comprising:
   (a) a housing having a fluid reservoir for containing fluid to be dispensed to the patient, said housing being provided with an inlet for permitting fluid flow into said fluid reservoir and an outlet for permitting fluid flow from said fluid reservoir;
   (b) fluid displacement means disposed within said housing for movement between a first position and a second position to cause said fluid contained within said fluid reservoir to flow toward said outlet;
   (c) stored energy means disposed within said outer housing for acting upon said fluid displacement means to cause said fluid displacement means to move toward said second position, said stored energy means comprising a constant force spring, said constant force spring being carried within a spring support mounted within said housing and comprising a high strength, long deflection device movable from a retracted configuration to an expanded configuration;
   (d) fill means carried by said housing for filling said reservoir with the fluid to be dispensed and for causing said constant force spring to move from said retracted configuration to said expanded configuration;
   (e) flow control means carried by said housing for controlling fluid flow from said reservoir to the patient, said flow control means comprising:

(i) a selector member rotatably mounted within said housing, said flow control member having a plurality of fluid passageways formed therein; and (ii) a flow rate control member mounted within said housing, said flow control member having a plurality of elongated fluidic flow control channels in communication with said plurality of fluid passageways formed in said selector member; and (f) dispensing means connected to said housing and in communication with said plurality of fluid.

15. The apparatus as defined in claim 14 further including stop means for preventing rotation of said selector member.

16. The apparatus as defined in claim 14 in which said housing includes a vial receiving chamber and in which said fill means comprises a fill vial receivable within said vial receiving chamber.

17. The apparatus as defined in claim 14 in which said plurality of elongated fluidic flow control channels of said flow rate control member have a depth of approximately 10-100 um.

18. The apparatus as defined in claim 14 and which said flow rate control member is constructed from a medical grade polymer and in which said fluid flow control channels are made by injection molding techniques.

19. The apparatus as defined in claim 14 and which said plurality of the elongated fluidic flow control channels will deliver fluid at a flow rate of between about 0.25 and about 5.0 milliliters per hour.

20. The apparatus as defined in claim 14 in which said flow control means further comprises a second selector member rotatably mounted within said housing, said second flow selector member having a plurality of fluid passageways formed therein in communication with said elongated fluidic flow control channels of said flow rate control member.

21. The apparatus as defined in claim 14 in which said housing further includes a connector portion and in which said fill means comprises a pierceable septum mounted within said housing and a fill syringe assembly interconnectable with said connector portion, said fill syringe assembly comprising:

(a) a hollow housing having a chamber; and (b) a fill vial telescopically receivable with and said chamber of said hollow housing, said fill vial having a fluid reservoir and a plunger disposed within said fluid reservoir for movement between first and second positions.

22. The apparatus as defined in claim 14 further including disabling means carried by said housing for irrevocably disabling the device and rendering it inert.

23. The apparatus as defined in claim 22 in which said disabling means comprises a disabling shaft that is telescopically movable within a passageway formed within said housing.

24. A dispensing apparatus for dispensing fluids to a patient comprising:

(a) a housing having a fluid reservoir for containing fluid to be dispensed to the patient, said housing being provided with an inlet for permitting fluid flow into said fluid reservoir and an outlet for permitting fluid flow from said fluid reservoir and including a vial receiving chamber for receiving a first fill vial;

(b) fluid displacement means disposed within said housing for movement between a first position and a second position to cause said fluid contained within said fluid reservoir to flow toward said outlet;

(c) stored energy means disposed within said outer housing for acting upon said fluid displacement means to cause said fluid displacement means to move toward said second position, said stored energy means comprising a constant force spring, said constant force spring being carried within a spring support mounted within said housing and comprising a high strength, long deflection device movable from a retracted configuration to an expanded configuration;

(d) fill means carried by said housing for filling said reservoir with the fluid to be dispensed and for causing said constant force spring to move from said retracted configuration to said expanded configuration, said fill means comprising said fill vial receivable within said vial receiving chamber;

(e) flow control means carried by said housing for controlling fluid flow from said reservoir to the patient, said flow control means comprising:

(i) a selector member rotatably mounted within said housing, said flow control member having a plurality of fluid passageways formed therein; and (ii) a flow rate control member mounted within said housing, said flow control member having a plurality of elongated fluidic flow control channels in communication with said plurality of fluid passageways formed in said selector member; and (f) dispensing means connected to said housing and in communication with said plurality of fluid.

25. The apparatus as defined in claim 24 in which said housing includes;

(a) a removable vial cover for covering said vial receiving chamber;

(b) a fluid passageway in communication with said inlet of said fluid reservoir; and (c) an elongated support mounted within said removable vial cover.

26. The apparatus as defined in claim 24 in which said housing includes:

(a) a fluid passageway in communication with said inlet of said fluid reservoir; and (b) an elongated support mounted within said vial receiving said elongated support haying an elongated hollow needle, said hollow needle defining a flow passageway in communication with said fluid passageway.

27. The apparatus as defined in claim 26 in which said fill means includes a second fill vial and which said housing comprises;

(a) a second chamber for receiving said second fill vial; and (b) an elongated support mounted within said second chamber, said elongated support having an elongated hollow needle, said hollow needle defining a flow passageway in communication with said fluid passageway.

28. The apparatus as defined in claim 27 in which each of said first and second fill vials has a first open end, a closed second end and each includes;

(a) a fluid reservoir disposed between said first and second ends; and (b) a pierceable plunger disposed within said fluid reservoir for movement between first and second positions.

29. The apparatus as defined in claim 28 in which said housing includes a cavity in communication with said inlet of said fluid reservoir and in which said fill means comprises a pierceable septum disposed within said cavity.

30. The apparatus as defined in claim 29 further including locking means carried by said housing for blocking rotation of said selector knob.

* * * * *